(12) United States Patent
Wunderlich et al.

(10) Patent No.: US 11,473,105 B2
(45) Date of Patent: Oct. 18, 2022

(54) POTENT AND BALANCED BIDIRECTIONAL PROMOTER

(71) Applicant: JANSSEN VACCINES & PREVENTION B.V., Leiden (NL)

(72) Inventors: Kerstin Wunderlich, Kassel (DE); Jort Vellinga, Voorschoten (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 997 days.

(21) Appl. No.: 16/301,013

(22) PCT Filed: May 11, 2017

(86) PCT No.: PCT/EP2017/061282
§ 371 (c)(1),
(2) Date: Nov. 13, 2018

(87) PCT Pub. No.: WO2017/194655
PCT Pub. Date: Nov. 16, 2017

(65) Prior Publication Data
US 2019/0264225 A1   Aug. 29, 2019

(30) Foreign Application Priority Data

May 12, 2016 (EP) ..................................... 16169284

(51) Int. Cl.
| | | |
|---|---|---|
| *C12N 15/86* | (2006.01) | |
| *C12N 15/113* | (2010.01) | |
| *C12N 15/11* | (2006.01) | |
| *A61K 48/00* | (2006.01) | |
| *A61K 35/761* | (2015.01) | |

(52) U.S. Cl.
CPC ............ *C12N 15/86* (2013.01); *A61K 35/761* (2013.01); *A61K 48/00* (2013.01); *C12N 2710/10334* (2013.01); *C12N 2710/10343* (2013.01); *C12N 2710/16122* (2013.01); *C12N 2830/205* (2013.01)

(58) Field of Classification Search
None
See application file for complete search history.

(56) References Cited

U.S. PATENT DOCUMENTS

| | | |
|---|---|---|
| 5,057,540 A | 10/1991 | Kensil et al. |
| 5,122,458 A | 6/1992 | Post et al. |
| 5,559,099 A | 9/1996 | Wickham et al. |
| 5,837,511 A | 11/1998 | Falck-Pedersen et al. |
| 5,837,520 A | 11/1998 | Shabram et al. |
| 5,846,782 A | 12/1998 | Wickham et al. |
| 5,891,690 A | 4/1999 | Massie |
| 5,965,541 A | 10/1999 | Wickham et al. |
| 5,981,225 A | 11/1999 | Kochanek et al. |
| 5,994,106 A | 11/1999 | Kovesdi et al. |
| 5,994,128 A | 11/1999 | Fallaux et al. |
| 6,020,191 A | 2/2000 | Scaria et al. |
| 6,040,174 A | 3/2000 | Imler et al. |
| 6,083,716 A | 7/2000 | Wilson et al. |
| 6,113,913 A | 9/2000 | Brough et al. |
| 6,225,289 B1 | 5/2001 | Kovesdi et al. |
| 6,261,823 B1 | 7/2001 | Tang et al. |
| 6,485,958 B2 | 11/2002 | Blanche et al. |
| 7,326,555 B2 | 2/2008 | Konz, Jr. et al. |
| 8,932,607 B2 | 1/2015 | Custers et al. |
| 2007/0258962 A1* | 11/2007 | Chatellard ............. C12N 15/85 424/93.21 |
| 2009/0210952 A1 | 8/2009 | Wu et al. |
| 2013/0158246 A1* | 6/2013 | Kobinger ............... C12N 15/86 536/23.72 |

FOREIGN PATENT DOCUMENTS

| | | | |
|---|---|---|---|
| EP | 0351585 | * | 6/1989 |
| EP | 0 853 660 B1 | | 1/2003 |
| EP | 1 230 354 B1 | | 1/2004 |
| EP | 1 601 776 B1 | | 7/2008 |
| JP | 2009/519715 A | | 5/2009 |
| WO | WO-0213758 A2 * | 2/2002 | ............... A61P 7/06 |
| WO | 03/049763 A1 | | 6/2003 |
| WO | 03/061708 A1 | | 7/2003 |
| WO | 03/078592 A2 | | 9/2003 |
| WO | 03/104467 A1 | | 12/2003 |
| WO | 2004/001032 A2 | | 12/2003 |
| WO | 2004/004762 A1 | | 1/2004 |
| WO | 2004/020971 A2 | | 3/2004 |
| WO | 2004/037294 A2 | | 5/2004 |

(Continued)

OTHER PUBLICATIONS

Geest et al., Sustained Expression of Human Apolipoprotein A-I after Adenoviral Gene Transfer in C57BL/6 Mice: Role of Apolipoprotein A-I Promoter, Apolipoprotein A-I Introns, and Human Apolipoprotein E Enhancer, Human Gene Therapy 11:101-112 (Jan. 1, 2000).*
Genbank M20656.1, Human apolipoprotein AI (ApoAI) 5' nontranslating region, 1994, pp. 1-2.*
Alexopoulou et al., The CMV early enhancer/chicken β actin (CAG) promoter can be used to drive transgene expression during the differentiation of murine embryonic stem cells into vascular progenitors, BMC Cell Biology 2008, pp. 1-11.*
Bigley, Pascal, translation WO 0213758, downloaded Jan. 1, 2022.*
Gao et al, Human adenovirus type 35: nucleotide sequence and vector development, Gene Therapy (2003) 10, 1941-1949.*
Golding, et al., "A bidirectional promoter architecture enhances lentiviral transgenesis in embryonic and extraembryonic stem cells", Gene , 18, pp. 817-826 (2011).

(Continued)

*Primary Examiner* — Maria Marvich
(74) *Attorney, Agent, or Firm* — Kramer & Amado, P.C.

(57) ABSTRACT

The invention provides a bidirectional hCMV-CAG4 promoter and recombinant vectors and recombinant virus comprising the bidirectional hCMV-CAG4 promoter operably linked to a first transgene in one direction and to a second transgene in the opposite direction. The invention also provides methods of making and using such recombinant vectors and recombinant virus.

15 Claims, 13 Drawing Sheets
Specification includes a Sequence Listing.

(56) References Cited

FOREIGN PATENT DOCUMENTS

| | | |
|---|---|---|
| WO | 2004/055187 A1 | 7/2004 |
| WO | 2005/002620 A1 | 1/2005 |
| WO | 2005/071093 A2 | 8/2005 |
| WO | 2005/080556 A2 | 9/2005 |
| WO | 2006/053871 A2 | 5/2006 |
| WO | 2006/108707 A1 | 10/2006 |
| WO | 2006/120034 A1 | 11/2006 |
| WO | 2007/100908 A2 | 9/2007 |
| WO | 2007/102872 A2 | 9/2007 |
| WO | 2007/104792 A2 | 9/2007 |
| WO | 2007/110409 A1 | 10/2007 |
| WO | 2009/026183 A1 | 2/2009 |
| WO | 2009/117134 A2 | 9/2009 |
| WO | 2010/085984 A1 | 8/2010 |
| WO | 2010/086189 A2 | 8/2010 |
| WO | 2010/096561 A1 | 8/2010 |
| WO | 2011/045378 A1 | 4/2011 |
| WO | 2011/045381 A1 | 4/2011 |
| WO | 2013/139911 A1 | 9/2013 |
| WO | 2013/139916 A1 | 9/2013 |
| WO | 2015/175639 A1 | 11/2015 |
| WO | 2016/166088 A1 | 10/2016 |

OTHER PUBLICATIONS

Moseley, et al., "Bidirectional expression of CUG and CAG expansion transcripts and intranuclear polyglutamine inclusions in spinocerebellar ataxia type 8", Nature Genetics, vol. 38, No. 7, pp. 759-769. (Jul. 2006).

Orekhova, et al., "Bidirectional Promoters in the Transcription of Mammalian Genomes", Biochemistry (Moscow), vol. 78, No. 4, pp. 335-341. (2013).

Youil, et al., "Comparative Analysis of the Effects of Packaging Signal, Transgene Orientation, Promoters, Polyadenylation Signals, and E3 Region on Growth Properties of First-Generation Adenoviruses", Human Gene Therapy, 14, pp. 1017-1034. (Jul. 1, 2003).

Tatsis, et al., "A CD46-binding chimpanzee adenovirus vector as a vaccine carrier", Mol Ther, 15(3), 608-617.

Vemula, et al., "Production of adenovirus vectors and their use as a delivery system for influenza vaccines", Expert Opin Biol Ther, 10(10), 1469-1487.

Vogels, "High-level expression from two independent expression cassettes in replication-incompetent adenovirus type 35 vector", J Gen Virol, 88(Pt 11), 2915-2924.

Vogels, et al., "Replication-deficient human adenovirus type 35 vectors for gene transfer and vaccination: efficient human cell infection and bypass of preexisting adenovirus immunity", J Virol, 77(15), 8263-8271.

Voigt, et al., "The English strain of rat cytomegalovirus (CMV) contains a novel captured CD200 (vOX2) gene and a spliced CC chemokine upstream from the major immediate-early region: further evidence for a separate evolutionary lineage from that of rat CMV Maastricht", J Gen Virol, 86(Pt 2), 263-274.

Walther, et al., "Viral vectors for gene transfer: a review of their use in the treatment of human diseases", Drugs, 60 (2), 249-271.

Zhou, et al., "A chimpanzee-origin adenovirus vector expressing the rabies virus glycoprotein as an oral vaccine against inhalation infection with rabies virus", Mol Ther, 14(5), 662-672.

Zhou, et al., "A universal influenza A vaccine based on adenovirus expressing matrix-2 ectodomain and nucleoprotein protects mice from lethal challenge", Mol Ther, 18(12), 2182-2189.

Abbink, et al., "Comparative seroprevalence and immunogenicity of six rare serotype recombinant adenovirus vaccine vectors from subgroups B and .", J Virol, 81(9), 4654-4663. doi: 10.1128/JVI.02696-06.

Abbink, et al., "Construction and evaluation of novel rhesus monkey adenovirus vaccine vectors", J Virol, 89(3), 1512-1522. doi: 10.1128/JVI.02950-14.

Abrahamsen, et al., "Construction of an adenovirus type 7a E1A-vector", J Virol, 71(11), 8946-8951.

Addison, et al., "Comparison of the human versus murine cytomegalovirus immediate early gene promoters for transgene expression by adenoviral vectors", J Gen Virol, 78 ( Pt 7), 1653-1661. doi: 10.1099/0022-1317-78-7-1653.

Amendola, "Coordinate dual-gene transgenesis by lentiviral vectors carrying synthetic bidirectional promoters", Nat Biotechnol, 23(1), 108-116.

Andrianaki, et al., "Dual transgene expression by foamy virus vectors carrying an endogenous bidirectional promoter". Gene Ther, 17(3), 380-388. doi: 10.1038/gt.2009.147.

Bangari, et al., "Development of nonhuman adenoviruses as vaccine vectors", Vaccine, 24(7), 849-862. doi: 10.1016/j.vaccine.2005.08.101.

Barry, "Nucleotide sequence and molecular analysis of the rhesus cytomegalovirus immediate-early gene and the UL 121-117 open reading frames", Virology, 215(1), 61-72. doi: 10.1006/viro.1996.0007.

Barski, "Human aldehyde reductase promoter allows simultaneous expression of two genes in opposite directions", Biotechniques, 36(3), 382-384, 386, 388.

Belousova, "Circumventing recombination events encountered with production of a clinical-grade adenoviral vector with a double-expression cassette", Mol Pharmacol, 70(5), 1488-1493.

Boshart, et al., "A very strong enhancer is located upstream of an immediate early gene of human cytomegalovirus". Cell, 41(2), 521-530.

Brough, et al., "A gene transfer vector-cell line system for complete functional complementation of adenovirus early regions E1 and E4", J Virol, 70(9), 6497-6501.

Chan, "Synergistic interactions between overlapping binding sites for the serum response factor and ELK-1 proteins mediate both basal enhancement and phorbol ester responsiveness of primate cytomegalovirus major immediate-early promoters in monocyte and T-lymphoc", J Virol, 70(12), 8590-8605.

Chang, et al., "Identification of a large bent DNA domain and binding sites for serum response factor adjacent to the NFI repeat cluster and enhancer region in the major IE94 promoter from simian cytomegalovirus", J Virol, 67(1), 516-529.

Chatellard, et al., "The IE2 promoter/enhancer region from mouse CMV provides high levels of therapeutic protein expression in mammalian cells", Biotechnol Bioeng, 96(1), 106-117.

Cohen, et al., "Chimpanzee adenovirus CV-68 adapted as a gene delivery vector interacts with the coxsackievirus and adenovirus receptor", J Gen Virol, 83(Pt 1), 151-155.

Collins, et al., "The ets-related transcription factor GABP directs bidirectional transcription", PLoS Genet, 3(11), e208. doi: 10.1371/journal.pgen.0030208.

Fallaux, et al., "New helper cells and matched early region 1-deleted adenovirus vectors prevent generation of replication-competent adenoviruses", Hum Gene Ther, 9(13), 1909-1917.

Farina, et al., "Replication-defective vector based on a chimpanzee adenovirus", J Virol, 75(23), 11603-11613.

Gao, et al., "A cell line for high-yield production of E1-deleted adenovirus vectors without the emergence of replication-competent virus", Hum Gene Ther, 11(1), 213-219.

Geisbert, et al., "Recombinant adenovirus serotype 26 (Ad26) and Ad35 vaccine vectors bypass immunity to Ad5 and protect nonhuman primates against ebolavirus challenge", J Virol, 85(9), 4222-4233.

Goerke, et al., "Development of a novel adenovirus purification process utilizing selective precipitation of cellular DNA", Biotechnol Bioeng, 91(1), 12-21.

Hansen, et al., "omplete sequence and genomic analysis of rhesus cytomegalovirus.", J Virol, 77(12), 6620-6636.

Harro, et al., "Safety and immunogenicity of adenovirus-vectored near-consensus HIV type 1 clade B gag vaccines in healthy adults", AIDS Res Hum Retroviruses, 25(1), 103-114.

Harro, et al., "Safety and immunogenicity of the Merck adenovirus serotype 5 (MRKAd5) and MRKAd6 human immunodeficiency virus type 1 trigene vaccines alone and in combination in healthy adults", Clin Vaccine Immunol, 16 (9), 1285-1292.

(56) References Cited

OTHER PUBLICATIONS

Havenga, et al., "Novel replication-incompetent adenoviral B-group vectors: high vector stability and yield in PER.C6 cells", J Gen Virol, 87(Pt 8), 2135-2143.
Heilbronn, et al., "Viral vectors for gene transfer: current status of gene therapeutics", Handb Exp Pharmacol(197), 143-170.
Holman, et al., "Two complex, adenovirus-based vaccines that together induce immune responses to all four dengue virus serotypes", Clin Vaccine Immunol, 14(2), 182-189.
Holterman, et al., "Novel replication-incompetent vector derived from adenovirus type 11 (Ad11) for vaccination and gene therapy: low seroprevalence and non-cross-reactivity with Ad5", J Virol, 78(23), 13207-13215.
Hu, "Comparative immunogenicity of recombinant adenovirus-vectored vaccines expressing different forms of hemagglutinin (HA) proteins from the H5 serotype of influenza A viruses in mice", Virus Res, 155(1), 156-162.
Kim, et al., "se of the human elongation factor 1 alpha promoter as a versatile and efficient expression system", Gene, 91(2), 217-223.
Kobinger, et al., "Chimpanzee adenovirus vaccine protects against Zaire Ebola virus", Virology, 346(2), 394-401.
Lasaro, et al., "New insights on adenovirus as vaccine vectors", Mol Ther, 17(8), 1333-1339.
Lemckert, et al., "Generation of a novel replication-incompetent adenoviral vector derived from human adenovirus type 49: manufacture on PER.C6 cells, tropism and immunogenicity", J Gen Virol, 87(Pt 10), 2891-2899.
Mullick, et al., "The cumate gene-switch: a system for regulated expression in mammalian cells", BMC Biotechnol, 6, 43.
Na, "Design of Ad5F35 vectors for coordinated dual gene expression in candidate human hematopoietic stem cells", Experimental Hematology, vol. 38, No. 6, pp. 446-452. (Jun. 1, 2010).
Nan, et al., "Development of an Ad7 cosmid system and generation of an Ad7deltaE1deltaE3HIV(MN) env/rev recombinant virus", Gene Ther, 10(4), 326-336.
Ogun, et al., "The oligomerization domain of C4 binding protein (C4bp) acts as an adjuvant, and the fusion protein comprised of the 19-kilodalton merozoite surface protein 1 fused with the murine C4bp domain protects mice against malaria". Infect Immun, 76(8), 3817-3823.
Ophorst, et al., "Immunogenicity and protection of a recombinant human adenovirus serotype 35-based malaria vaccine against Plasmodium yoelii in mice", Infect Immun, 74(1), 313-320.
Pham, et al., "Concordant activity of transgene expression cassettes inserted into E1, E3 and E4 cloning sites in the adenovirus genome", J Gene Med, 11(3), 197-206.
Post, et al., "Generation of bidirectional hypoxia/HIF-responsive expression vectors to target gene expression to hypoxic cells", Gene Ther, 8(23), 1801-1807.
Quilici, et al., "A minimal cytomegalovirus intron A variant can improve transgene expression in different mammalian cell lines", Biotechnol Lett, 35(1), 21-27.
Richardson, et al., "Enhanced Protection against Ebola Virus Mediated by an Improved Adevonirus-Based Vaccine", Plos One, vol. 4, No. 4,8 pages. (Apr. 23, 2009).
Robbins, et al., "Viral vectors for gene therapy", Pharmacol Ther, 80(1), 35-47.
Sandford, et al., "Rat cytomegalovirus has a unique immediate early gene enhancer", Virology, 222(2), 310-317.
Schepp-Berglind, et al., "Complex adenovirus-mediated expression of West Nile virus C, PreM, E, and NS1 proteins induces both humoral and cellular immune responses", Clin Vaccine Immunol, 14(9), 1117-1126.
Sullivan, et al., "Accelerated vaccination for Ebola virus haemorrhagic fever in non-human primates", Nature, 424 (6949), 681-684.
Sullivan, "Immune protection of nonhuman primates against Ebola virus with single low-dose adenovirus vectors encoding modified GPs", PLoS Med, 3(6), e177.
Riki Koda, "Cytomegalovirus (CMV): Virological features and measurement methods," Journal of the Showa University Society, 2013, vol. 73, No. 3, pp. 139-144. Relevance: CMV is a highly species-specific virus as described in Riki Koda (as seen in p. 139, left column, last paragraph).

* cited by examiner

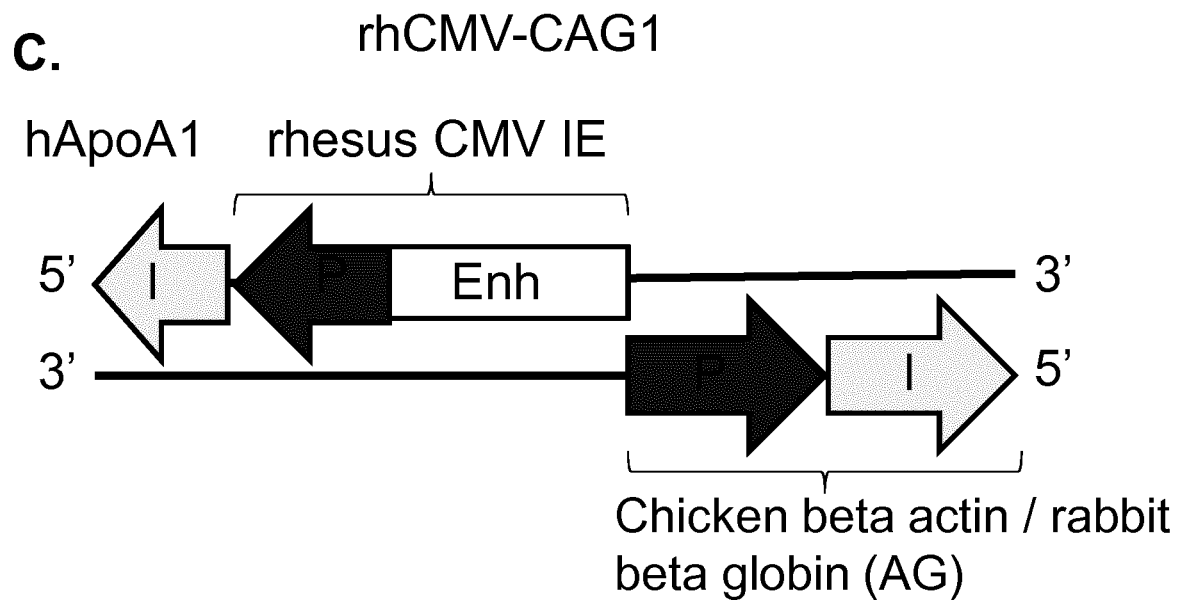
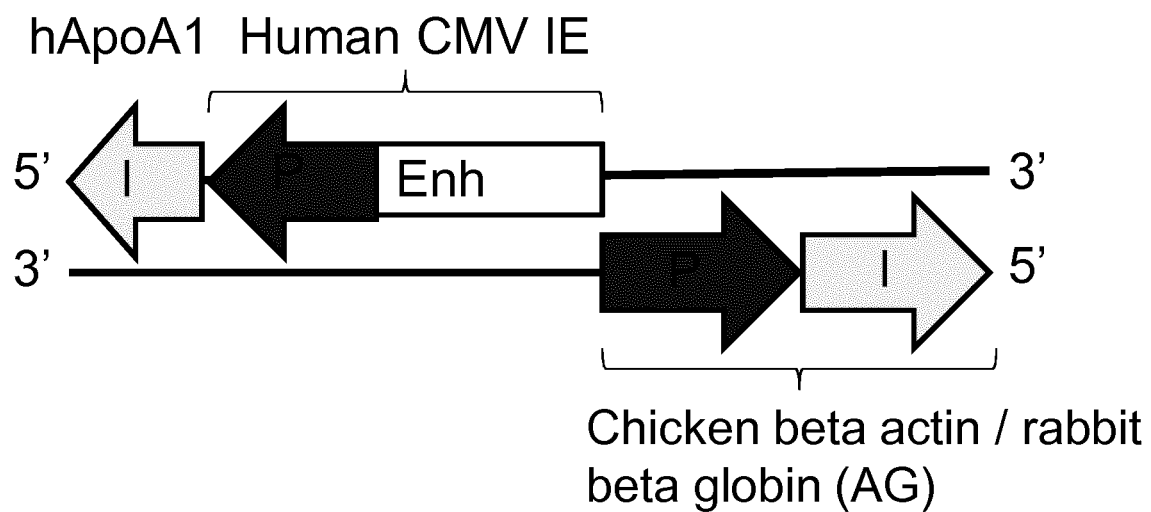
Fig. 1 - continued

E. rCMV-CAG
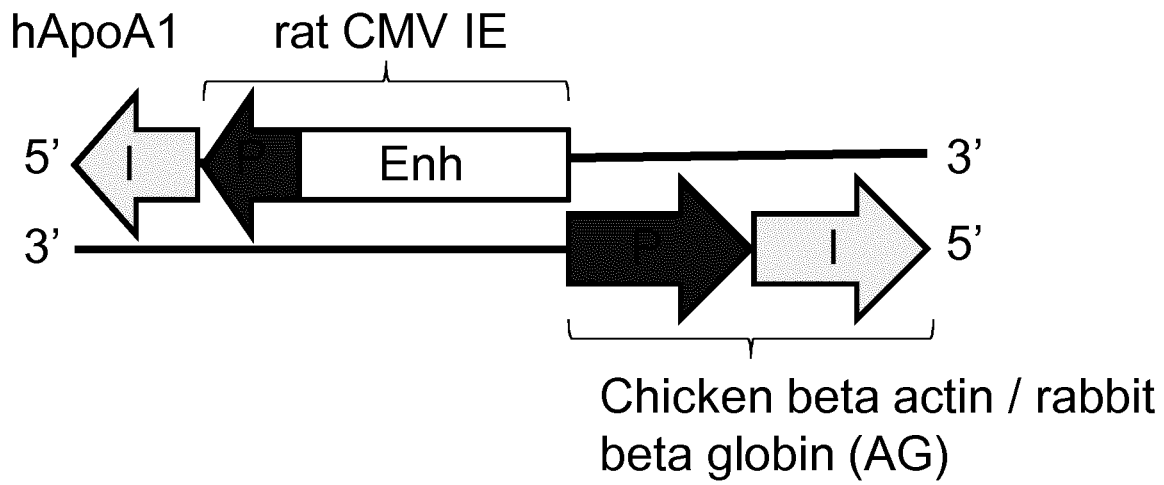
F. rhCMV-CAG2
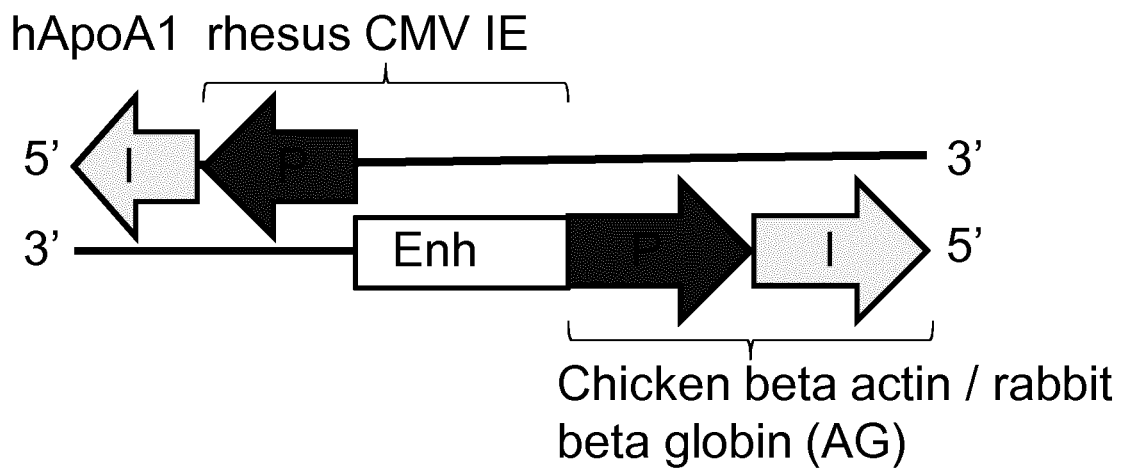
Fig. 1 - continued

G. rCMV bidir 1
rat CMV vOX2
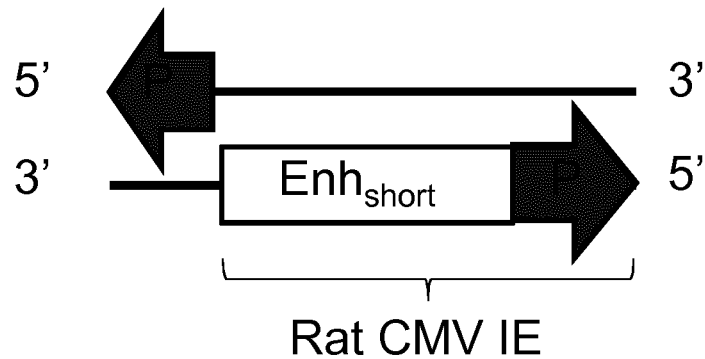
Rat CMV IE
H. rCMV bidir 2
rat CMV vOX2
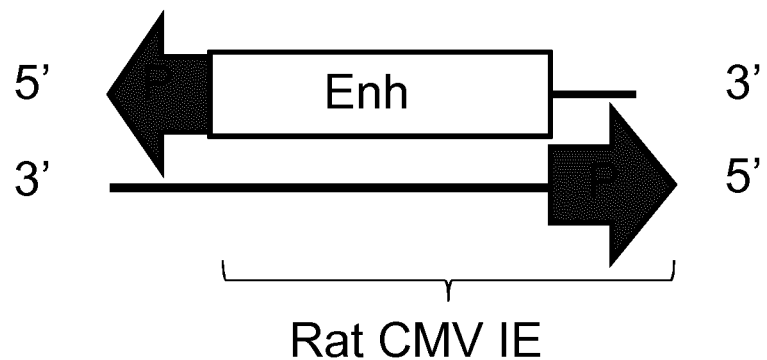
Rat CMV IE
Fig. 1 - continued

I. rCMV bidir 1.1
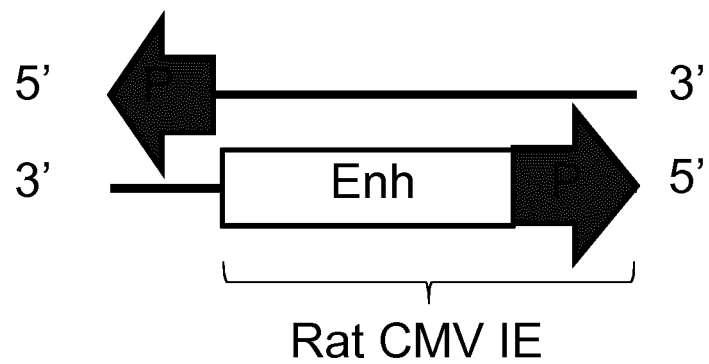
Fig. 1 - continued

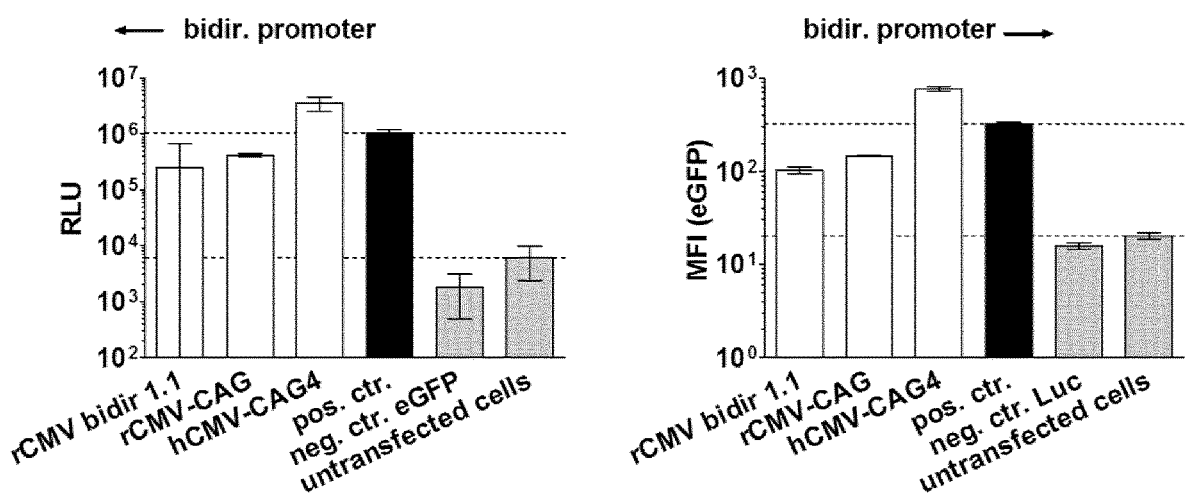
Fig. 2 - continued

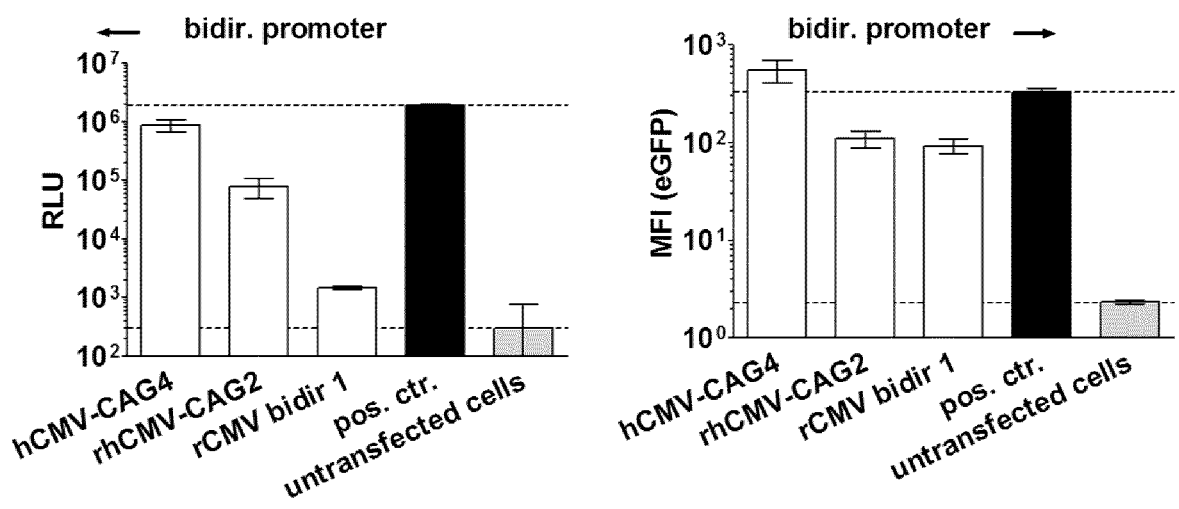
Fig. 2 - continued

A.

B.
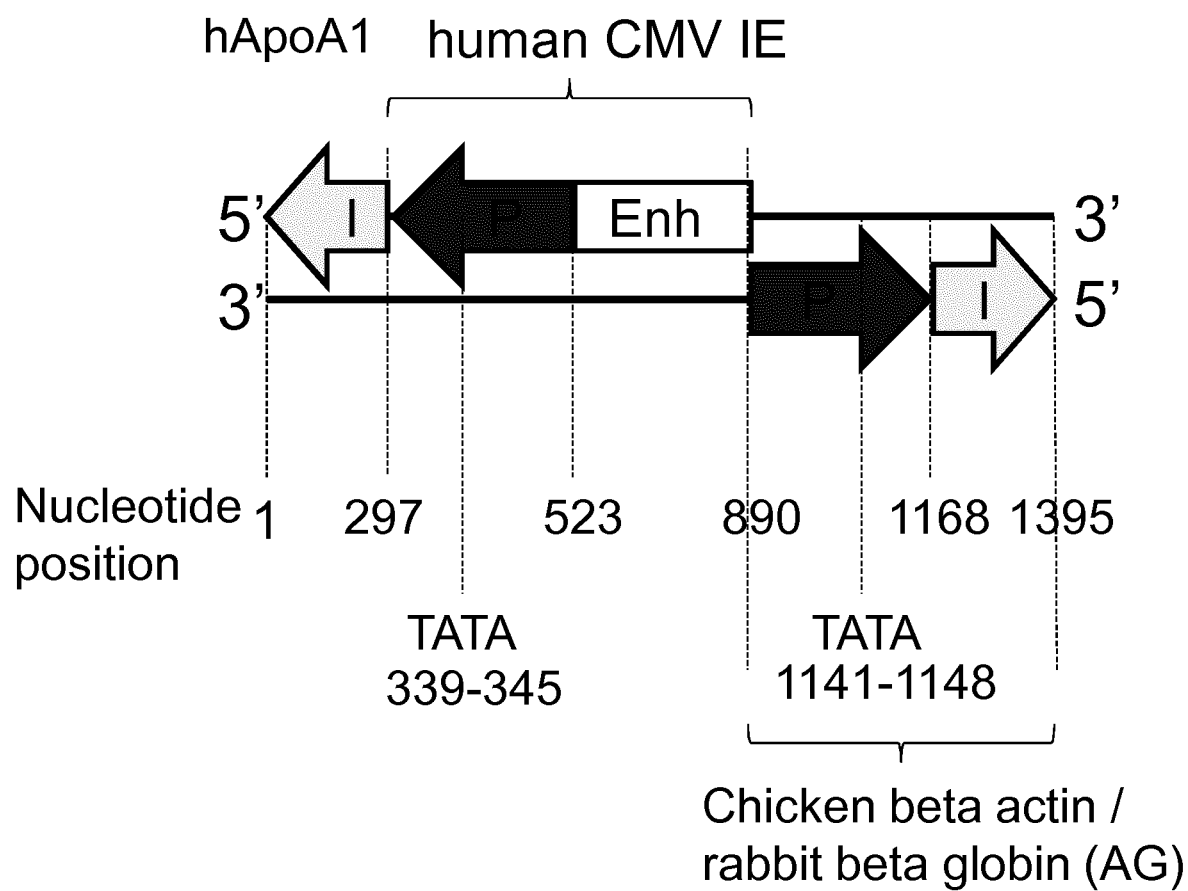
Fig. 3 - continued

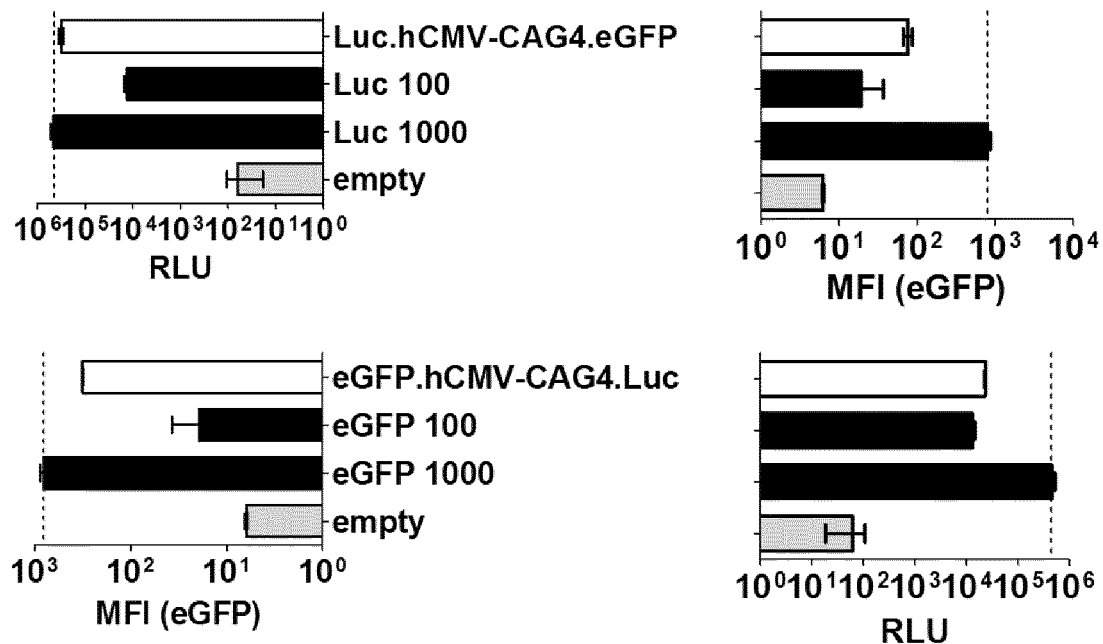
Fig. 4 - continued

SEQUENCE LISTING

```
<160> NUMBER OF SEQ ID NOS: 10

<210> SEQ ID NO 1
<211> LENGTH: 1769
<212> TYPE: DNA
<213> ORGANISM: Artificial Sequence
<220> FEATURE:
<223> OTHER INFORMATION: rCMV-hEF1a I

<400> SEQUENCE: 1
cacggccaag gtcagcaccg cagcttttat cctgaagggc cgtgggggac ctggaggaga      60
agaagggcct ggctgagtgg gtgccttcag tatgcagaag ccccgtgctc cccgaactca     120
gttgcagcca ggtgaggaga agggcacaga gcgggagaag acctcaggta ccagaggccc     180
ggcctggggc aaggcctgaa ccttgagctg gggagccaga gtgaccgggg caggcagcag     240
gacgcacctc cttctcgcag tctctaagca gccagctctt gcagggccta tttatgtatc     300
cgaagactgt gactgcccga acggcgttag gagatttata cctacgtctg acggtcatcg     360
tccaatagaa atcggagttt tgtaggtcat ctgtgggat tttccacagt ttagacgaaa     420
aattggcaga aaaaccagac cagatgtcga ggtcatctga gtcaacgtga ctcttatgca     480
gtttcggtgt ccttaacgag cgggcgtcac gtattctcag aataagagga acataaaatg     540
acaaagtctg caattaaaat tagagaaata agcagaaaca gatggtaggt cgttgacttt     600
tggctgactt atgaggtttc tatggagatt tggcttacaa tgttgctgaa ttgggtgttt     660
ccatagtgaa atgaccttaa tagttgcttt atttggcata gtcatagtga cttggcctta     720
aaagttgctt aactcgatat attttggtca aagaagttgc aaaacgggcc gttcccatag     780
cgatttcccg ggaaatcgtc cagtggtaat taccggccat aaatctcagt tctgtttata     840
agaccagatg ttgaccttaa gaaaaactca tgttttcaa aaaatttcca gttaaaatac     900
cctgattcag tatgactccc actgactcat aatgactgtt atgggtggaa atcgtgatat     960
ttaaactttc tcagaaacat aatgaagatt aatagttatt tcgactaaaa agaccacgga    1020
acgggatgtg acctttaaac aaatcatctg ttttgttata attataatga tttataatca    1080
gcccgatacg tgacctttaa gaagtttatt attctaagta gaaacagatg cgtgaggctc    1140
cggtgcccgt cagtgggcag agcgcacatc gcccacagtc cccgagaagt tgggggagg    1200 ggtcggcaat tgaaccggtg cctagagaag gtggcgcggg gtaaactggg aaagtgatgt    1260
cgtgtactgg ctccgccttt ttcccgaggg tgggggagaa ccgtatataa gtgcagtagt    1320
cgccgtgaac gttcttttc gcaacgggtt tgccgccaga acacaggtaa gtgccgtgtg    1380
tggttcccgc gggcctggcc tcgcgggcgg cgacggggcc cgtgcgtccc agcgcacatg    1440
ttcggcgagg cggggcctgc gagcgcggcc accgagaatc ggacgggggt agtctcaagc    1500
```

```
tggccggcct gctctggtgc ctggcctcgc gccgccgtgt atcgccccgc cctgggcggc    1560
aaggctggcc cggtcggcac cagttgcgtg agcggaaaga tggccgcttc ccggccctgc    1620
tgcagggagc tcaaaatgga ggacgcggcg ctcgggagag cgggcgggtg agtcacccac    1680
acaaaggaaa agggcctttc cgtcctcagc cgtcgcttca tgtgactcca ctggttcaaa    1740 gttttttct tccatttcag gtgtcgtga                                      1769
```

<210> SEQ ID NO 2
<211> LENGTH: 1540
<212> TYPE: DNA
<213> ORGANISM: Artificial Sequence
<220> FEATURE:
<223> OTHER INFORMATION: rCMV-hEF1a II

<400> SEQUENCE: 2

```
cacggccaag gtcagcaccg cagcttttat cctgaagggc cgtgggggac ctggaggaga     60
agaagggcct ggctgagtgg gtgccttcag tatgcagaag ccccgtgctc cccgaactca    120
gttgcagcca ggtgaggaga agggcacaga gcggagaaag acctcaggta ccagaggcc    180 ggcctggggc aaggcctgaa ccttgagctg gggagccaga gtgaccgggg caggcagcag    240
gacgcacctc cttctcgcag tctctaagca gccagctctt gcagggccta tttatgtatc    300
cgaagactgt gactgcccga acggcgttag gagatttata cctacgtctg acggtcatcg    360
tccaatagaa atcggagttt gtaggtcat ctgtggggat tttccacagt ttagacgaaa    420
aattggcaga aaaccagac cagatgtcga ggtcatctga gtcaacgtga ctcttatgca    480
gtttcggtgt ccttaacgag cgggcgtcac gtattctcag aataagagga acataaaatg    540
acaaagtctg caattaaaat tagagaaata agcagaaaca gatggtaggt cgttgacttt    600
tggctgactt atgaggtttc tatggagatt tggcttacaa tgttgctgaa ttgggtgttt    660
ccatagtgaa atgaccttaa tagttgcttt atttggcata gtcatagtga cttggcctta    720
aaagttgctt aactcgatat attttggtca agaagttgc aaaacgggcc gttcccatag    780
cgatttcccg ggaaatcgtc cagtggtaat taccggccat aaatctcagt tctgttata    840 agaccagatg ttgaccttaa gaaaaactca tgttttcaa aaaatttcca gttaaaatac    900
cctgattcag tatgactccc actgactcat aatgactgtt atgggtggaa atcgtgatat    960 ttaaacttc tcagaaacat aatgaagatt aatagttatt tcgactaaaa agaccacgga   1020
acgggatgtg acctttaaac aaatcatctg ttttgttata attataatga tttataatca   1080
gcccgatacg tgacctttaa gaagtttatt attctaagta gaaacagatg cgtgaggctc   1140
cggtgcccgt cagtgggcag agcgcacatc gcccacagtc cccgagaagt tgggggagg   1200 ggtcggcaat tgaaccggtg cctagagaag gtggcgcggg gtaaactggg aaagtgatgt   1260
cgtgtactgg ctccgccttt ttcccgaggg tgggggagaa ccgtatataa gtgcagtagt   1320
cgccgtgaac gttctttttc gcaacgggtt tgccgccaga acacaggtaa gtgccgtgtg   1380
tgcgggcggc gacggggccc gtgcgtccca gcgcacatgt tcggcgaggc ggggcctgta   1440
tcgccccgcc ctgggcggca aggcgagcgg gcgggtgagt cactcgcttc atgtgactcc   1500
actggttcaa agttttttc ttccatttca ggtgtcgtga                         1540
```

<210> SEQ ID NO 3
<211> LENGTH: 1655
<212> TYPE: DNA
<213> ORGANISM: Artificial Sequence
<220> FEATURE:
<223> OTHER INFORMATION: rhCMV-CAG1

-continued

<400> SEQUENCE: 3

```
cacggccaag gtcagcaccg cagcttttat cctgaagggc cgtgggggac ctggaggaga    60
agaagggcct ggctgagtgg gtgccttcag tatgcagaag ccccgtgctc cccgaactca   120
gttgcagcca ggtgaggaga agggcacaga gcgggagaag acctcaggta ccagaggccc   180
ggcctggggc aaggcctgaa ccttgagctg ggagccaga  gtgaccgggg caggcagcag   240
gacgcacctc cttctcgcag tctctaagca gccagctctt gcaggggccta tttatgtctt   300
ggcaagctct atccgcattc aatgcaccg tccccggcta tggaggctgg atcggtcccg    360
gtctcttcca atggagctcc tccgacgtcc caggcagaa tggcggttcc ctaaacgagc    420
attgcttata tagacctccc attaggcacg cctaccgcca tttacgtcaa tggaacgccc   480
atttgcgtca ttgcccccttc ccattgacgt caatggggat gttgtacttg gcagccatgc   540
cgggccattt accgccattg acgtcaatgg gagtacctgc caatgtaccc ttggcgtact   600
tgccaatagt aatgtacttg ccaagttact attaatagat attgatgtac tgccaagtgg   660
gccatttacc gtcattgacg tcaataggg  gcgtgagaac ggatatgaat gggcaatgag   720
ccatcccatt gacgtcaatg gtgggtggtc ctattgacgt caatgggcat tgagccaggc   780
gggccattta ccgtaattga cgtcaatggg ggaggcgcca tatacgtcaa taggaccgcc   840
catatgacgt caataggaaa gaccatatat agagaccatt gacgtcaatg gggagtggc   900
tatgggcggt attaggaagc cccatatatg gtatatggga ccgcccattg ggaggggcta   960
tctacgtcaa taggaaaaacc catatatgga atactatatg gcatagggcc aatacatagt  1020
attgaacctg gccaatagcc atattggcat agggccatat tggatattgc ctatatattg  1080
atcctggcat atagccaata tggccgccat tattggcacc atgccaattc aatgcggcca  1140
tcgatggtac gtcgaggtga gccccacgtt ctgcttcact ctccccatct ccccccctc   1200
cccaccccca attttgtatt tatttatttt ttaattattt tgtgcagcga tgggggcggg  1260
ggggggggg gcgcgcgcca ggcggggcgg ggcggggcga gggcggggc ggggcgaggc   1320
ggagaggtgc ggcggcagcc aatcagagcg cgcgctccg aaagtttcct tttatggcga   1380
ggcggcggcg gcggcggccc tataaaaagc gaagcgcgcg gcgggcggga gtcgctgcgt  1440
tgccttcgcc ccgtgccccg ctccgcgccg cctcgcgccg cccgccccgg ctctgactga  1500
ccgcgttact cccacaggtg agcgggcggg acggcccttc cctccgggc tgtaattagc   1560
ctagagcctc tgctaaccat gttcatgcct tcttcttttt cctacagctc ctgggcaacg  1620
tgctggttat tgtgctgtct catcatttg  gcaaa                              1655
```

<210> SEQ ID NO 4
<211> LENGTH: 1395
<212> TYPE: DNA
<213> ORGANISM: Artificial Sequence
<220> FEATURE:
<223> OTHER INFORMATION: hCMV-CAG4

<400> SEQUENCE: 4

```
cacggccaag gtcagcaccg cagcttttat cctgaagggc cgtgggggac ctggaggaga    60
agaagggcct ggctgagtgg gtgccttcag tatgcagaag ccccgtgctc cccgaactca   120
gttgcagcca ggtgaggaga agggcacaga gcgggagaag acctcaggta ccagaggccc   180
ggcctggggc aaggcctgaa ccttgagctg ggagccaga  gtgaccgggg caggcagcag   240
gacgcacctc cttctcgcag tctctaagca gccagctctt gcaggggccta tttatgtgcg  300
```

| | |
|---|---:|
| atctgacggt tcactaaacg agctctgctt atatagacct cccaccgtac acgcctaccg | 360 |
| cccatttgcg tcaatggggc ggagttgtta cgacattttg gaaagtcccg ttgattttgg | 420 |
| tgccaaaaca aactcccatt gacgtcaatg gggtggagac ttggaaatcc ccgtgagtca | 480 |
| aaccgctatc cacgcccatt gatgtactgc caaaaccgca tcaccatggt aatagcgatg | 540 |
| actaatacgt agatgtactg ccaagtagga aagtcccata aggtcatgta ctgggcataa | 600 |
| tgccaggcgg gccatttacc gtcattgacg tcaatagggg gcgtacttgg catatgatac | 660 |
| acttgatgta ctgccaagtg gcagtttacc gtaaatact ccacccattg acgtcaatgg | 720 |
| aaagtcccta ttggcgttac tatgggaaca tacgtcatta ttgacgtcaa tgggcggggg | 780 |
| tcgttgggcg gtcagccagg cgggccattt accgtaagtt atgtaacgcg gaactccata | 840 |
| tatgggctat gaactaatga ccccgtaatt gattactatt aataactagt gtcgaggtga | 900 |
| gccccacgtt ctgcttcact ctccccatct cccccccctc cccaccccca attttgtatt | 960 |
| tatttatttt ttaattattt tgtgcagcga tgggggcggg gggggggggg gcgcgcgcca | 1020 |
| ggcggggcgg ggcggggcga ggggcggggc ggggcgaggc ggagaggtgc ggcggcagcc | 1080 |
| aatcagagcg gcgcgctccg aaagtttcct tttatggcga ggcggcggcg gcggcggccc | 1140 |
| tataaaaagc gaagcgcgcg gcgggcggga gtcgctgcgt tgccttcgcc ccgtgccccg | 1200 |
| ctccgcgccg cctcgcgccg cccgccccgg ctctgactga ccgcgttact cccacaggtg | 1260 |
| agcgggcggg acgcccttc tcctccgggc tgtaattagc ctagagcctc tgctaaccat | 1320 |
| gttcatgcct tcttcttttt cctacagctc ctgggcaacg tgctggttat tgtgctgtct | 1380 |
| catcattttg gcaaa | 1395 |

<210> SEQ ID NO 5
<211> LENGTH: 1635
<212> TYPE: DNA
<213> ORGANISM: Artificial Sequence
<220> FEATURE:
<223> OTHER INFORMATION: rCMV-CAG

<400> SEQUENCE: 5

| | |
|---|---:|
| cacggccaag gtcagcaccg cagcttttat cctgaagggc cgtgggggac ctggaggaga | 60 |
| agaagggcct ggctgagtgg gtgccttcag tatgcagaag ccccgtgctc cccgaactca | 120 |
| gttgcagcca ggtgaggaga agggcacaga gcgggagaag acctcaggta ccagaggccc | 180 |
| ggcctggggc aaggcctgaa ccttgagctg gggagccaga gtgaccgggg caggcagcag | 240 |
| gacgcacctc cttctcgcag tctctaagca gccagctctt gcagggccta tttatgtatc | 300 |
| cgaagactgt gactgcccga acggcgttag agatttata cctacgtctg acggtcatcg | 360 |
| tccaatagaa atcggagttt tgtaggtcat ctgtggggat tttccacagt ttagacgaaa | 420 |
| aattggcaga aaaccagac cagatgtcga ggtcatctga gtcaacgtga ctcttatgca | 480 |
| gtttcggtgt ccttaacgag cgggcgtcac gtattctcag aataaggaga acataaaatg | 540 |
| acaaagtctg caattaaaat tagagaaata agcagaaaca gatggtaggt cgttgacttt | 600 |
| tggctgactt atgaggtttc tatggagatt tggcttacaa tgttgctgaa ttgggtgttt | 660 |
| ccatagtgaa atgaccttaa tagttgcttt atttggcata gtcatagtga cttggcctta | 720 |
| aaagttgctt aactcgatat attttggtca agaagttgc aaaacgggcc gttcccatag | 780 |
| cgatttcccg ggaaatcgtc cagtggtaat taccggccat aaatctcagt tctgttata | 840 |
| agaccagatg ttgaccttaa gaaaactca tgttttcaa aaaatttcca gttaaaatac | 900 |
| cctgattcag tatgactccc actgactcat aatgactgtt atgggtggaa atcgtgatat | 960 |

```
ttaaactttc tcagaaacat aatgaagatt aatagttatt tcgactaaaa agaccacgga    1020
acgggatgtg acctttaaac aaatcatctg ttttgttata attataatga tttataatca    1080
gcccgatacg tgacctttaa gaagtttatt attctaagta gaaacagatg gtcgaggtga    1140
gccccacgtt ctgcttcact ctccccatct cccccccctc cccacccccca attttgtatt    1200 tatttatttt ttaattattt tgtgcagcga tgggggcggg ggggggggg gcgcgcgcca     1260 ggcggggcgg ggcggggcga ggggcggggc gggcgaggc ggagaggtgc ggcggcagcc     1320
aatcagagcg gcgcgctccg aaagtttcct tttatggcga ggcggcggcg gcggcggccc    1380
tataaaaagc gaagcgcgcg gcgggcggga gtcgctgcgt tgccttcgcc ccgtgccccg    1440
ctccgcgccg cctcgcgccg cccgccccgg ctctgactga ccgcgttact cccacaggtg    1500
agcgggcggg acggcccttc tcctccgggc tgtaattagc ctagagcctc tgctaaccat    1560
gttcatgcct tcttcttttt cctacagctc ctgggcaacg tgctggttat tgtgctgtct    1620
catcattttg gcaaa                                                     1635

<210> SEQ ID NO 6
<211> LENGTH: 1655
<212> TYPE: DNA
<213> ORGANISM: Artificial Sequence
<220> FEATURE:
<223> OTHER INFORMATION: rhCMV-CAG2

<400> SEQUENCE: 6
cacggccaag gtcagcaccg cagcttttat cctgaagggc cgtgggggac ctggaggaga      60
agaagggcct ggctgagtgg gtgccttcag tatgcagaag ccccgtgctc cccgaactca     120
gttgcagcca ggtgaggaga agggcacaga gcgggagaag acctcaggta ccagaggccc     180
ggcctggggc aaggcctgaa ccttgagctg gggagccaga gtgaccgggg caggcagcag     240
gacgcacctc cttctcgcag tctctaagca gccagctctt gcagggccta tttatgtctt     300
ggcaagctct atccgcattc caatgcaccg tccccggcta tggaggctgg atcggtcccg     360
gtctcttcca atggagctcc tccgacgtcc ccaggcagaa tggcggttcc ctaaacgagc     420
attgcttata tagacctccc attaggcacg cctaccgcca tttacgtcaa tggaacgccc     480
atttgcgtca ttgccccttc ccattgacgt caatgggat gttgtacttg gcagccatgc     540
cgggccattt accgccattg acgtcaatgg gagtacctgc aatgtaccc ttggcgtact     600 tgccaatagt aatgtacttg ccaagttact attaatagat attgatggta ccatcgatgg     660
ccgcattgaa ttggcatggt gccaataatg gcggccatat ggctatatg ccaggatcaa     720 tatataggca atatccaata tggccctatg ccaatatggc tattggccag gttcaatact     780
atgtattggc cctatgccat atagtattcc atatatgggt tttcctattg acgtagatag     840
cccctcccaa tgggcggtcc catataccat atatgggct tcctaatacc gcccatagcc     900
actcccccat tgacgtcaat ggtctctata tatggtcttt cctattgacg tcatatgggc     960
ggtcctattg acgtatatgg cgcctccccc attgacgtca attacggtaa atggcccgcc    1020
tggctcaatg cccattgacg tcaataggac caccaccat tgacgtcaat gggatggctc    1080
attgcccatt catatccgtt ctcacgcccc ctattgacgt caatgacggt aaatggccca    1140
cttggcagta gtcgaggtga gccccacgtt ctgcttcact ctccccatct cccccccctc    1200 cccacccccca attttgtatt tatttatttt ttaattattt tgtgcagcga tgggggcggg    1260
gggggggggg gcgcgcgcca ggcggggcgg ggcggggcga ggggcggggc ggggcgaggc    1320
```

| | |
|---|---|
| ggagaggtgc ggcggcagcc aatcagagcg gcgcgctccg aaagtttcct tttatggcga | 1380 |
| ggcggcggcg gcggcggccc tataaaaagc gaagcgcgcg gcgggcggga gtcgctgcgt | 1440 |
| tgccttcgcc ccgtgccccg ctccgcgccg cctcgcgccg cccgccccgg ctctgactga | 1500 |
| ccgcgttact cccacaggtg agcggcgggg acggcccttc tcctccgggc tgtaattagc | 1560 |
| ctagagcctc tgctaaccat gttcatgcct tcttcttttt cctacagctc ctgggcaacg | 1620 |
| tgctggttat tgtgctgtct catcattttg gcaaa | 1655 |

```
<210> SEQ ID NO 7
<211> LENGTH: 938
<212> TYPE: DNA
<213> ORGANISM: Artificial Sequence
<220> FEATURE:
<223> OTHER INFORMATION: rCMV bidir 1.1

<400> SEQUENCE: 7
```

| | |
|---|---|
| cgacgttcat agctccgaat caagtctttc tgtgtacttg ccctatccgg atcacattac | 60 |
| tttataactt taaccacacc catatatcca gtacatacca attaacatct gtttctactt | 120 |
| agaataataa acttcttaaa ggtcacgtat cgggctgatt ataaatcatt ataattataa | 180 |
| caaaacagat gatttgttta aaggtcacat cccgttccgt ggtcttttta gtcgaaataa | 240 |
| ctattaatct tcattatgtt tctgagaaag tttaaatatc acgatttcca cccataacag | 300 |
| tcattatgag tcagtgggag tcatactgaa tcagggtatt ttaactggaa attttttgaa | 360 |
| aaacatgagt ttttcttaag gtcaacatct ggtcttataa acagaactga gatttatggc | 420 |
| cggtaattac cactgaacga tttcccggga aatcgctatg ggaacggccc gttttgcaac | 480 |
| ttctttgacc aaaatatatc gagttaagca acttttaagg ccaagtcact atgactatgc | 540 |
| caaataaagc aactattaag gtcatttcac tatggaaaca cccaattcag caacattgta | 600 |
| agccaaatct ccatagaaac ctcataagtc agccaaaagt caacgaccta ccatctgttt | 660 |
| ctgcttattt ctctaatttt aattgcagac tttgtcattt tatgttcctc ttattctgag | 720 |
| aatacgtgac gcccgctcgt taaggacacc gaaactgcat aagagtcacg ttgactcaga | 780 |
| tgacctcgac atctggtctg gtttttctgc caattttttcg tctaaactgt ggaaaatccc | 840 |
| cacagatgac ctacaaaact ccgatttcta ttggacgatg accgtcagac gtaggtataa | 900 |
| atctcctaac gccgttcggg cagtcacagt cttcggat | 938 |

```
<210> SEQ ID NO 8
<211> LENGTH: 1365
<212> TYPE: DNA
<213> ORGANISM: Artificial Sequence
<220> FEATURE:
<223> OTHER INFORMATION: rCMV bidir 2

<400> SEQUENCE: 8
```

| | |
|---|---|
| cgacgttcat agctccgaat caagtctttc tgtgtacttg ccctatccgg atcacattac | 60 |
| tttataactt taaccacacc catatatcca gtacatacca attaacgtct gacggtcatc | 120 |
| gtccaataga aatcggagtt ttgtaggtca tctgtgggga ttttccacag tttagacgaa | 180 |
| aaattggcag aaaaaccaga ccagatgtcg aggtcatctg agtcaacgtg actcttatgc | 240 |
| agtttcggtg tccttaacga gcgggcgtca cgtattctca gaataagagg aacataaaat | 300 |
| gacaaagtct gcaattaaaa ttagagaaat aagcagaaac agatggtagg tcgttgactt | 360 |
| ttggctgact tatgaggttt ctatggagat ttggcttaca atgttgctga attgggtgtt | 420 |
| tccatagtga aatgacctta atagttgctt tatttggcat agtcatagtg acttggcctt | 480 |

```
aaaagttgct taactcgata tattttggtc aaagaagttg caaaacgggc cgttcccata        540
gcgatttccc gggaaatcgt ccagtggtaa ttaccggcca taaatctcag ttctgtttat        600
aagaccagat gttgacctta agaaaaactc atgttttca aaaaatttcc agttaaaata         660
ccctgattca gtatgactcc cactgactca taatgactgt tatgggtgga atcgtgata        720 tttaaacttt ctcagaaaca taatgaagat taatagttat ttcgactaaa aagaccacgg       780
aacgggatgt gacctttaaa caaatcatct gttttgttat aattataatg atttataatc      840
agcccgatac gtgacctta agaagtttat tattctaagt agaaacagat ggtgacattt         900
agataaaagt aactatttag atctggattt aaatagagtt gagtgtctta ttcacattat       960
gtacgaattc aggattgtta tattaacatt tggcttgaat gtaagcactc tgttacaagc      1020
atacacttta acgtggcctt gaaaaataca tcagaccttg gagtagatta tacttctaag    1080
ttcttcacat tattcacaaa tgctgtgctt taaaacagat ggtttaaatc gaataatttt      1140
ttaaagagag tcatctataa ctcattctta atatgggaac tggctaaaag gtcataatta   1200
atcataggat attccgtgaa attgtgttgt ttttagaga aagggcaat agtttcataa        1260 taaagttcat ttttttaaat agcttaccag aattttttaa aatttccata aaaatatcta    1320
ggtataaatc tcctaacgcc gttcgggcag tcacagtctt cggat                     1365
```

<210> SEQ ID NO 9
<211> LENGTH: 829
<212> TYPE: DNA
<213> ORGANISM: Artificial Sequence
<220> FEATURE:
<223> OTHER INFORMATION: hCMV promoter

<400> SEQUENCE: 9

```
tcaatattgg ccattagcca tattattcat tggttatata gcataaatca atattggcta       60
ttggccattg catacgttgt atccatatca taatatgtac atttatattg gctcatgtcc     120
aacattaccg ccatgttgac attgattatt gactagttat taatagtaat caattacggg     180
gtcattagtt catagcccat atatggagtt ccgcgttaca aacttacgg taaatggccc     240 gcctggctga ccgcccaacg acccccgccc attgacgtca ataatgacgt atgttccat     300 agtaacgcca ataggacttt ccattgacg tcaatgggtg gagtattac ggtaaactgc     360 ccacttggca gtacatcaag tgtatcatat gccaagtacg ccccctattg acgtcaatga     420
cggtaaatgg cccgcctggc attatgccca gtacatgacc ttatgggact ttcctacttg    480
gcagtacatc tacgtattag tcatcgctat taccatggtg atgcggtttt ggcagtacat    540
caatgggcgt ggatagcggt ttgactcacg gggatttcca agtctccacc ccattgacgt   600
caatgggagt ttgttttggc accaaaatca acgggacttt ccaaaatgtc gtaacaactc    660
cgccccattg acgcaaatgg gcggtaggcg tgtacggtgg gaggtctata taagcagagc     720
tcgtttagtg aaccgtcaga tcgcctggag acgccatcca cgctgttttg acctccatag   780
aagacaccgg gaccgatcca gcctccgcgg ccgggaacgg tgcattgga                 829
```

<210> SEQ ID NO 10
<211> LENGTH: 1365
<212> TYPE: DNA
<213> ORGANISM: Artificial Sequence
<220> FEATURE:
<223> OTHER INFORMATION: rCMV bidir 1

<400> SEQUENCE: 10

```
cgacgttcat agctccgaat caagtctttc tgtgtacttg ccctatccgg atcacattac       60
tttataactt taaccacacc catatatcca gtacatacca attaagatat ttttatggaa      120
attttaaaaa attctggtaa gctatttaaa aaaatgaact ttattatgaa actattgccc      180
ttttctctaa aaaacaacac aatttcacgg aatatcctat gattaattat gaccttttag      240
ccagttccca tattaagaat gagttataga tgactctctt taaaaaatta ttcgatttaa      300
accatctgtt ttaaagcaca gcatttgtga ataatgtgaa gaacttagaa gtataatcta      360
ctccaaggtc tgatgtattt ttcaaggcca cgttaaagtg tatgcttgta acagagtgct      420
tacattcaag ccaaatgtta atataacaat cctgaattcg tacataatgt gaataagaca      480
ctcaactcta tttaaatcca gatctaaata gttacttta tctaaatgtc accatctgtt       540
tctacttaga ataataaact tcttaaaggt cacgtatcgg gctgattata aatcattata      600
attataacaa aacagatgat ttgtttaaag gtcacatccc gttccgtggt cttttagtc       660 gaaataacta ttaatcttca ttatgtttct gagaaagttt aaatatcacg atttccaccc      720
ataacagtca ttatgagtca gtgggagtca tactgaatca gggtatttta actggaaatt      780
ttttgaaaaa catgagtttt tcttaaggtc aacatctggt cttataaaca gaactgagat      840
ttatggccgg taattaccac tggacgattt cccgggaaat cgctatggga acggccgtt       900 ttgcaacttc tttgaccaaa atatatcgag ttaagcaact tttaaggcca agtcactatg      960
actatgccaa ataagcaac tattaaggtc atttcactat ggaaacaccc aattcagcaa     1020
cattgtaagc caaatctcca tagaaacctc ataagtcagc caaaagtcaa cgacctacca     1080
tctgtttctg cttatttctc taattttaat tgcagacttt gtcattttat gttcctctta     1140
ttctgagaat acgtgacgcc cgctcgttaa ggacaccgaa actgcataag agtcacgttg     1200
actcagatga cctcgacatc tggtctggtt tttctgccaa tttttcgtct aaactgtgga     1260
aaatccccac agatgaccta caaaactccg atttctattg gacgatgacc gtcagacgta     1320
ggtataaatc tcctaacgcc gttcgggcag tcacagtctt cggat                     1365
```

POTENT AND BALANCED BIDIRECTIONAL PROMOTER

TECHNICAL FIELD

The invention relates to the field of medicine and to the field of gene delivery for applications in vaccination and gene therapy. More in particular, the invention relates to a potent and balanced bidirectional promoter for the expression of two transgenes with recombinant vectors, such as plasmid vectors, viral vectors and recombinant viruses.

BACKGROUND OF THE INVENTION

Recombinant vectors are used extensively in a variety of molecular biology applications for the expression of heterologous proteins, including, for example, their application in gene therapy and vaccination. For these gene therapy and vaccination applications, vectors, including viral vectors, are used as carriers for a gene or genes of interest to be introduced into host cells. For example, viral vectors can be used to express a gene or part thereof encoding a desired antigen to elicit an immune response.

The earliest viral vectors typically only included one transgene and many strategies are published for the early generation vectors. For example, published strategies report the use of a variety of different adenovirus (rAd) vectors and show that the transgene expression cassette can be placed in different regions of the rAd, e.g., in the E1 region, the E3 region, or between E4 and the right ITR. For vaccine purposes, however, more than one antigen or the same antigen from several different strains is often required to achieve protection and broad coverage. Therefore, in certain cases, it's desirable to express at least two antigens from one vector. Different approaches to encode two antigens in one viral vector have been described.

In a first two antigen approach with rAd, one antigen expression cassette was placed in the E1 region and a second one was placed in the E3 region (e.g. (Vogels et al., 2007)). In a different two antigen approach with rAd, one antigen expression cassette was placed in E1 and a second one between E4 and the right ITR (e.g. (Holman et al., 2007; Pham et al., 2009; Schepp-Berglind et al., 2007)). Another two antigen approach with rAd, is to use two antigen expression cassettes placed in the E1 region in a head-to-tail fashion using two different promoter sequences in an attempt to prevent genetic instability by recombination (e.g. (Belousova et al., 2006; C. D. Harro et al., 2009)).

Another example of a two antigen approach is to use an internal ribosomal entry site (IRES) of positive-stranded RNA-viruses, e.g., derived from encephalomyocarditis virus (EMCV) to produce a single transcript that is translated into two proteins (e.g. (Amendola, Venneri, Biffi, Vigna, & Naldini, 2005; Na & Fan, 2010)). Other examples include utilizing the host cell splicing machinery or use of "cleavage" peptides derived from positive-stranded RNA viruses such as the foot-and-mouth-disease 2A sequence or equivalents from other viruses to produce a polyprotein that is cleaved into two proteins. According to published reports, all of these strategies can be equally useful and successful.

Alternatively, use of bidirectional promoters is another approach for expressing two transgenes with viral vectors. For example, different bidirectional promoters have been described for lentiviral vectors (Heilbronn & Weger, 2010) and adenoviral vectors (Na & Fan, 2010; Post & Van Meir, 2001; Robbins & Ghivizzani, 1998; Walther & Stein, 2000).

In general, two different types of bidirectional promoters are known for use, naturally occurring sequences with bidirectional properties and synthetically designed bidirectional promoters. The naturally occurring sequences with bidirectional properties can be found in viruses, plants or mammalian genomes (Andrianaki, Siapati, Hirata, Russell, & Vassilopoulos, 2010; Barski, Siller-Lopez, Bohren, Gabbay, & Aguilar-Cordova, 2004). For example, it has been reported that many promoters in the human genome have some bidirectional properties. The human promoters with bidirectional properties are marked by an overrepresentation of GABP sites (Collins, Kobayashi, Nguyen, Trinklein, & Myers, 2007).

In contrast to the naturally occurring sequences, synthetic bidirectional promoters can be designed to take advantage of the desirable properties of different unidirectional promoters. For example, Amendola et al. created two different synthetic bidirectional promoters for use in lentiviral vectors by combining a minimal promoter derived from the human cytomegalovirus (minCMV) with the human phosphoglycerate kinase promoter (PGK) or the human ubiquitin C promoter (UBI C) (Amendola et al., 2005). To construct the bidirectional promoters, the unidirectional promoters were configured in an opposite orientation (head to head), making use of only one enhancer. According to Amendola et al., when the strong minimal promoter was combined with a full mammalian promoter in this configuration the result was coordinate expression from both sides. The analysis of expression potency and balance, however, did not include a thorough comparison to a known strong unidirectional promoter such as the full enhancer-containing human CMV promoter. In fact, for most of the published strategies using multivalent viral vectors encoding two antigens in one vector, there has not been systematic analysis to ensure that critical features of monovalent vectors are faithfully maintained. Important features for newly created multivalent vectors include, for example, genetic stability during upscaling, productivity of the vector at large scale, potent expression of both antigens, balanced expression of both antigens, and immunogenicity of both antigens expressed from the inserted expression cassettes.

A recently described strategy that yielded particularly good results compared to previously disclosed methods, used a bidirectional mouse Cytomegalovirus (mCMV) promoter to express two transgenes (WO 2016/166088 A1). A first transgene was operably linked to the bidirectional mCMV promoter in one direction and a second transgene was operably linked to the bidirectional mCMV promoter in the other direction. The rAd with the bidirectional mCMV promoter were determined to be genetically stable, providing genetic stability that was comparable to rAd with only a single transgene. Furthermore, it was determined that both transgenes were sufficiently expressed to generate immunogenic responses to both antigens based on ELISPOT and ELISA analysis of the immunogenicity of the expressed antigens with regard to T-cell and B-cell responses. The mCMV bidirectional promoter was thus described to be superior to several other previously described strategies. However, it was determined that the balance of the expression levels between both sides of the mCMV promoter could be further improved. There was approximately a 10-times higher expression of an antigen positioned at the right side (3'end) of the bidirectional mCMV promoter compared to the antigen positioned at the left side (5'end) of the promoter. The imbalance in expression of the two encoded antigens leads to a stronger immune response directed against the highly expressed antigen compared to the lower expressed antigen. This kind of differential expression could be useful for certain applications, but for other applications it is also desirable to have a strategy that combines several advantages of the mCMV promoter with a more balanced expression, i.e. a bidirectional promoter that is both potent and more balanced than the bidirectional mCMV promoter and other bidirectional promoters that have been described in the literature.

Thus, a need remains to identify bidirectional promoters that are both potent and have an improved balance in expression from both sides compared to the mCMV bidirectional promoter, and to provide recombinant viruses that are genetically stable with potent and balanced expression of two transgenes.

SUMMARY OF THE INVENTION

The present invention provides recombinant nucleic acid molecules comprising a bidirectional hCMV-CAG4 promoter and vectors, including, for example, plasmid vectors, viral vectors, and viruses comprising the bidirectional hCMV-CAG4 promoter. The recombinant vectors of the present invention comprise two transgenes, wherein the transcriptional direction (5' to 3') of the hCMV and CAG portions of the hCMV-CAG4 bidirectional promoter point away from each other (head to head configuration), wherein a first transgene is operably linked in one direction on the left side, with expression controlled by the hCMV portion of the bidirectional promoter, and a second transgene is operably linked in the opposite direction on the right side, with expression controlled by the CAG portion of the bidirectional promoter. The hCMV enhancer is placed in the middle between the two different promoters pointing towards the hCMV promoter part. Since enhancers can be orientation-independent the enhancer provides coordinate expression of both transgenes operably linked to the hCMV and the CAG portions of the bidirectional promoter. See, for example, FIG. 1D shows the identity and orientation for different building blocks of a representative hCMV-CAG4 promoter. Preferably, a hCMV-CAG4 promoter according to the invention comprises a nucleotide sequence that is at least 80%, preferably at least 85%, more preferably at least 90%, still more preferably at least 95%, and up to 100%, identical to SEQ ID NO: 4.

In certain embodiments, the recombinant viruses and recombinant viral vectors are recombinant adenoviruses (rAd) and rAd vectors. The rAd produced with the bidirectional hCMV-CAG4 promoter of the present invention are genetically stable, with no deletion bands detected by PCR analysis up to passage 13 (p13), thus providing genetic stability that is comparable to viruses with only a single transgene. Furthermore, the bidirectional hCMV-CAG4 promoter provides potent and balanced expression of the two transgenes that is comparable to expression from a unidirectional promoter. Thus, the bidirectional hCMV-CAG4 promoter of the present invention is suitable for use in gene therapy and vaccine applications with recombinant (viral) vectors where balanced and potent expression are important.

The general and preferred embodiments are defined, respectively, by the independent and dependent claims appended hereto, which for the sake of brevity are incorporated by reference herein. Other preferred embodiments, features, and advantages of the various aspects of the invention will become apparent from the detailed description below taken in conjunction with the appended drawing figures.

In one embodiment, the present invention provides a bidirectional hCMV-CAG4 promoter comprising the hCMV promoter on the left side and the CAG promoter on the right side, wherein the bidirectional hCMV-CAG4 promoter is operably linked to a first transgene in one direction on the left side and the bidirectional hCMV-CAG4 promoter is operably linked to a second transgene on the right side in the other direction.

In another embodiment, the present invention also provides a method of producing a recombinant virus comprising a first and a second transgene, the method comprising: preparing a construct comprising a bidirectional hCMV-CAG4 promoter operably linked to a first transgene in one direction and to a second transgene in the opposite direction, and incorporating said construct into the genome of the recombinant virus.

In certain embodiments, the recombinant virus is a recombinant adenovirus.

In certain embodiments, the recombinant adenovirus has a deletion in the E1 region, and in certain embodiments comprises the bidirectional hCMV-CAG4 promoter and first and second transgenes in this E1 region. Alternatively, other regions of the recombinant adenovirus could also be used. For example, the bidirectional promoter expression cassette could also be placed in the E4-rITR region of the recombinant adenovirus.

In certain embodiments, the first and second transgene are different and at least one of them encodes an antigen. In certain embodiments both encode a different antigen.

In certain embodiments, the adenovirus is a human adenovirus serotype 26 or a human adenovirus serotype 35.

In another embodiment, the present invention also provides a method for expressing at least two transgenes in a cell, the method comprising providing a cell with a recombinant vector according to the invention.

In another embodiment, the present invention also provides a method for inducing an immune response against at least two antigens, the method comprising administering to a subject a recombinant vector according to the invention.

In another embodiment, the present invention also provides a recombinant DNA molecule comprising the genome of a recombinant adenovirus according to the invention.

In another embodiment, the present invention also provides a pharmaceutical composition comprising a recombinant vector, such as a recombinant adenovirus, according to the invention and a pharmaceutically acceptable carrier or excipient. In certain embodiments, the pharmaceutical composition is a vaccine.

I, rCMV-hEF1α II, and rhCMV-CAG1, compared to the positive control of Luciferase or eGFP under control of a unidirectional hCMV promoter and a negative control of untransfected cells. (B) Shown are bar graphs of the results for Luciferase expression from the left side and eGFP expression from the right side of different bidirectional promoters. Results in each graph are shown in order from left to right for rCMV bidir 1.1, rCMV-CAG, and hCMV-CAG4, compared to the positive control of Luciferase or eGFP under control of a unidirectional hCMV promoter and a negative control of untransfected cells. (C) Shown are bar graphs of the results for Luciferase expression from the left side and eGFP expression from the right side of different bidirectional promoters. Results in each graph are shown in order from left to right for hCMV-CAG4, rhCMV-CAG2, and rCMV bidir1, compared to the positive control of Luciferase or eGFP under control of a unidirectional hCMV promoter and a negative control of untransfected cells.

Figure 3:
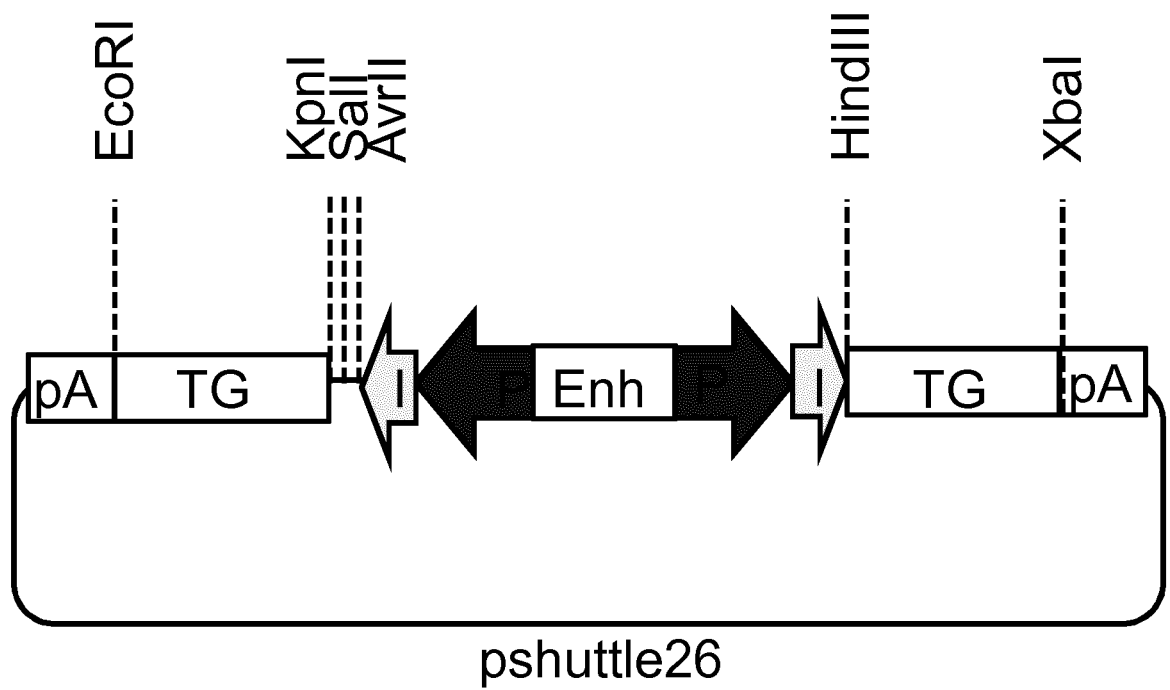

FIG. 3: (A) Organization of bidirectional expression cassette for bidirectional promoter hCMV-CAG4 in pshuttle26, including the identity and locations for restriction sites used to insert transgenes on both sides of the bidirectional promoter construct. P: promoter, Enh: enhancer, I: intron, TG: transgene, pA: polyadenylation signal, derived from SV40 (right side) or bovine growth hormone (BGH) (left side). Representation in plasmid vector pshuttle26. The same bidirectional expression cassette organization was used in pAdapt35. (B) Schematic representation of hCMV-CAG4 bidirectional promoter including the nucleotide positions of the building blocks. The arrows represent the direction of transcription.

Figure 4:
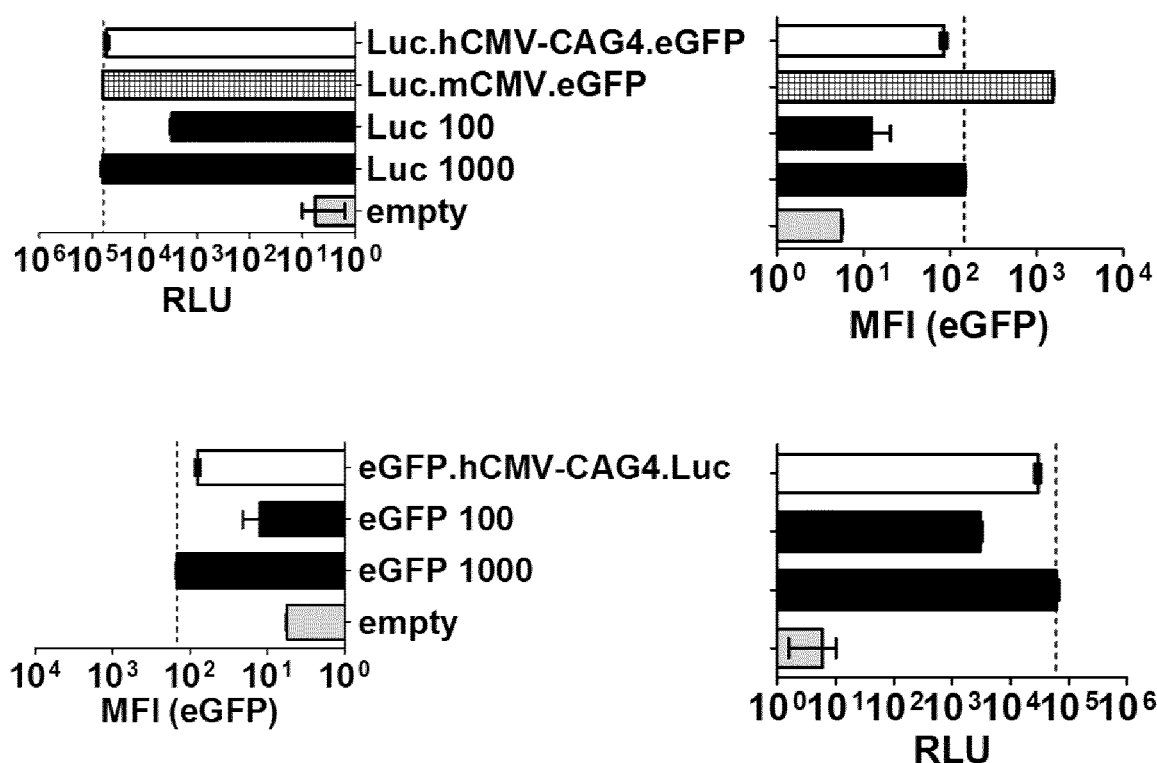

FIG. 4: Expression of Luciferase and eGFP transgenes on either the left or right side of bidirectional promoter constructs in Ad26 rAd vectors (A) and Ad35 rAd vectors (B) with infections in A549 cells at 1000 VP/cell. Luciferase expression is measured as relative light units (RLU) and eGFP expression is measured as mean fluorescence intensity (MFI) by FACS. Results for the different hCMV-CAG4 bidirectional promoter constructs are compared to positive controls of 100 VP/cell and 1000 VP/cell for Luciferase or eGFP under control of a unidirectional hCMV promoter and to cells infected with an empty vector. For Ad26 rAd vectors, hCMV-CAG4 is additionally compared to the bidirectional mCMV promoter.

Figure 5:
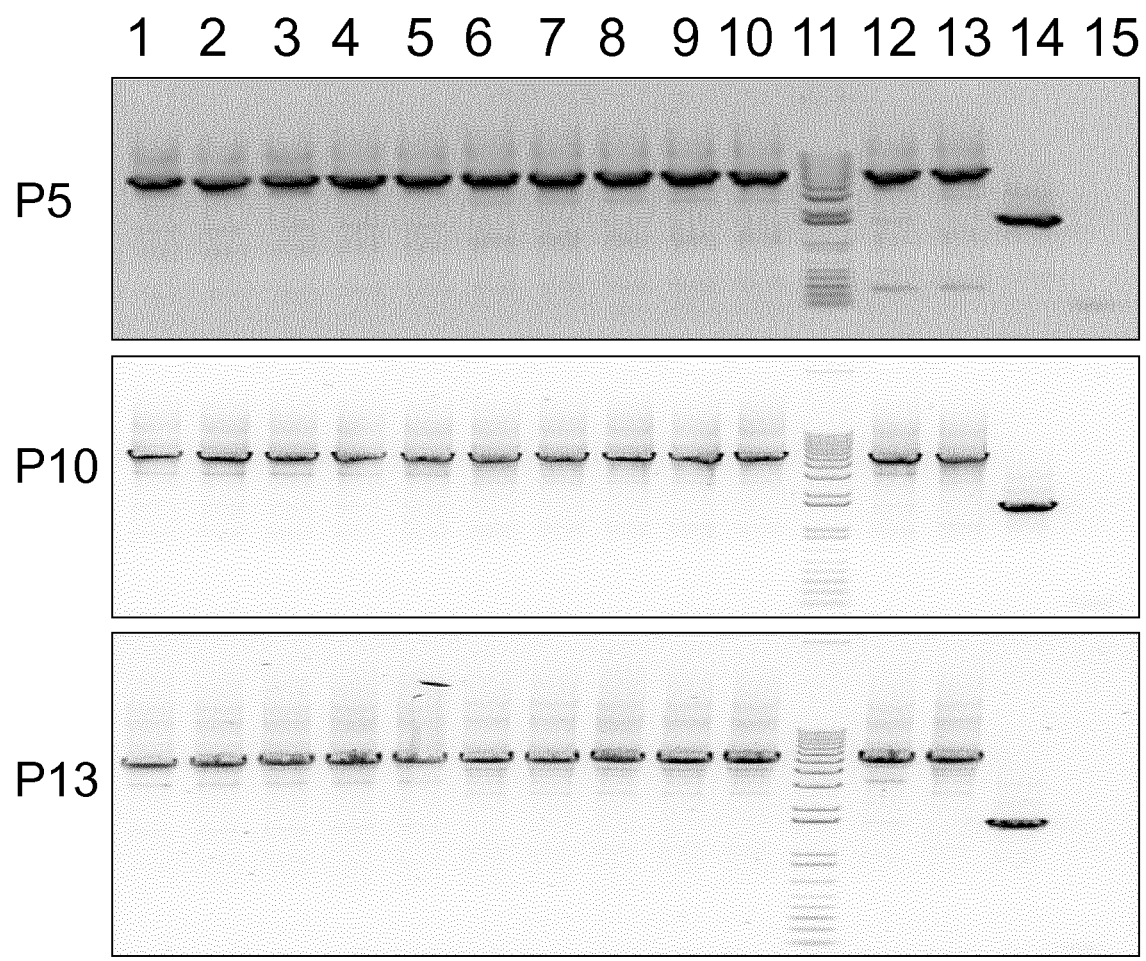

FIG. 5: Genetic stability testing by serial propagation followed by PCR on Ad26 vector genome harboring the bidirectional hCMV-CAG4 promoter in the E1 region and encoding eGFP and Luciferase on either the right or left side of the bidirectional hCMV-CAG4 promoter. Shown in the panels from top to bottom are PCR products for 5 plaques per vector after serial propagation in PER.C6 cells at P5, P10, and P13. Lanes 1-5 in each panel show the bidirectional hCMV-CAG4 promoter with Luciferase on the left and eGFP on the right. Lanes 6-10 in each panel show the bidirectional hCMV-CAG4 promoter with eGFP on the left and luciferase on the right. Lane 11 shows the kB marker. Lane 12 shows the plasmid positive control for Ad26.Luc.hCMV-CAG4.eGFP. Lane 13 shows the plasmid positive control for rAd26.eGFP.hCMV-CAG4.Luc. Lane 14 shows the plasmid control of the PCR product size of an expression cassette without transgene. Lane 15 shows the negative water PCR control. Labelling: P5, P10, P13: viral passage number, Additional bands besides the expected PCR products are unspecific PCR products caused by the GC-rich promoter sequence of the AG promoter part, Note: Absence of deletion bands was confirmed on overexposed pictures.

DETAILED DESCRIPTION OF THE INVENTION

Described herein are experimental results comparing new bidirectional promoter constructs for potency and balance. The results show that the bidirectional hCMV-CAG4 promoter provides potent and balanced expression of two transgenes, based on transient transfection with pAdApt plasmid vectors in HEK293 cells and viral infections with rAd26 and rAd35 comprising the bidirectional hCMV-CAG4 promoter with a first transgene operably linked to the bidirectional hCMV-CAG4 promoter in one direction and a second transgene operably linked to the bidirectional hCMV-CAG4 promoter in the other direction. Furthermore, rAd with the bidirectional hCMV-CAG4 promoter are genetically stable, with no deletion bands detected by PCR analysis up to passage 13 (p13), thus providing genetic stability that is comparable to viruses with only a single transgene. Thus, the rAd of the present invention with the bidirectional hCMV-CAG4 promoter are suitable for use in gene therapy and vaccine applications where balanced and potent expression are a priority.

The present invention therefore relates to recombinant nucleic acid molecules comprising a bidirectional hCMV-CAG4 promoter operably linked to a first transgene in one direction and to a second transgene in the opposite direction, wherein the transcriptional direction (5' to 3') of the hCMV and CAG portions of the hCMV-CAG4 bidirectional promoter point away from each other, and wherein expression from the left side is controlled by the hCMV portion of the bidirectional promoter and expression from the right side is controlled by the CAG portion of the bidirectional promoter. In certain embodiments, the invention relates to using vectors, viral vectors, and viruses comprising the bidirectional hCMV-CAG4 promoter for expressing two transgenes in a cell.

In certain embodiments, the invention relates to plasmid vectors for use in enabling host cells to produce heterologous proteins. For example, plasmid vectors comprising the bidirectional hCMV-CAG4 promoter could be used for expressing two different components of a heteromeric multi-subunit protein complex. Such plasmid vectors could be DNA sequences containing, for example, (1) the bidirectional hCMV-CAG4 promoter; (2) sequences providing mRNA with a ribosome binding site for each transgene; (3) a coding region for each transgene, i.e., a sequence of nucleotides which codes for the desired polypeptide; (4) a Kozak consensus sequence for each transgene for initiation of translation; (5) a termination sequence for each transgene which permits translation to be terminated when the entire code for each transgene has been read; and (6) if the vector is not directly inserted into the genome, an origin of replication which permits the entire vector to be reproduced once it is within the cell. It then remains to induce the host cell to incorporate the vector, for example by transfection or electroporation, and to grow the host cells in such a way as to express the two transgenes as part of the host cell's function.

In certain embodiments, the invention relates to rAd and rAd vectors comprising the bidirectional hCMV-CAG4 promoter and methods of making and using the rAd and rAd vectors, wherein the rAd and rAd vectors comprise a bidirectional hCMV-CAG4 promoter and two transgenes, wherein a first transgene is operably linked to the bidirectional hCMV-CAG4 promoter in one direction and a second transgene is operably linked to the bidirectional hCMV-CAG4 promoter in the other direction.

The rAd of the present invention can be produced in large amounts, or batches. A 'batch' of rAd is a composition that has been produced in one production run in a single production vessel, or alternatively it can refer to the plurality of rAd particles in a composition that is present in a single container (e.g., bioreactor, bag, flask, bottle, multi-dose vial, single-dose vial, syringe, etc). A batch of rAd according to the invention or a composition comprising rAd according to the invention preferably comprises at least $10^7$ rAd particles, and in certain embodiments comprises at least $10^8$, $10^9$, $10^{10}$, $10^{11}$, $10^{12}$, $10^{13}$, $10^{14}$, $10^{15}$, $10^{16}$, $10^{17}$, $10^{18}$, or more rAd particles, up to $10^{20}$ rAd particles (e.g. as produced in a large scale bioreactor in a single production run). A batch or composition may or may not comprise further relevant components besides the rAd.

The term 'recombinant' for a recombinant adenovirus, as used herein implicates that it has been modified by the hand of man as opposed to wild-type adenoviruses, e.g. it comprises a heterologous gene, genes, or parts thereof and a bidirectional hCMV-CAG4 promoter.

Sequences herein are provided in the 5' to 3' direction, as is customary in the art.

An "adenovirus capsid protein" refers to a protein on the capsid of an adenovirus that is involved in determining the serotype and/or tropism of a particular adenovirus. Adenoviral capsid proteins typically include the fiber, penton and/or hexon proteins. A rAd of (or 'based upon') a certain serotype according to the invention typically comprises fiber, penton and/or hexon proteins of that certain serotype, and preferably comprises fiber, penton and hexon protein of that certain serotype. These proteins are typically encoded by the genome of the rAd. A rAd of a certain serotype may optionally comprise and/or encode other proteins from other adenovirus serotypes.

A rAd is 'based upon' an adenovirus as used herein, by derivation from the wild type, at least in sequence. This can be accomplished by molecular cloning, using the wild type genome or parts thereof as starting material. It is also possible to use the known sequence of a wild type adenovirus genome to generate (parts of) the genome de novo by DNA synthesis, which can be performed using routine procedures by service companies having business in the field of DNA synthesis and/or molecular cloning (e.g. GeneArt, GenScripts, Invitrogen, Eurofins). Thus, as a non-limiting example, a rAd that comprises hexon, penton and fiber of Ad35 is considered a rAd based upon Ad35, etc.

The adenoviral vectors of the present invention are referred to as rAd vectors. The preparation of rAd vectors is well known in the art.

In certain embodiments, a rAd vector according to the invention is deficient in at least one essential gene function of the E1 region, e.g. the E1a region and/or the E1b region, of the adenoviral genome that is required for viral replication. In certain embodiments, an adenoviral vector according to the invention is deficient in at least part of the non-essential E3 region. In certain embodiments, the vector is deficient in at least one essential gene function of the E1 region and at least part of the non-essential E3 region. The adenoviral vector can be "multiply deficient," meaning that the adenoviral vector is deficient in one or more essential gene functions in each of two or more regions of the adenoviral genome. For example, the aforementioned E1-deficient or E1-, E3-deficient adenoviral vectors can be further deficient in at least one essential gene of the E4 region and/or at least one essential gene of the E2 region (e.g., the E2A region and/or E2B region).

Adenoviral vectors, methods for construction thereof and methods for propagating thereof, are well known in the art and are described in, for example, U.S. Pat. Nos. 5,559,099, 5,837,511, 5,846,782, 5,851,806, 5,994,106, 5,994,128, 5,965,541, 5,981,225, 6,040,174, 6,020,191, 6,113,913, and 8,932,607, and Thomas Shenk, "Adenoviridae and their Replication" M. S. Horowitz, "Adenoviruses", Chapters 67 and 68, respectively, in *Virology*, B. N. Fields et al., eds., 3d ed., Raven Press, Ltd., New York (1996), and other references mentioned herein. Typically, construction of adenoviral vectors involves the use of standard molecular biological techniques that are well known in the art, such as those described in, for example, Sambrook et al., *Molecular Cloning, a Laboratory Manual*, 2d ed., Cold Spring Harbor Press, Cold Spring Harbor, N.Y. (1989), Watson et al., *Recombinant DNA*, 2d ed., Scientific American Books (1992), and Ausubel et al., *Current Protocols in Molecular Biology*, Wiley Interscience Publishers, NY (1995), and other references mentioned herein.

An adenovirus according to the invention belongs to the family of the Adenoviridae and preferably is one that belongs to the genus Mastadenovirus. It can be a human adenovirus, but also an adenovirus that infects other species, including but not limited to a bovine adenovirus (e.g. bovine adenovirus 3, BAdV3), a canine adenovirus (e.g. CAdV2), a porcine adenovirus (e.g. PAdV3 or 5), or a simian adenovirus (which includes a monkey adenovirus and an ape adenovirus, such as a chimpanzee adenovirus or a gorilla adenovirus). Preferably, the adenovirus is a human adenovirus (HAdV, or AdHu; in the present invention a human adenovirus is meant if referred to Ad without indication of species, e.g. the brief notation "Ad5" means the same as HAdV5, which is human adenovirus serotype 5), or a simian adenovirus such as chimpanzee or gorilla adenovirus (ChAd, AdCh, or SAdV).

Most advanced studies have been performed using human adenoviruses, and human adenoviruses are preferred according to certain aspects of the invention. In certain preferred embodiments, the recombinant adenovirus according to the invention is based upon a human adenovirus. In preferred embodiments, the recombinant adenovirus is based upon a human adenovirus serotype 5, 11, 26, 34, 35, 48, 49 or 50. According to a particularly preferred embodiment of the invention, an adenovirus is a human adenovirus of one of the serotypes 26 and 35. An advantage of these serotypes is a low seroprevalence and/or low pre-existing neutralizing antibody titers in the human population. Preparation of rAd26 vectors is described, for example, in WO 2007/104792 and in (Abbink et al., 2007). Exemplary genome sequences of Ad26 are found in GenBank Accession EF 153474 and in SEQ ID NO:1 of WO 2007/104792. Preparation of rAd35 vectors is described, for example, in U.S. Pat. No. 7,270,811, in WO 00/70071, and in (Vogels et al., 2003). Exemplary genome sequences of Ad35 are found in GenBank Accession AC_000019 and in FIG. 6 of WO 00/70071.

Simian adenoviruses generally also have a low seroprevalence and/or low pre-existing neutralizing antibody titers in the human population, and a significant amount of work has been reported using chimpanzee adenovirus vectors (e.g. U.S. Pat. No. 6,083,716; and WO 2005/071093; WO 2010/086189; and WO 2010085984; (Bangari & Mittal, 2006; Cohen et al., 2002; Farina et al., 2001; Kobinger et al., 2006; Lasaro & Ertl, 2009; Tatsis et al., 2007). Hence, in other preferred embodiments, the recombinant adenovirus according to the invention is based upon a simian adenovirus, e.g. a chimpanzee adenovirus. In certain embodiments, the recombinant adenovirus is based upon simian adenovirus type 1, 7, 8, 21, 22, 23, 24, 25, 26, 27.1, 28.1, 29, 30, 31.1, 32, 33, 34, 35.1, 36, 37.2, 39, 40.1, 41.1, 42.1, 43, 44, 45, 46, 48, 49, 50 or SA7P. Also rhesus monkey adenovirus vectors have been described as useful candidate vectors (e.g. (Abbink et al., 2015); WO 2014/078688). Hence, in other preferred embodiments, the recombinant adenovirus of the invention is based upon a rhesus monkey adenovirus, for instance on one of the non-limiting examples RhAd51, RhAd52 or RhAd53 (or sAd4287, sAd4310A or sAd4312; see e.g. (Abbink et al., 2015) and WO 2014/078688).

In addition to adenoviruses, those skilled in the art will recognize that other viruses are also suitable for use as viral vectors using the bidirectional promoters of the present invention. For example, adeno-associated viruses (AAV), herpes simplex virus (HSV), poxvirus and lentivirus can also be engineered to include the bidirectional promoters of the present invention. See, for example, reviews about different vectors as discussed in (Heilbronn & Weger, 2010; Robbins & Ghivizzani, 1998; Walther & Stein, 2000).

The sequences of most of the human and non-human adenoviruses mentioned above are known, and for others can be obtained using routine procedures.

A recombinant adenovirus according to the invention may be replication-competent or replication-deficient.

In certain embodiments, the adenovirus is replication deficient, e.g. because it contains a deletion in the E1 region of the genome. A "deletion in the E1 region" means a deletion in this region as compared to a wild-type adenovirus, and means a deletion in at least one of the E1A, E1B 55K or E1B 21K coding regions, preferably a deletion of E1A, E1B 55K and E1B21K coding regions. As known to the skilled person, in case of deletions of essential regions from the adenovirus genome, the functions encoded by these regions have to be provided in trans, preferably by the producer cell, i.e. when parts or whole of E1, E2 and/or E4 regions are deleted from the adenovirus, these have to be present in the producer cell, for instance integrated in the genome thereof, or in the form of so-called helper adenovirus or helper plasmids. The adenovirus may also have a deletion in the E3 region, which is dispensable for replication, and hence such a deletion does not have to be complemented.

A producer cell (sometimes also referred to in the art and herein as 'packaging cell' or 'complementing cell' or 'host cell') that can be used can be any producer cell wherein a desired adenovirus can be propagated. For example, the propagation of recombinant adenovirus vectors is done in producer cells that complement deficiencies in the adenovirus. Such producer cells preferably have in their genome at least an adenovirus E1 sequence, and thereby are capable of complementing recombinant adenoviruses with a deletion in the E1 region. Any E1-complementing producer cell can be used, such as human retina cells immortalized by E1, e.g. 911 or PER.C6 cells (see, e.g., U.S. Pat. No. 5,994,128), E1-transformed amniocytes (See, e.g., EP 1230354), E1-transformed A549 cells (see e.g. WO 98/39411, U.S. Pat. No. 5,891,690), GH329:HeLa cells (Gao, Engdahl, & Wilson, 2000), 293 cells, and the like. In certain embodiments, the producer cells are for instance HEK293 cells, or PER.C6 cells, or 911 cells, or IT293SF cells, and the like.

For E1-deficient adenoviruses that are not derived from subgroup C or E adenoviruses, it is preferred to exchange the E4-orf6 coding sequence of the non-subgroup C or E adenovirus with the E4-orf6 of an adenovirus of subgroup C such as Ad5. This allows propagation of such adenoviruses in well-known complementing cell lines that express the E1 genes of Ad5, such as for example 293 cells or PER.C6 cells (see, e.g. (Havenga et al., 2006); WO 03/104467, incorporated in its entirety by reference herein).

In alternative embodiments, there is no need to place a heterologous E4orf6 region (e.g. of Ad5) in the adenoviral vector, but instead the E1-deficient non-subgroup C or E vector is propagated in a cell line that expresses both E1 and a compatible E4orf6, e.g. the 293-ORF6 cell line that expresses both E1 and E4orf6 from Ad5 (see e.g. (Brough, Lizonova, Hsu, Kulesa, & Kovesdi, 1996) describing the generation of the 293-ORF6 cells; (Abrahamsen et al., 1997; Nan et al., 2003) each describing generation of E1 deleted non-subgroup C adenoviral vectors using such a cell line).

Alternatively, a complementing cell that expresses E1 from the serotype that is to be propagated can be used (see e.g. WO 00/70071, WO 02/40665).

For subgroup B adenoviruses, such as Ad35, having a deletion in the E1 region, it is preferred to retain the 3' end of the E1B 55K open reading frame in the adenovirus, for instance the 166 bp directly upstream of the pIX open reading frame or a fragment comprising this such as a 243 bp fragment directly upstream of the pIX start codon (marked at the 5' end by a Bsu36I restriction site in the Ad35 genome), since this increases the stability of the adenovirus because the promoter of the pIX gene is partly residing in this area (see, e.g. (Havenga et al., 2006); Int'l. Pat. App. Pub. No. WO 2004/001032, incorporated by reference herein).

"Heterologous nucleic acid" (also referred to herein as 'transgene') in vectors or (adeno)viruses of the invention is nucleic acid that is not naturally present in the vector or (adeno)virus. It is introduced into the vector or (adeno)virus for instance by standard molecular biology techniques. It may in certain embodiments encode a protein of interest or part thereof. It can for instance be cloned into a deleted E1 or E3 region of an adenoviral vector. In preferred embodiments of the invention, the expression cassette with the two transgenes under control of the bidirectional hCMV-CAG4 promoter is placed into the E1 region of the adenoviral genome. A transgene is generally operably linked to expression control sequences. This can for instance be done by placing the nucleic acid encoding the transgene(s) under the control of a promoter. Many promoters can be used for expression of a transgene(s), and are known to the skilled person.

As used herein, the terms "promoter" or "promoter region" or "promoter element" are used interchangeably, and refer to a segment of a nucleic acid sequence, typically but not limited to DNA, that controls the transcription of the nucleic acid sequence to which it is operatively linked. The promoter region includes specific sequences that are sufficient for RNA polymerase recognition, binding and transcription initiation. In addition, the promoter region can optionally include sequences which modulate this recognition, binding and transcription initiation activity of RNA polymerase. These sequences may be cis-acting or may be responsive to trans-acting factors. Furthermore, the promoters may be constitutive or regulated, depending upon the nature of the regulation.

The skilled person will be aware that promoters are built from stretches of nucleic acid sequences and often comprise elements or functional units in those stretches of nucleic acid sequences, such as a transcription start site, a binding site for RNA polymerase, general transcription factor binding sites, such as a TATA box, specific transcription factor binding sites, and the like. Further regulatory sequences may be present as well, such as enhancers, and sometimes introns at the end of a promoter sequence. Such functional units are referred to herein below as 'building blocks', and they may be combined in a stretch of nucleic acid to build a functional promoter sequence. The building blocks may be directly adjacent to each other but may also be separated by stretches of nucleic acid that do not have a direct role in the promoter function. The skilled person knows how to test whether nucleotides in the stretch of nucleic acid are relevant for promoter function, and to how to remove or add building blocks and/or nucleotides into a given promoter sequence by standard molecular biology methods, e.g. to minimize its length while retaining promoter activity or to optimize activity.

As used herein, the terms "enhancer" or "enhancer building block" refer to regulatory DNA sequences, e.g., 50-1500 bp, that can be bound by proteins (activator proteins) to stimulate or enhance transcription of a gene or several genes. These activator proteins, (a.k.a., transcription factors) interact with the mediator complex and recruit polymerase II and the general transcription factors which then begin transcribing the genes. Enhancers are generally cis-acting, but can be located either upstream or downstream from the start site of the gene or genes they regulate. Furthermore, an enhancer can be either in the forward or backward direction and doesn't need to be located near the transcription initiation site to affect transcription, as some have been found located several hundred thousand base pairs upstream or downstream of the start site. Enhancers can also be found within introns.

The term "bidirectional promoter" refers to continuous gene regulatory sequences that may contain enhancer elements and intron elements besides the promoter elements and are defined by the building blocks as described herein. These bidirectional promoters direct gene expression in a bidirectional fashion controlling expression for transgenes placed on both sides of the bidirectional promoter sequence. For example, the bidirectional promoter of the present invention directs transcription of two different transgenes in a bidirectional fashion and includes an enhancer building block flanked by a first promoter building block on one side and a second promoter building block on the other side, with intron building blocks located at each end of the bidirectional promoter and adjacent to the promoter building blocks, such that the introns are downstream of the respective promoters and upstream of the respective transgenes. Note that flanked and adjacent do not necessarily mean directly contiguous as there might be some additional nucleotides in between the building blocks, but preferably not too much additional sequence is added so that the bidirectional promoter maintains a compact size. Also note that the terms 'upstream' and 'downstream' are with respect to the direction of transcription as commonly used in the art. For example, by convention the terms upstream and downstream relate to the 5' to 3' direction in which RNA transcription takes place. Upstream is toward the 5' end of the RNA molecule and downstream is toward the 3' end. When considering double-stranded DNA, upstream is toward the 5' end of the coding strand for the gene in question and downstream is toward the 3' end. Due to the anti-parallel nature of DNA, this means the 3' end of the template strand is upstream of the gene and the 5' end is downstream. See, for example, FIG. 1D, shows a preferred bidirectional hCMV-CAG4 promoter comprising a cytomegalovirus major immediate early enhancer (hCMV enhancer) as an enhancer building block flanked by a cytomegalovirus major immediate early promoter (hCMV promoter) as a first promoter building block and a chicken beta actin promoter as a second promoter building block, with a hybrid chicken beta actin/rabbit beta globin intron as a first intron building block adjacent to and downstream of the chicken beta actin promoter (chicken beta actin promoter and hybrid intron together referred to as 'CAG' promoter portion) and a human apolipoprotein A-1 intron (hApoA1intron) as a second intron building block adjacent to and downstream of the hCMV promoter building block. The bidirectional hCMV-CAG4 promoter of the present invention is operably linked to two transgenes, such that a first transgene is operably linked to the hCMV promoter building block, and a second transgene is operably linked to the CAG promoter, such that the first and second transgenes each are located downstream of the respective promoter and intron pair and such that the first and second transgenes are transcribed in a direction outward from the hCMV enhancer.

A preferred bidirectional promoter of the present invention is the bidirectional hCMV-CAG4 promoter comprising SEQ ID NO:4, with the sequence locations for the different elements as indicated in FIG. 3B, but a person skilled in the art will recognize that the length of or identity in the sequences of the different building blocks and the intervening sequences could be varied to some degree such that essentially similar results could be obtained. For example, (Richardson et al., 2009) showed that the intron in the 5' untranslated region (UTR) of the CAG promoter can be truncated to accommodate larger inserts and the CAG promoter with the truncated intron provided increased expression. That truncated version of the hybrid chicken beta actin/rabbit beta globin intron was used here in the bidirectional hCMV-CAG4 promoter. (Quilici et al., 2013) also showed that deletions in intron A of the hCMV promoter enhanced expression. Thus, a person skilled in the art could tweak the intron sequences and/or intervening sequences of the bidirectional hCMV-CAG4 promoter such that essentially similar results could be obtained. Similarly, different enhancers could be tested for substitution and/or the enhancer sequences could be tweaked such that essentially similar expression could be obtained. Likewise, the hApoA1 intron could be replaced by other introns, and it is expected that the bidirectional promoter would still be active. The enhancers and introns indicated herein are preferred, being of suitable sizes, giving rise to balanced expression, and stable constructs in an adenoviral vector context. The building blocks of the bidirectional promoter of the invention as such may have been individually known, but were never combined nor even suggested to be combined in the constellation of the invention, which results in a strong, balanced, bidirectional promoter. As shown herein, this combination was surprisingly found to be capable of directing transcription of the two operably linked transgenes each to an extent similar as compared to a strong unidirectional hCMV promoter, while at the same time remaining a stable configuration of the bidirectional promoter with associated transgenes in the complex context of an adenoviral vector. Data presented herein show that creating such bidirectional promoters based upon known similar building blocks was unpredictable, in that several other similarly designed bidirectional promoters either lacked strong promoter activity, and/or led to unbalanced expression whereby expression of the transgene operably linked to one part of a bidirectional promoter was expressed significantly stronger (e.g. at least 5× difference) compared to the transgene operably linked to the other part of such a bidirectional promoter. It was a priori not predictable whether any promoter that would meet the requirements of similar expression levels from both sides (e.g. less than 2× difference between expression from both sides) and stability in the context of adenoviral vectors, would be achievable at all. The present invention surprisingly provides bidirectional promoters that meet these requirements.

Further regulatory sequences may also be added to constructs comprising the bidirectional promoters of the present invention. The term "regulatory sequence" is used interchangeably with "regulatory element" herein and refers to a segment of nucleic acid, typically but not limited to DNA, that modulate the transcription of the nucleic acid sequence to which it is operatively linked, and thus acts as a transcriptional modulator. A regulatory sequence often comprises nucleic acid sequences that are transcription binding domains that are recognized by the nucleic acid-binding domains of transcriptional proteins and/or transcription factors, enhancers or repressors etc. For example, a regulatory sequence could include one or more tetracycline operon operator sequences (tetO), such that expression is inhibited in the presence of the tetracycline operon repressor protein (tetR). In the absence of tetracycline, the tetR protein is able to bind to the tetO sites and repress transcription of a gene operably linked to the tetO sites. In the presence of tetracycline, however, a conformational change in the tetR protein prevents it from binding to the operator sequences, allowing transcription of operably linked genes to occur. In certain embodiments, rAd of the present invention can optionally include tetO operatively linked to the bidirectional hCMV-CAG4 promoter, such that expression of one or more transgenes is inhibited in the vectors that are produced in the producer cell line in which tetR protein is expressed. Subsequently, expression would not be inhibited if the vector is introduced into a subject or into cells that do not express the tetR protein (see e.g., WO 07/073513). In certain other embodiments, vector of the present invention can optionally include a cumate gene-switch system, in which regulation of expression is mediated by the binding of the repressor (CymR) to the operator site (CuO), placed downstream of the promoter (see e.g., (Mullick et al., 2006)).

As used herein, the term "repressor," refers to entities (e.g., proteins or other molecules) having the capacity to inhibit, interfere, retard and/or repress the production of heterologous protein product of a recombinant expression vector. For example, by interfering with a binding site at an appropriate location along the expression vector, such as in an expression cassette. Examples of repressors include tetR, CymR, the lac repressor, the trp repressor, the gal repressor, the lambda repressor, and other appropriate repressors known in the art.

Furthermore, a recombinant vector, virus or adenovirus of the present invention comprises a bidirectional hCMV-CAG4 promoter, wherein the transcriptional direction (5' to 3') of the hCMV and CAG portions of the hCMV-CAG4 bidirectional promoter point away from each other, and wherein the hCMV-CAG4 bidirectional promoter is operably linked to a first transgene in one direction and to a second transgene in the opposite direction. The bidirectional promoter thus will drive expression of the first transgene towards a first end of the vector or (adeno)viral genome and of the second transgene towards the other end of the vector or (adeno)viral genome. The skilled person will be aware that mutations can be made in the provided sequences and can be tested for promoter activity by routine methods. Typically, a sequence having at least 90% identity with the indicated promoter sequences (not including the enhancer and intron sequences) will still have functional activity and hence will be considered a bidirectional hCMV-CAG4 promoter. Thus, the bidirectional hCMV-CAG4 promoter of the present invention preferably has at least 90%, 91%, 92%, 93%, 94%, 95%, 96%, 97%, 98%, or 99% identity to the indicated promoter sequences (outside the enhancer and intron sequences). Preferably, the bidirectional hCMV-CAG4 promoter comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 4. In certain preferred embodiments, the bidirectional hCMV-CAG4 promoter contains the building blocks as shown in FIG. 1D, wherein the bidirectional hCMV-CAG4 promoter comprises an hCMV enhancer as an enhancer building block flanked by an hCMV promoter as a first promoter building block and a chicken beta actin promoter as a second promoter building block, with a hybrid chicken beta actin/rabbit beta globin intron as a first intron building block adjacent to the chicken beta actin promoter and an hApoA1intron as a second intron building block adjacent to the hCMV promoter building block. In a certain other preferred embodiment the bidirectional hCMV-CAG4 promoter is 100% identical to SEQ ID NO:4, with the sequence locations for the different elements as indicated in FIG. 3, but a person skilled in the art will recognize that the length of the sequences of the different building blocks and the intervening sequences could be varied to some degree and the identity of the enhancer and intron elements could also be varied such that essentially similar results could be obtained.

The terms "operably linked", or "operatively linked" are used interchangeably herein, and refer to the functional relationship of the nucleic acid sequences with regulatory sequences of nucleotides, such as promoters, enhancers, transcriptional and translational stop sites, and other signal sequences and indicates that two or more DNA segments are joined together such that they function in concert for their intended purposes. For example, operative linkage of nucleic acid sequences, typically DNA, to a regulatory sequence or promoter region refers to the physical and functional relationship between the DNA and the regulatory sequence or promoter such that the transcription of such DNA is initiated from the regulatory sequence or promoter, by an RNA polymerase that specifically recognizes, binds and transcribes the DNA. In order to optimize expression and/or in vitro transcription, it may be necessary to modify the regulatory sequence for the expression of the nucleic acid or DNA in the cell type for which it is expressed. The desirability of, or need of, such modification may be empirically determined.

The expression controlled by either part of the bidirectional hCMV-CAG4 promoter the transgene is potently expressed. As used herein, "potently expressed" or "potent expression" mean that the expression from either part of the bidirectional hCMV-CAG4 promoter, as measured for example by different protein detection techniques such as Western Blot, FACS analysis, or other assays using luminescence or fluorescence, is comparable to or even better than expression from a monovalent vector expressing a single transgene under the control of an hCMV promoter. The hCMV promoters are derived from the major immediate early (mIE) region of human cytomegalovirus and are frequently used for potent unidirectional gene expression in vaccine and gene therapy vectors. For example, a hCMV promoter sequence can be derived from the hCMV AD 169 strain mIE locus (X03922) and include NF 1 binding sites, the enhancer region, TATA box and part of the first exon Other hCMV promoter sequences are known which can be shorter (e.g. only containing the enhancer and promoter region and lacking NF1 binding sites) or longer (e.g. including additional cellular factor binding sites and the first intron sequence). These hCMV promoters which differ in length were all found to be potent ubiquitously active promoters. For the comparisons of expression levels as described herein, the hCMV promoter sequence was SEQ ID NO:9. For example, the expression level from either part of the bidirectional hCMV-CAG4 promoter of the present invention in a rAd is preferably at least 50%, 60%, 70%, 80%, 90%, or 95% of the expression level from a monovalent rAd with an hCMV promoter of SEQ ID NO:9. In certain embodiments, the expression level from either part of the bidirectional hCMV-CAG4 promoter is about 100% of the expression level from a monovalent rAd with an hCMV promoter of SEQ ID NO:9. Furthermore, it is known from rAd expressing a single antigen under the control of an hCMV promoter that the expression is sufficient to generate significant T-cell and B-cell immune responses. Therefore, potent expression of two transgenes expressed by a bidirectional hCMV-CAG4 promoter of the present invention is expected to generate a significant T-cell and B-cell immune response to both transgenes. For example, if the two transgenes encode antigens to elicit an immune response when administered to a subject, potent expression will generate a measurable immune response against both antigens and that immune response to both antigens will preferably be the same or better than the immune response generated by a corresponding monovalent vector or rAd expressing a single antigen under the control of an hCMV promoter.

The expression is balanced from both sides of the bidirectional hCMV-CAG4 promoter. As used herein, "balanced expression", "balance of expression", "expression balance", or "balanced" as it refers to expression, mean that the expression from one side of the bidirectional promoter, as measured for example by different protein expression detection techniques such as Western Blot, FACS analysis, or other assays using luminescence or fluorescence, is comparable to the expression from the other side of the bidirectional promoter. For example, the expression level from one side of the bidirectional hCMV-CAG4 promoter of the present invention is preferably at least 50%, 60%, 70%, 80%, 90%, or 95% of the expression level from the other side of the bidirectional promoter. In certain embodiments, the expression level from one side of the bidirectional hCMV-CAG4 promoter is about 100% of the expression level from the other side of the bidirectional promoter. In another example, the ratio of the expression from the two sides of the bidirectional hCMV-CAG4 promoter is in the range of 1/1, 1.1/1, 1.2/1, 1.3/1, 1.4/1, 1.5/1, 1.6/1, 1.7/1, 1.8/1, 1.9/1, and 2/1. Furthermore, it is known from rAd expressing a single antigen under the control of an hCMV promoter that the expression is sufficient to generate significant T-cell and B-cell immune responses. Therefore, balanced expression of two antigens expressed by a bidirectional hCMV-CAG4 promoter of the present invention is expected to generate comparable T-cell and B-cell immune response to both antigens. For example, the immune response from the antigen expressed from one side of the hCMV-CAG4 promoter, is preferably at least 50%, 60%, 70%, 80%, 90%, or 95% of the of the immune response for the antigen expressed from the other side of the bidirectional promoter. In certain embodiments, the immune response to the antigen expressed from one side of the bidirectional hCMV-CAG4 promoter is about 100% of the immune response to the antigen expressed from the other side of the bidirectional promoter. Thus, the bidirectional hCMV-CAG4 promoter of the present invention is improved in balance of expression compared to the mCMV bidirectional promoter. There was approximately a 10-times higher expression of an antigen positioned at the right side (3'end) of the bidirectional mCMV promoter compared to the antigen positioned at the left side (5'end) of the bidirectional mCMV promoter (which was described in WO 2016/166088).

The terms "coding sequence", "sequence encoding", or "encoding" are used interchangeably herein, and refer to the nucleic acid sequence which is transcribed (DNA) and translated (mRNA) into a polypeptide in vitro or in vivo when operably linked to appropriate regulatory sequences.

A polyadenylation signal, for example the bovine growth hormone polyA signal (U.S. Pat. No. 5,122,458), may be present behind the transgenes. Preferably, each transgene has a polyA signal, and preferably the polyA signal for the first transgene is different from the polyA signal for the second transgene. In one embodiment, a first polyA signal is an SV40 polyA signal, and a second polyA signal is the bovine growth hormone polyA signal.

A sequence comprising an intron is present at both ends of the bidirectional promoter of the invention. These introns may be the same but preferably are different. An intron as used herein has the normal function and structure as known in the art, and is a polynucleotide sequence in a nucleic acid that does not encode information for protein synthesis and is removed before translation of messenger RNA, by a process known as splicing. An intron comprises a splice donor site (5'end of the intron, usually a GU sequence) and a splice acceptor site (3'end of the intron, usually a GA sequence). A variety of different introns can potentially be used according to the present invention, although it is preferred to use relatively short introns and introns modified to be shorter introns in order to not take up too much space in a viral vector so that more space remains for the transgenes in the recombinant adenovirus. It is preferred to use a first intron on one side of the bidirectional promoter and a second, different intron on the other side of the bidirectional promoter, i.e. each transgene is preceded by a different intron sequence. In certain embodiments, an intron could be a chimeric intron. The skilled person is aware that many different introns are available and can be used. It is known that introns can increase protein expression, in particular in vivo. In a particular preferred embodiment the promoter of the invention comprises a hybrid chicken beta actin/rabbit beta globin intron as a first intron that is adjacent to the chicken beta actin promoter building block. In one embodiment the promoter of the invention comprises an hApoA1intron as a second intron that is adjacent to the hCMV promoter building block. In particularly preferred embodiments, the promoter of the invention comprises a hybrid chicken beta actin/rabbit beta globin intron as a first intron that is adjacent to the chicken beta actin promoter building block, and an hApoA1intron as a second intron that is adjacent to the hCMV promoter building block.

One of the exemplified parameters in the experiments described herein is immunogenicity, which is relevant for antigens in a vaccine application. However, it will be immediately clear to the skilled person that balanced transgene expression levels can also be relevant for transgenes for which an immune response is not the primary goal, e.g. for two different transgenes that are used for gene therapy purposes, for expression of heterologous protein complexes, or for proportional expression of two antibody chains. Hence, the invention can be practiced with any combination of transgenes for which expression from a single recombinant vector, e.g. adenoviral vector, is desired. Therefore, the identity of the transgene is not material for the instant invention, which is suitable for example with vectors or adenoviruses comprising any transgene. Suitable transgenes are well known to the skilled person, and for instance may include transgene open reading frames, for instance open reading frames coding for polypeptides that have a therapeutic effect, e.g. for gene therapy purposes, or polypeptides against which an immune response is desired when the rAd vector is used for vaccination purposes. Particularly preferred heterologous nucleic acids are genes of interest encoding antigenic determinants towards which an immune response needs to be raised. Such antigenic determinants are also typically referred to as antigens. When the recombinant adenovirus is administered to a subject, an immune response will be raised against the antigen(s). Any desired antigen can be encoded by the adenovirus vector. In typical embodiments according to the invention, antigens are peptides, polypeptides or proteins from organisms that may cause a disease or condition. Therefore, in a further preferred embodiment, said heterologous nucleic acid of interest encodes an immunogenic (or antigenic) determinant. More preferably, said immunogenic determinant is an antigen from a bacterium, a virus, yeast or a parasite. The diseases caused by such organisms are generally referred to as 'infectious disease' (and are thus not limited to organisms that 'infect' but also include those that enter the host and cause a disease). So-called 'self-antigens', e.g. tumour antigens, also form part of the state of the art, and may be encoded by heterologous nucleic acids in the recombinant adenoviruses according to the present invention. Non-limiting examples from which the antigenic determinants (or antigens) are taken are malaria-causing organisms, such as *Plasmodium falciparum*, tuberculosis-causing organism such as *Mycobacterium tuberculosis*, yeasts, or viruses. In other preferred embodiments, antigens from viruses such as flaviviruses (e.g., West Nile Virus, Hepatitis C Virus, Japanese Encephalitis Virus, Dengue Virus), Ebola virus, Human Immunodeficiency Virus (HIV), and Marburg virus may be used in compositions according to the present invention. In one embodiment, said antigen is the CS protein or immunogenic part thereof from *P. falciparum* (for examples of adenovirus vectors encoding CS, see e.g. (Havenga et al., 2006; Ophorst et al., 2006); WO 2004/055187, all incorporated in their entirety by reference herein). In another embodiment, the antigenic determinant is a protein of one antigen-, or a fusion protein of several antigens from *M. tuberculosis*, such as the Ag85A, Ag85B and/or the TB10.4 proteins or immunogenic part(s) thereof (see for the construction and production of such TB vaccine viruses e.g. WO 2006/053871, incorporated by reference herein). In yet another embodiment, said antigenic determinant is a viral glycoprotein or immunogenic part thereof, such as GP from a filovirus, such as Ebola virus or Marburg virus (e.g. (Geisbert et al., 2011; Sullivan et al., 2006; Sullivan et al., 2003). In yet further embodiments, said immunogenic determinant is from an HIV protein such as gag, pol, env, nef, or variants thereof (for examples of adenovirus based HIV vaccines, see e.g. WO 2009/026183, WO 2010/096561, WO 2006/120034, WO 02/22080, WO 01/02607). In other embodiments, said antigenic determinant is a HA, NA, M, or NP protein, or immunogenic part of any of these, from influenza virus (e.g. (Hu et al., 2011; Zhou et al., 2010); review by (Vemula & Mittal, 2010)). In other embodiments, the antigenic determinant is a HA protein or immunogenic part thereof from a measles virus (e.g. WO 2004/037294). In other embodiments, the antigenic determinant is rabies virus glycoprotein (e.g. (Zhou, Cun, Li, Xiang, & Ertl, 2006)). In further embodiments, the antigen is from a respiratory syncytial virus (RSV), e.g. RSV F protein (see e.g. WO 2013/139911 and WO 2013/139916), or RSV G protein, or both, or other RSV proteins. In other embodiments, the antigen is from another virus such as human papillomavirus or other viruses, etc. The recombinant adenovirus may encode two different antigens from the same organism. The recombinant adenovirus may also encode combinations of antigens from different organisms, e.g. a first antigen from a first organism and second antigen from a second organism. It is also possible to encode an antigen and for instance an adjuvant into the same adenovirus, e.g. an antigen and a Toll-Like-Receptor (TLR) agonist, such as a TLR3 agonist, such as dsRNA or a mimetic thereof or the like (e.g. WO 2007/100908). In certain embodiments, the recombinant vector, e.g. recombinant adenovirus, encodes two different antigens, each under control of the bidirectional hCMV-CAG4 promoter. In other embodiments, the vector or recombinant (adeno)virus encodes an antigen and an immune modulator, each under control of the bidirectional hCMV-CAG4 promoter. In certain embodiments, further heterologous sequences or transgenes may be present in the vector or recombinant (adeno)virus, besides the first and second transgene that are under control of the bidirectional hCMV-CAG4 promoter.

The invention also provides a method for producing a genetically stable recombinant adenovirus comprising a first and a second transgene that each are potently expressed when the adenovirus infects a target cell, the method comprising: preparing a construct comprising a bidirectional hCMV-CAG4 promoter operably linked to a first transgene in one direction and to a second transgene in the opposite direction, and incorporating said construct into the genome of the recombinant adenovirus. The preparation of the construct as such encompasses the use of standard molecular cloning methods that are well known (see e.g. (Holterman et al., 2004; Lemckert et al., 2006; Vogels et al., 2003); Sambrook, Fritsch and Maniatis, Molecular Cloning: A Laboratory Manual, 2nd edition, 1989; Current Protocols in Molecular Biology, Ausubel F M, et al, eds, 1987; the series Methods in Enzymology (Academic Press, Inc.); PCR2: A Practical Approach, MacPherson M J, Hams B D, Taylor G R, eds, 1995), as known to the skilled person and routinely performed in the field of recombinant adenovirus technology, and exemplified herein. The bidirectional hCMV-CAG4 promoter has the features as described above, and can be obtained by routine methods. For convenience, the skilled person may manipulate the adenovirus genome by cloning into smaller fragments, e.g. a first part for the left part of the genome up to the E1 region for easy manipulation and introduction of the transgenes in plasmid form and a second, larger, part for the remainder of the genome that can upon recombination with the first part result in a complete adenovirus genome (see e.g. WO 99/55132).

The rAd of the present invention has the advantage that it can express two transgenes and remains genetically stable, unlike adenoviruses prepared by the various alternative approaches for expressing two transgenes that are provided in the prior art, while also providing balanced expression of the two transgenes driven by the bidirectional promoter. Thus, the bidirectional hCMV-CAG4 promoter solves the problem of genetic instability of adenoviruses that express two transgenes, and of imbalanced expression of the two transgenes.

To test genetic stability, rAd are rescued and propagated in an appropriate cell line, e.g., helper cell line PER.C6®. Viral DNA is isolated at certain passage numbers and the integrity of the rAd genome can be analyzed by one or more of the following: PCR analysis for presence of the transgene region or absence of deletion bands, restriction digests of the rAd genome for presence or absence of differences in restriction fragments, and/or sequencing of the rAd genome or of PCR-products of the rAd genome for presence or absence of mutations in the rAd sequences. With regard to the rAd of the present invention, "genetically stable" means that the nucleotide sequence does not change from the plasmids used for generation of the rAd to later production stages of the rAd, such that rAd expressing two transgenes has the same genetic stability as a comparable rAd with a single transgene (e.g., behind a hCMV promoter) as suitable for large scale batch productions. For example, PCR analysis using primers flanking the expression cassette does not show deletion fragments (bands) compared to earlier passage numbers of the rAd or the starting material and/or sequencing the PCR product of the E1, E3 and E4 regions confirms that the nucleotide sequence does not change. Preferably sequencing the region containing the expression cassette with the bidirectional promoter confirms that the nucleotide sequence does not change in the region containing the expression cassette.

Genetic stability is thoroughly assessed in this study compared to other testing methods such as test digestions on a single produced virus batch. Sensitivity of the assay is increased by the following means: several viral populations (plaques) are isolated and subjected to extended passaging. The extended passaging, combined with a PCR analysis using primers flanking the expression cassette allows for detection of a small proportion of deletion mutants in the rAd population which might be overlooked using other methods. Further, sequencing analysis is performed to exclude occurrence of point mutations, such as introduction of stop codons in the open reading frame of the transgene. More specifically, since viral mutations always present a chance event, one plaque may be stable whereas another one may present a deletion band. Therefore, to correctly assess genetic stability, several viral populations (plaques) need to be tested. In case a mutation occurs, which enables the vector to replicate more efficiently than the parental vector, this can lead to outgrowth of the mutant version, which is often only observed following extended passaging as described in this study. Preferably, the rAd of the present invention are genetically stable for at least up to 10 passages, and even more preferably for at least up to 13 passages in the test system used, such that the virus is sufficiently stable for large scale production campaigns. It was recently found that a recombinant adenovirus that has two transgenes that are under control of the bidirectional mCMV promoter is genetically stable, see e.g., WO 2016/166088. The instant application demonstrates that a recombinant adenovirus that has two transgenes that are under control of the bidirectional hCMV-CAG4 promoter of the invention are also genetically stable, and moreover have a more balanced expression of the two transgenes compared to the situation where they are under control of the bidirectional mCMV promoter.

The recombinant adenovirus produced according to the methods of the invention can be prepared according to the embodiments described above for the recombinant adenovirus.

The invention also provides a method for expressing at least two transgenes in a cell, the method comprising providing the cell with a vector or a recombinant virus, e.g. a recombinant adenovirus, according to the invention. Providing a cell with a recombinant adenovirus can be done via administration of the adenovirus to a subject, or via introduction (e.g. infection) of the adenovirus in vitro or ex vivo into a cell. In certain embodiments the invention provides a recombinant adenoviral vector for use in expressing at least two transgenes in a cell, e.g. by administering the recombinant adenovirus to a subject.

The invention also provides a method for inducing an immune response against at least two antigens, comprising administering to a subject a vector, e.g. a recombinant (adeno)virus according to the invention. The invention also provides a vector or a recombinant (adeno)virus according to the invention for use in inducing an immune response against at least two antigens.

The invention also provides a recombinant DNA molecule comprising the bidirectional hCMV-CAG4 promoter of the present invention or the genome of a recombinant adenovirus of the invention. The skilled person will be aware that this may also be a combination of at least two different recombinant DNA molecules that together can form the single recombinant DNA molecule of the invention. Such molecules are useful in manipulating the genome and creating novel recombinant adenoviruses. The genome encodes the proteins that are required for adenovirus replication and packaging in permissive cells.

The term 'about' for numerical values as used in the present disclosure means the value±10%.

Producer cells are cultured to increase cell and virus numbers and/or virus titers. Culturing a cell is done to enable it to metabolize, and/or grow and/or divide and/or produce virus of interest according to the invention. This can be accomplished by methods such as well-known to persons skilled in the art, and includes but is not limited to providing nutrients for the cell, for instance in the appropriate culture media. Suitable culture media are well known to the skilled person and can generally be obtained from commercial sources in large quantities, or custom-made according to standard protocols. Culturing can be done for instance in dishes, roller bottles or in bioreactors, using batch, fed-batch, continuous systems and the like. Suitable conditions for culturing cells are known (see e.g. Tissue Culture, Academic Press, Kruse and Paterson, editors (1973), and R. I. Freshney, Culture of animal cells: A manual of basic technique, fourth edition (Wiley-Liss Inc., 2000, ISBN 0-471-34889-9).

Typically, the adenovirus will be exposed to the appropriate producer cell in a culture, permitting uptake of the virus. Usually, the optimal agitation is between about 50 and 300 rpm, typically about 100-200, e.g. about 150, typical DO is 20-60%, e.g. 40%, the optimal pH is between 6.7 and 7.7, the optimal temperature between 30 and 39° C., e.g. 34-37° C., and the optimal MOI between 5 and 1000, e.g. about 50-300. Typically, adenovirus infects producer cells spontaneously, and bringing the producer cells into contact with rAd particles is sufficient for infection of the cells. Generally, an adenovirus seed stock is added to the culture to initiate infection, and subsequently the adenovirus propagates in the producer cells. This is all routine for the person skilled in the art.

After infection of an adenovirus, the virus replicates inside the cell and is thereby amplified, a process referred to herein as propagation of adenovirus. Adenovirus infection results finally in the lysis of the cells being infected. The lytic characteristics of adenovirus therefore permits two different modes of virus production. The first mode is harvesting virus prior to cell lysis, employing external factors to lyse the cells. The second mode is harvesting virus supernatant after (almost) complete cell lysis by the produced virus (see e.g. U.S. Pat. No. 6,485,958, describing the harvesting of adenovirus without lysis of the host cells by an external factor). It is preferred to employ external factors to actively lyse the cells for harvesting the adenovirus.

Methods that can be used for active cell lysis are known to the person skilled in the art, and have for instance been discussed in WO 98/22588, p. 28-35. Useful methods in this respect are for example, freeze-thaw, solid shear, hypertonic and/or hypotonic lysis, liquid shear, sonication, high pressure extrusion, detergent lysis, combinations of the above, and the like. In one embodiment of the invention, the cells are lysed using at least one detergent. Use of a detergent for lysis has the advantage that it is an easy method, and that it is easily scalable.

Detergents that can be used, and the way they are employed, are generally known to the person skilled in the art. Several examples are for instance discussed in WO 98/22588, p. 29-33. Detergents can include anionic, cationic, zwitterionic, and nonionic detergents. The concentration of the detergent may be varied, for instance within the range of about 0.1%-5% (w/w). In one embodiment, the detergent used is Triton X-100.

Nuclease may be employed to remove contaminating, i.e. mostly from the producer cell, nucleic acids. Exemplary nucleases suitable for use in the present invention include Benzonase®, Pulmozyme®, or any other DNase and/or RNase commonly used within the art. In preferred embodiments, the nuclease is Benzonase®, which rapidly hydrolyzes nucleic acids by hydrolyzing internal phosphodiester bonds between specific nucleotides, thereby reducing the viscosity of the cell lysate. Benzonase® can be commercially obtained from Merck KGaA (code W214950). The concentration in which the nuclease is employed is preferably within the range of 1-100 units/ml. Alternatively, or in addition to nuclease treatment, it is also possible to selectively precipitate host cell DNA away from adenovirus preparations during adenovirus purification, using selective precipitating agents such as domiphen bromide (see e.g. U.S. Pat. No. 7,326,555; (Goerke, To, Lee, Sagar, & Konz, 2005); WO 2011/045378; WO 2011/045381).

Methods for harvesting adenovirus from cultures of producer cells have been extensively described in WO 2005/080556.

In certain embodiments, the harvested adenovirus is further purified. Purification of the adenovirus can be performed in several steps comprising clarification, ultrafiltration, diafiltration or separation with chromatography as described in for instance WO 05/080556, incorporated by reference herein. Clarification may be done by a filtration step, removing cell debris and other impurities from the cell lysate. Ultrafiltration is used to concentrate the virus solution. Diafiltration, or buffer exchange, using ultrafilters is a way for removal and exchange of salts, sugars and the like. The person skilled in the art knows how to find the optimal conditions for each purification step. Also, WO 98/22588, incorporated in its entirety by reference herein, describes methods for the production and purification of adenoviral vectors. The methods comprise growing host cells, infecting the host cells with adenovirus, harvesting and lysing the host cells, concentrating the crude lysate, exchanging the buffer of the crude lysate, treating the lysate with nuclease, and further purifying the virus using chromatography.

Preferably, purification employs at least one chromatography step, as for instance discussed in WO 98/22588, p. 61-70. Many processes have been described for the further purification of adenoviruses, wherein chromatography steps are included in the process. The person skilled in the art will be aware of these processes, and can vary the exact way of employing chromatographic steps to optimize the process. It is for instance possible to purify adenoviruses by anion exchange chromatography steps, see for instance WO 2005/080556. Many other adenovirus purification methods have been described and are within the reach of the skilled person. Further methods for producing and purifying adenoviruses are disclosed in for example WO 00/32754, WO 04/020971, WO 2006/108707, and U.S. Pat. Nos. 5,837,520 and 6,261,823, all incorporated by reference herein.

For administering to humans, the invention may employ pharmaceutical compositions comprising the vector or recombinant virus, e.g., rAd, and a pharmaceutically acceptable carrier or excipient. In the present context, the term "Pharmaceutically acceptable" means that the carrier or excipient, at the dosages and concentrations employed, will not cause any unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). The purified rAd preferably is formulated and administered as a sterile solution although it is also possible to utilize lyophilized preparations. Sterile solutions are prepared by sterile filtration or by other methods known per se in the art. The solutions are then lyophilized or filled into pharmaceutical dosage containers. The pH of the solution generally is in the range of pH 3.0 to 9.5, e.g. pH 5.0 to 7.5. The rAd typically is in a solution having a suitable buffer, and the solution of rAd may also contain a salt. Optionally stabilizing agent may be present, such as albumin. In certain embodiments, detergent is added. In certain embodiments, rAd may be formulated into an injectable preparation. These formulations contain effective amounts of rAd, are either sterile liquid solutions, liquid suspensions or lyophilized versions and optionally contain stabilizers or excipients. An adenovirus vaccine can also be aerosolized for intranasal administration (see e.g. WO 2009/117134).

For instance adenovirus may be stored in the buffer that is also used for the Adenovirus World Standard (Hoganson et al., 2002): 20 mM Tris pH 8, 25 mM NaCl, 2.5% glycerol. Another useful formulation buffer suitable for administration to humans is 20 mM Tris, 2 mM $MgCl_2$, 25 mM NaCl, sucrose 10% w/v, polysorbate-80 0.02% w/v. Another formulation buffer that is suitable for recombinant adenovirus comprises 10-25 mM citrate buffer pH 5.9-6.2, 4-6% (w/w) hydroxypropyl-beta-cyclodextrin (HBCD), 70-100 mM NaCl, 0.018-0.035% (w/w) polysorbate-80, and optionally 0.3-0.45% (w/w) ethanol. Obviously, many other buffers can be used, and several examples of suitable formulations for the storage and for pharmaceutical administration of purified (adeno)virus preparations are known, including those that can for instance be found in EP0853660, U.S. Pat. No. 6,225,289 and in WO 99/41416, WO 99/12568, WO 00/29024, WO 01/66137, WO 03/049763, WO 03/078592, WO 03/061708.

In certain embodiments a composition comprising the adenovirus further comprises one or more adjuvants. Adjuvants are known in the art to further increase the immune response to an applied antigenic determinant, and pharmaceutical compositions comprising adenovirus and suitable adjuvants are for instance disclosed in WO 2007/110409, incorporated by reference herein. The terms "adjuvant" and "immune stimulant" are used interchangeably herein, and are defined as one or more substances that cause stimulation of the immune system. In this context, an adjuvant is used to enhance an immune response to the adenovirus vectors of the invention. Examples of suitable adjuvants include aluminium salts such as aluminium hydroxide and/or aluminium phosphate; oil-emulsion compositions (or oil-in-water compositions), including squalene-water emulsions, such as MF59 (see e.g. WO 90/14837); saponin formulations, such as for example QS21 and Immunostimulating Complexes (ISCOMS) (see e.g. U.S. Pat. No. 5,057,540; and WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as *E. coli* heat labile enterotoxin LT, cholera toxin CT, and the like. It is also possible to use vector-encoded adjuvant, e.g. by using heterologous nucleic acid that encodes a fusion of the oligomerization domain of C4-binding protein (C4bp) to the antigen of interest (Ogun, Dumon-Seignovert, Marchand, Holder, & Hill, 2008), or heterologous nucleic acid encoding a toll-like receptor (TLR) agonist, such as a TLR3 agonist such as dsRNA (see e.g. WO 2007/100908) or the like. Such rAd according to the invention may for instance encode an antigen of interest on one side of the bidirectional promoter and a TLR3 agonist on the other side of the bidirectional promoter. Such rAd are particularly suited for administration via a mucosal route, e.g. oral administration (see e.g. WO 2007/100908). In certain embodiments the compositions of the invention comprise aluminium as an adjuvant, e.g. in the form of aluminium hydroxide, aluminium phosphate, aluminium potassium phosphate, or combinations thereof, in concentrations of 0.05-5 mg, e.g. from 0.075-1.0 mg, of aluminium content per dose.

In other embodiments, the compositions do not comprise adjuvants.

A pharmaceutical composition according to the invention may in certain embodiments be a vaccine.

Adenovirus compositions may be administered to a subject, e.g. a human subject. The total dose of the adenovirus provided to a subject during one administration can be varied as is known to the skilled practitioner, and is generally between $1\times10^7$ viral particles (vp) and $1\times10^{12}$ vp, preferably between $1\times10^8$ vp and $1\times10^{11}$ vp, for instance between $3\times10^8$ and $5\times10^{10}$ vp, for instance between $10^9$ and $3\times10^{10}$ vp.

Administration of adenovirus compositions can be performed using standard routes of administration. Non-limiting embodiments include parenteral administration, such as by injection, e.g. intradermal, intramuscular, etc, or subcutaneous or transcutaneous, or mucosal administration, e.g. intranasal, oral, and the like. In one embodiment a composition is administered by intramuscular injection, e.g. into the deltoid muscle of the arm, or vastus lateralis muscle of the thigh. The skilled person knows the various possibilities to administer a composition, e.g. a vaccine in order to induce an immune response to the antigen(s) in the vaccine.

A subject as used herein preferably is a mammal, for instance a rodent, e.g. a mouse, or a non-human-primate, or a human. Preferably, the subject is a human subject.

It is also possible to provide one or more booster administrations of one or more adenovirus vaccines. If a boosting vaccination is performed, typically, such a boosting vaccination will be administered to the same subject at a moment between one week and one year, preferably between two weeks and four months, after administering the composition to the subject for the first time (which is in such cases referred to as 'priming vaccination'). In alternative boosting regimens, it is also possible to administer different vectors, e.g. one or more adenoviruses of different serotype, or other vectors such as MVA, or DNA, or protein, to the subject as a priming or boosting vaccination.

Various publications, which may include patents, published applications, technical articles and scholarly articles, are cited throughout the specification in parentheses, and full citations of each may be found at the end of the specification. Each of these cited publications is incorporated by reference herein, in its entirety.

EXAMPLES

Without further description, it is believed that one of ordinary skill in the art can, using the preceding description and the following illustrative methods and examples, make and utilize the present invention and practice the claimed methods. The following working examples therefore, specifically point out certain embodiments, features, and advantages of the present invention, and are not to be construed as limiting in any way the remainder of the disclosure. The examples merely serve to clarify the invention.

Methods

Cell Culture:

PER.C6® cells (Fallaux et al., 1998) were maintained in Dulbecco's modified Eagle's medium (DMEM) with 10% fetal bovine serum (FBS), supplemented with 10 mM $MgCl_2$.

Adenovirus Vector Construction in pAdApt35 and Pshuttle26 Plasmids

Different bidirectional promoter constructs were cloned into pAdApt35 (Vogels et al. 2007) or pshuttle26 plasmids. Pshuttle26 was constructed based on the previously described pAdapt26 plasmid (Abbink et al., 2007). A 2-Kb fragment containing the right part of the Ad26 vector genome was synthesized and subcloned into pAdApt26.Luc of which the SpeI site in the CMV promoter had first been disrupted by introduction of a single bp substitution. As a result pshuttle26 can be used to construct an adenovirus vector by homologous recombination with an Ad26 cosmid or by homologous recombination with an Ad26 full-length genome plasmid.

Since the pAdapt35 and pshuttle26 plasmids only harbor a standard unidirectional expression cassette with one promoter and one SV40 derived polyA signal, restriction sites to place another transgene plus BGH polyA signal were added by fusion PCR. The fusion PCR product containing SpeI, NotI—BGH polyA—EcoRI—Luciferase—KpnI, SalI, AvrII was inserted into the plasmids in the correct orientation by molecular cloning via SpeI and AvrII restriction sites. As a result, the unidirectional hCMV promoter could be replaced by the bidirectional promoter sequences using the flanking restriction sites AvrII and HindIII. Transgenes were placed on both sides of the bidirectional promoter using the HindIII and XbaI restriction sites on one side and AvrII, SalI or KpnI on the other side (FIG. 3A). The selection of AvrII, SalI or KpnI was dependent on the uniqueness of restriction sites in the plasmid sequence. The complete bidirectional expression cassettes with the different bidirectional promoter constructs were cloned in pShuttle26 plasmids and transferred to pAdapt35 plasmids using SpeI or NotI and XbaI restriction sites. A Kozak sequence (5' GCCACC 3') was included directly in front of each ATG start codon, and two stop codons (5' TGA TAA 3') were added at the end of each coding sequence. As described herein, the recombinant adenoviruses and vectors are referred to generally as rAd or rAd vectors and more specifically as rAd35 or rAd26 and associated vectors.

Adenovirus Generation, Infections and Propagation.

All adenoviruses were generated in PER.C6 cells by homologous recombination and produced as previously described (for rAd35: (Havenga et al., 2006); for rAd26: (Abbink et al., 2007)). Briefly, PER.C6 cells were transfected with rAd vector encoding plasmids, using Lipofectamine according to the instructions provided by the manufacturer (Life Technologies). For rescue of rAd35 vectors, the pAdApt35 plasmids and pWE/Ad35.pIX-rITR.dE3.50orf6 cosmid were used, whereas for rAd26 vectors, the pShuttle26 plasmids and pWE.Ad26.dE3.50orf6 cosmid were used. Cells were harvested one day after full cytopathic effect (CPE), freeze-thawed, centrifuged for 5 min at 3,000 rpm, and stored at −20° C. Next the viruses were plaque purified and amplified in PER.C6 cells cultured on a single well of a multiwell 24 tissue culture plate. Further amplification was carried out in PER.C6 cells cultured using a T25 tissue culture flask.

Expression Analysis

To evaluate potency of expression and expression balance, viral vectors were generated with reporter genes encoding enhanced Green Fluorescent Protein (eGFP protein accession number AAB02572.1) and Firefly Luciferase (Luciferase protein accession number ACH53166). The relative eGFP mean fluorescence intensity (MFI) and Luciferase relative light units (RLU) were recorded for each promoter and reporter gene combination with HEK293 cells (transient transfection with pAdApt vectors or pshuttle vectors) or A549 cells (virus infection). Luciferase activity was measured in cell lysates in presence with 0.1% DTT (1M), in Luminoskan™ Ascent Microplate Luminometer. The eGFP fluorescence was measured in the flow cytometer (FACS) by, trypsinizing, centrifuging, and re-suspending cell pellets in PBS/1% FBS (non-virus material) or in CellFix (virus material).

Genetic Stability Testing of Adenoviral Vectors in PER.C6 Cells.

Genetic stability testing of the vaccine vectors was performed to ensure genetic stability in the production process, which involves several passages in PER.C6 cells. Generation, plaque purification, and expansion to T25 format of the recombinant vaccine vectors was achieved as described above. Briefly, recombinant viruses were generated by plasmid transfections in the E1-complementing cell line PER.C6 and plaque-purified. 5 plaques were selected for up-scaling from multiwell 24 (MW24) to a T25 flask. Subsequently, new PER.C6 cells were infected in T25 format until viral passage number 13. The propagation of the viruses was performed using a predetermined infectious volume that would give full cytopathic effect 2 days post infection, which was retrospectively determined to be in a range of virus particle per cell ratio of 50 for rAd35 and 900 for rAd26. Viral DNA was isolated from p13 material and tested for presence of the complete transgene expression cassette by PCR analysis. The vaccine vectors were propagated up to passage number 13 in PER.C6 cells. The propagation was performed in a way to give full CPE two days post infection. rAd35 viruses were harvested 2 days after full CPE, whereas rAd26 viruses were harvested one day after full CPE. Viral DNA was isolated at passage 2, passage 5, passage 10 and passage 13 and absence of deletions was tested by PCR analysis using primers that flank the transgene expression cassette. Absence of deletion mutants was defined by the following parameters: Band size of PCR product corresponds to positive control (PCR product of plasmid used for virus rescue), no additional bands below the expected PCR product (unless additional bands show to be unspecific PCR products because they are also present in the positive control), approved assay: no band in the PCR $H_2O$ control. To further confirm genetic stability the PCR product of the expression cassette plus flanking regions of some plaques were sequenced.

Example 1: Bidirectional Promoter Construct Design

The potent bidirectional mouse CMV (mCMV) promoter was identified as a useful promoter for expression of two antigens from a bidirectional expression cassette in E1 region of adenoviral vectors in previous work, WO 2016/166088. While the vectors harbouring the mCMV bidirectional promoter expressed the antigens, were genetically stable and induced an immune response against both encoded antigens, antigen expression and the induced immune response were not balanced as explained in the following. Expression of the antigen placed on the right side of the bidirectional promoter was higher than of the antigen placed on the left side of the bidirectional promoter, resulting in a higher immune response against the antigen placed on the right side of the bidirectional promoter. The difference in expression levels for mCMV bidirectional was ca. 10 fold. However, in order to substitute the mix of two vectors expressing only one antigen, for certain applications a balanced bidirectional promoter is desirable which induces comparable levels of antigen expression of both antigens.

In order to identify a potent and more balanced bidirectional promoter a panel of new bidirectional promoters was designed. Bidirectional promoter designs with small size with a maximum size of 2 kB were preferred in order to retain sufficient space for antigens due to the overall size restriction of adenoviral vectors. Further, building blocks without extensive stretches of sequence identities (<15 nucleotides) were preferred in order to prevent deletions by homologous recombinations in the adenoviral vector. Bidirectional promoters of the present invention direct gene expression in a bidirectional fashion controlling expression of the genes placed on both sides of the bidirectional promoter sequence. These bidirectional promotors are continuous gene regulatory sequences that contain enhancer elements and intron elements besides the promoter elements and are defined by the building blocks as described herein. The building blocks used for design of the synthetic bidirectional promoters are derived from known potent unidirectional promoters, enhancers and intron sequences. Promoters drive expression of one gene placed downstream of the promoter sequence and typically contain a TATA box sequence and the transcription start site (TSS). Enhancer sequences can enhance gene expression from a promoter. Intron sequences have been described to increase gene expression in vitro and especially in vivo.

The Following Panel of Bidirectional Promoter Constructs were Designed and Tested:

| 1. | rCMV-hEF1α I | (FIG. 1A, SEQ ID NO: 1) |
| 2. | rCMV-hEF1α II | (FIG. 1B, SEQ ID NO: 2) |
| 3. | rhCMV-CAG1 | (FIG. 1C, SEQ ID NO: 3) |

-continued

| 4. | hCMV-CAG4 | (FIG. 1D, SEQ ID NO: 4) |
| 5. | rCMV-CAG | (FIG. 1E, SEQ ID NO: 5) |
| 6. | rhCMV-CAG2 | (FIG. 1F, SEQ ID NO: 6) |
| 7. | rCMV bidir 1 | (FIG. 1G, SEQ ID NO: 10) |
| 8. | rCMV bidir 2 | (FIG. 1H, SEQ ID NO: 8) |
| 9. | rCMV bidir 1.1 | (FIG. 1I, SEQ ID NO: 7) |

Other Bidirectional Promoter Constructs Were Also Tested in a Previous Patent Application (WO 2016/166088):

| 1. | mCMV bidir. |
| 2. | hCMV-CAG |
| 3. | mCMV-CAG |

Figure 1:
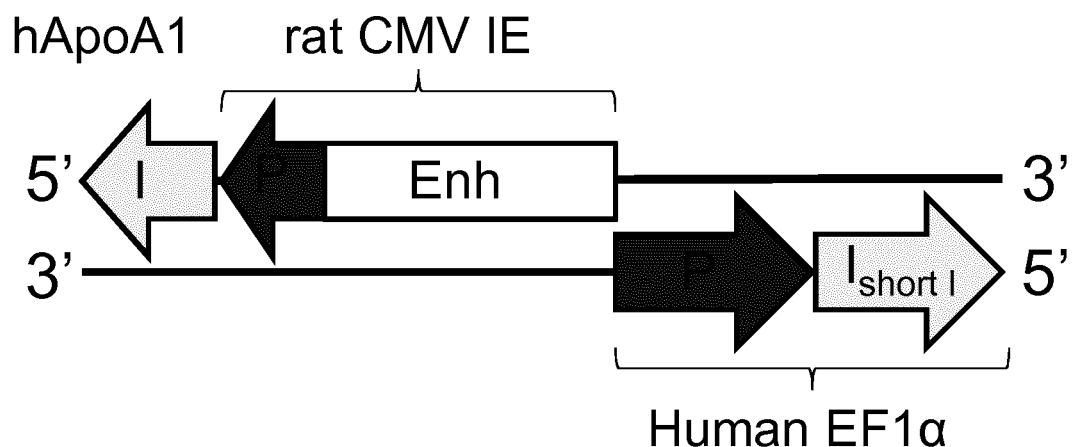
FIG. 1: Schematic representations of the hCMV-CAG4 promoter and other bidirectional promoter constructs including annotations for the identity and orientation of building blocks for the different bidirectional promoter sequences. P: promoter, Enh: enhancer, I: intron.
Figure 1:
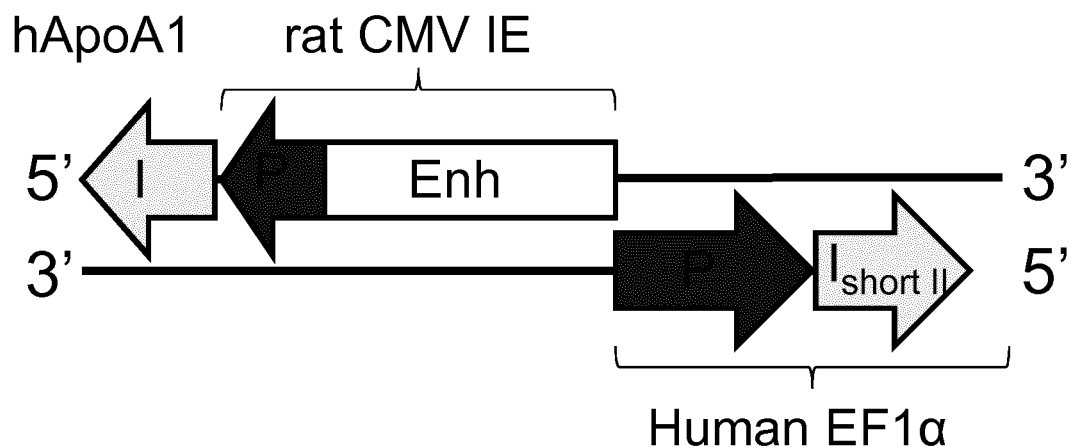

Schematic representations of the bidirectional promoter designs and their building blocks are shown in FIG. 1 and described in more detail below:

The promoter and enhancer building blocks used in the different designs are derived from cytomegalovirus immediate early (IE) regions (typically referred to herein as the hCMV promoter and the hCMV enhancer and sometimes also referred to as hCMV IE), the chicken beta actin/rabbit beta globin promoter sequence and the human elongation factor 1 α promoter (hEF1α promoter) sequence. The introns are derived from chimeric chicken beta actin/rabbit beta globin sequence, hEF1α first intron and the human apolipoprotein A-1 intron (hApoA1 intron).

The human cytomegalovirus major immediate early promoter is known as a potent promoter in various mammalian cell lines (Boshart et al., 1985). hCMV and other herpesviruses express genes in three phases, immediate early (IE), early and late phase. The major immediate early promoters activate heterologous genes at high levels in various mammalian cell lines.

While the human cytomegalovirus major immediate early promoter and enhancer are most frequently used in design of transgene expression cassettes (Addison, Hitt, Kunsken, & Graham, 1997; C. Harro et al., 2009), major immediate early promoters and enhancers of cytomegaloviruses infecting other species such as mouse (mCMV) (Addison et al., 1997; Chatellard et al., 2007; C. Harro et al., 2009), rat (rCMV) (Sandford & Burns, 1996; Voigt, Sandford, Hayward, & Burns, 2005) and rhesus monkeys (rhCMV) (Barry, Alcendor, Power, Kerr, & Luciw, 1996; Chan, Chiou, Huang, & Hayward, 1996; Chang et al., 1993; Hansen, Strelow, Franchi, Anders, & Wong, 2003) are also known and can be used in the design of potent expression cassettes. The hEF1α promoter is also described to be a potent promoter sequence for heterologous gene expression in mammalian cells (Kim, Uetsuki, Kaziro, Yamaguchi, & Sugano, 1990).

The chimeric promoter CAG consisting of the hCMV enhancer, the chicken beta actin promoter (A) and a hybrid chicken beta actin/rabbit beta globin intron (G) sequence is described to be a potent promoter for expression of heterologous genes, can be shortened and can be utilized for expression of antigens (Richardson et al., 2009). The study by Richardson et al. describes a modification of the CAG promoter resulting in the A829CAG promoter version in which the hybrid intron is significantly shortened. This A829CAG promoter version without the hCMV enhancer (A829AG) was used as a building block for design of the bidirectional promoters, denoted as the AG portion in the drawings, but referred to as CAG in the names of the bidirectional promoters and referred to as CAG or AG throughout the text.

In the following the arrangement of the building blocks to design the bidirectional promoter sequences is described:

The shortened AG promoter and hEF1α promoter harbor introns as crucial parts of the described potent regulatory sequences. Where an AG promoter or an hEF1α promoter was used in the bidirectional promoter design, we also placed a heterologous intron sequence on the opposite side of the bidirectional promoter design. Different potential bidirectional promoter designs of the rCMV immediate early promoter were made based on the natural bidirectionality of the mouse CMV promoter.

It has been described previously that a synthetic combination of an hEF1α derived intron and an mCMV promoter sequence yields a potent regulatory sequence. Therefore, hEF1α sequences were combined with elements of the rCMV promoter (another promoter derived from a muromegalovirus like the mCMV) and enhancer to design the bidirectional promoter sequences rCMV-hEF1α I and rCMV-hEF1α II (see, for example, FIGS. 1A and 1B). Since the hEF1α intron is described to increase expression levels but is a very long sequence, our designs have attempted to significantly shorten the hEF1α intron sequence as is described by experimental approach for the CAG promoter (Richardson et al., 2009). To this end, part of the intron sequence was removed while preserving the described splice donor, splice acceptor and putative branch point site plus described cellular factor binding sites. Two different versions of the shortened intron were designed in which the promoter/intron combination hEF1α I preserves more sites than the promoter/intron combination hEF1α II, yielding the bidirectional promoters rCMV-hEF1α I and rCMV-hEF1α II.

Additional bidirectional promoter designs are based on the shortened AG promoter in combination with enhancer and promoter sequences of cytomegalovirus major immediate early promoters derived from different species, including rhesus CMV (rhCMV), rat CMV(rCMV) and human CMV (hCMV). These bidirectional promoters are called rhCMV-CAG1, rhCMV-CAG2, hCMV-CAG4 and rCMV-CAG. The difference between rhCMV-CAG1 and rhCMV-CAG2 is the orientation of the rhCMV enhancer sequence.

Besides the synthetic bidirectional promoter designs, a potentially natural bidirectional promoter derived from the rCMV mIE region was used as a basis for the bidirectional promoter sequences rCMV bidir 1 and rCMV bidir 2 and rCMV bidir 1.1. While all three bidirectional promoter designs harbor a putative minimal rCMV promoter and a putative minimal rCMV vOX2 promoter flanking an rCMV enhancer sequence, the designs differ in the length of the enhancer fragment and the orientation of the enhancer fragment. The vOX2 promoter is driving transcription of the rat cellular CD200 (vOX2) gene immediately to the right of the MIE region (Voigt et al., 2005).

Example 2: Screening of Different Promoter Constructs for Potent and Balanced Expression of Reporter Genes In a first screening experiment, expression from different bidirectional promoter constructs was evaluated with transient transfections in HEK293 using reporter genes Luciferase and eGFP for a quantitative potency readout. For the transient transfections of pAdapt35 plasmids, the bidirectional promoters had the Luciferase transgene on the left side and the eGFP transgene on the right side of the bidirectional promoter.

Figure 2:
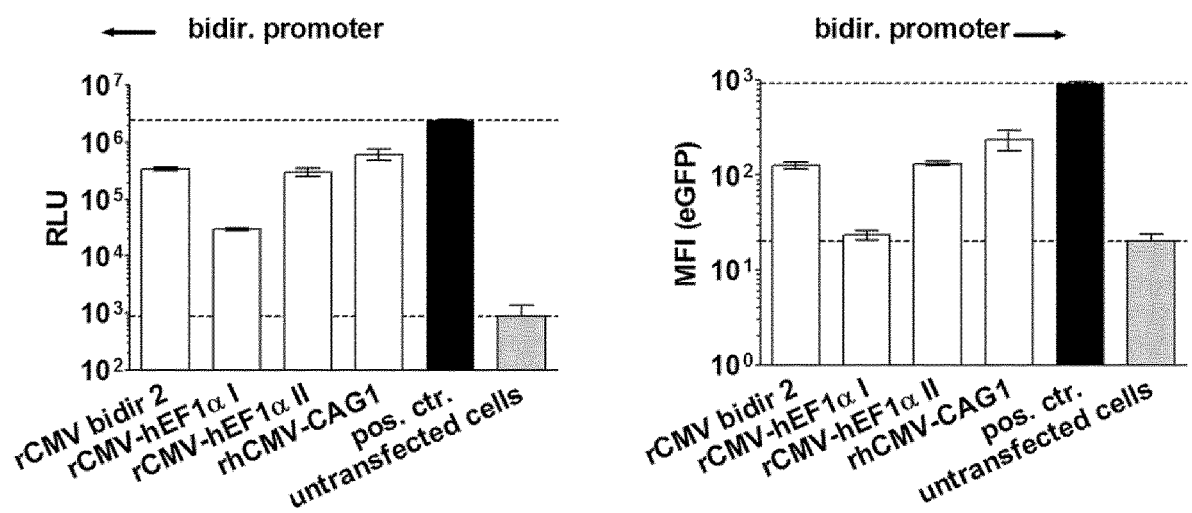
FIG. 2: Expression of Luciferase and eGFP with different bidirectional promoter constructs evaluated with transient transfections in HEK293 cells. Luciferase expression is measured as relative light units (RLU) and eGFP expression is measured as mean fluorescence intensity (MFI) by FACS. Results of three different experiments screening the different promoter constructs are shown. (A) Shown are bar graphs of the results for Luciferase expression from the left side and eGFP expression from the right side of different bidirectional promoters. Results in each bar graph are shown in order from left to right for rat-CMV-bidir-2, rCMV-hEF1α

Three independent transfection experiments were performed with plasmids harbouring the different bidirectional promoter designs. In experiment 1 (FIG. 2A) the promoters rCMV bidir.2, rCMV-hEF1α II, rhCMV-hEF1α I and rhCMV-CAG1 were tested. While rCMV bidir.2, rCMV-EF1α II and rhCMV-CAG1 invariably display bidirectional promoter function albeit less potent than the hCMV promoter with unidirectional control (SEQ ID NO:9), rCMV-hEF1α I does not display promoter potency above the negative control for eGFP expression and very poor promoter potency for luciferase expression. In experiment 1 rhCMV-CAG1 is the most potent bidirectional promoter, however both eGFP and Luciferase are expressed at a lower level than the respective positive controls driven by the potent unidirectional hCMV promoter. In the screening experiment 2 (FIG. 2B) the promoters rCMV bidir.1.1, rCMV-CAG and hCMV-CAG4 were tested. The rCMV bidir.1.1 promoter displayed low to undetectable promoter potency on both sides. rCMV-CAG displays bidirectional promoter potency, albeit lower than the hCMV unidirectional control. By contrast, and surprisingly, hCMV-CAG4 is a potent bidirectional promoter with comparable to higher potency both on left and right side to hCMV unidirectional control. In a third screening experiment rhCMV-CAG2 and rCMV bidir.1 were tested along with hCMV-CAG4. From the set of tested bidirectional promoter constructs hCMV-CAG4 was identified as the most promising candidate. The other synthetic bidirectional promoter designs consisting of different unidirectional promoter building blocks mainly displayed good bidirectional promoter functions, however the expression of the reporter genes was lower than driven by the unidirectional hCMV promoter control. Comparable to the mouse CMV bidirectional promoter, the rCMV immediate early promoter can be designed as a bidirectional promoter which is however less potent. The results show that it is unpredictable which combination of building blocks provides good functionality (potent expression in both directions, i.e. similar to expression under control of the hCMV unidirectional promoter) of a bidirectional promoter.

A schematic representation of hCMV-CAG4 including annotations for the identity and orientation of the building blocks is displayed in FIG. 3. The right side of the bidirectional hCMV-CAG4 promoter consists of the shortened CAG promoter part described by Richardson et al. including the chicken beta actin intron, excluding the hCMV enhancer part. The hCMV enhancer part is present however inverted in orientation to point to the left side of the bidirectional promoter which consists of the hCMV promoter including the hCMV enhancer. In addition to the presence of an intrinsic intron on the right side of the promoter, a heterologous short intron from human apolipoprotein A-1 (hApoA1) was placed on the left side of the bidirectional promoter. While here the terms "left" and "right" are used for ease of description, the skilled person will immediately recognize that the bidirectional promoter construct can also be turned around and used in the opposite orientation. With its relatively small size of about 1.4 kb, the hCMV-CAG4 promoter is well suited for use as a bidirectional promoter in a recombinant adenoviral vector.

Example 3: Potency and Balance of Transgene Expression from Adenoviral Vectors Harbouring an hCMV-CAG4 Expression Cassette To further asses potency and balance of expression from the E1 region of adenoviral vectors, we generated Ad26 and Ad35 vectors harbouring a hCMV-CAG4 bidirectional expression cassette in the E1 region. Four different vectors, viz. Ad26.eGFP.hCMV-CAG4.Luc, Ad26.Luc.hCMV-CAG4.eGFP, Ad35.eGFP.hCMV-CAG4.Luc and Ad35.Luc.hCMV-CAG4.eGFP, were generated to assess potency and balance of reporter gene expression upon transduction of non-complementing A549 cells. Transductions were performed at 100 VP/cell and 1000 VP/cell. Since results at both VP/cell ratios were similar, only results of the 1000 VP/cell transductions are shown in FIG. 3. In order to estimate a tenfold difference in expression 100 VP/cell and 1000 VP/cell, transductions of the positive control vectors Ad.Luc and Ad.eGFP expressing the reporter genes under control of the unidirectional hCMV promoter are shown. Panel 4A shows that hCMV-CAG4 induces potent expression of both the reporter genes from an Ad26 E1 bidirectional expression cassette, with expression levels comparable to or slightly lower than from the Ad26.Luc and Ad26.eGFP control vectors at 1000 VP/cell. Ad26.Luc.hCMV-CAG4.eGFP is further directly compared to Ad26.Luc.mCMV bidir.eGFP and shows reduced transgene expression of eGFP compared to mCMV bidir., however also shows an overall more balanced transgene expression. Panel 4B shows transgene expression from an hCMV-CAG4 bidirectional expression cassette in Ad35 vectors. Interestingly, expression driven by the CAG side of the bidirectional hCMV-CAG4 promoter seems further reduced in Ad35 vectors than in Ad26 vectors. Therefore, while potent bidirectional promoters can be used in rAdV derived from different serotypes, a different promoter may be optimal for use in one rAdV over another, further exemplifying that intricate design of promoters and expression cassettes is required for optimal viral vectors.

Example 4: Genetic Stability Testing of Adenoviral Vectors Harboring an hCMV-CAG4 Bidirectional Expression Cassette in E1 Region Besides transgene expression, genetic stability during the production of AdV is a crucial parameter for a useful AdV expressing two antigens. Therefore genetic stability was tested as described in a previous application, WO 2016/166088. Briefly, the vectors Ad26.Luc.hCMV-CAG4.eGFP and Ad26.eGFP.hCMV-CAG4.Luc were generated by plasmid transfection in PER.C6 cells and viral populations were isolated by plaque picking. Ten plaques per vector were propagated to viral passage number (vpn) 3. From there on, five plaques were selected for extended passaging up to vpn 13. Genetic stability was evaluated by identity PCRs on the E1 expression cassette region (FIG. 4), and E3 and E4 region (data of E3 and E4 PCRs are not shown). Absence of small deletions or point mutations was confirmed by standard Sanger sequencing of the E1 PCR product of vpn 13. Five out of five plaques of both Ad26.Luc.hCMV-CAG4.eGFP and Ad26.eGFP.hCMV-CAG4.Luc remained genetically stable up to vpn 13. Of note, some additional bands are visible in the gel pictures which do not represent deletion bands but unspecific PCR bands caused by the highly GC rich GAG promoter sequence.

CONCLUSION

As described supra, by screening a panel of new bidirectional promoter constructs, it was determined that it is unpredictable which bidirectional promoter constructs will give the desired promoter properties. In fact, even bidirectional promoter constructs that seem to be very similar do not necessarily give the same results. For example, the bidirectional hCMV-CAG4 promoter, with a human CMV promoter on the left side and a CAG promoter on the right side, showed particularly good results for both potency and balance of expression for two different transgenes from the E1 region of rAd26 and rAd35 vectors. Tested constructs that a priori were considered to be very similar to hCMV-CAG4, included rhCMV-CAG2 and rCMV-CAG. These constructs also have a CMV promoter portion on the left side, although they are derived from different species, and they also have a CAG promoter portion on the right side. Even though these constructs showed coordinate expression of the encoded reporter genes, surprisingly the expression was both less potent and less balanced than the expression from the bidirectional hCMV-CAG4 promoter. Furthermore, rAd with the bidirectional hCMV-CAG4 promoter were determined to be genetically stable even after serial passaging in PER.C6 cells to P13. Thus, unpredictably, the bidirectional hCMV-CAG4 promoter of the present invention is a promoter with surprisingly preferable characteristics for use in recombinant viral vectors that can be used in gene therapy or vaccines where balanced and potent expression are desired.

TABLE 1

| Bidirectional promoter | Size | Balance | Potency left side (compared to standard) in % | Potency right side (compared to standard) in % | Genetic stability in AdV |
|---|---|---|---|---|---|
| hCMV-CAG4 | 1395 | ~1/1-1.8/1 | ~100 | ~60 | confirmed |
| mCMV* | 1958 | ~1/10 | ~100 | ~1000 | confirmed |

*described in WO 2016/166088

REFERENCES

U.S. Patent Documents:
U.S. Pat. No. 5,057,540A (Oct. 15, 1991). "Saponin adjuvant". Kensil, Charlotte A.; Marciani, Dante J.
U.S. Pat. No. 5,122,458A (Jun. 16, 1992). "Use of a bGH gDNA polyadenylation signal in expression of non-bGH polypeptides in higher eukaryotic cells". Post, Leonard E.; Palermo, Daniel P.; Thomsen, Darrell R.; Rottman, Fritz M.; Goodwin, Edward C.; Woychik, Richard P.
U.S. Pat. No. 5,559,099A (Sep. 24, 1996). "Penton base protein and methods of using same". Wickham, Thomas J.; Kovesdi, Imre; Brough, Douglas E.; McVey, Duncan L.; Brader, Joseph T.
U.S. Pat. No. 5,837,511A (Nov. 17, 1998). "Non-group C adenoviral vectors". Falck Pedersen, Erik S.; Crystal, Ronald G.; Mastrangeli, Andrea; Abrahamson, Karil
U.S. Pat. No. 5,837,520A (Nov. 17, 1998). "Method of purification of viral vectors". Shabram, Paul W.; Huyghe, Bernard G.; Liu, Xiaodong; Shepard, H. Michael
U.S. Pat. No. 5,846,782A (Dec. 8, 1998). "Targeting adenovirus with use of constrained peptide motifs". Wickham, Thomas J.; Roelvink, Petrus W.; Kovesdi, Imre
U.S. Pat. No. 5,851,806A (Dec. 22, 1998). "Complementary adenoviral systems and cell lines". Kovesdi, Imre; Brough, Douglas E.; McVey, Duncan L.; Bruder, Joseph T.; Lizonova, Alena
U.S. Pat. No. 5,891,690A (Apr. 6, 1999). "Adenovirus E1-complementing cell lines". Massie, Bernard
U.S. Pat. No. 5,965,541A (Oct. 12, 1999). "Vectors and methods for gene transfer to cells". Wickham, Thomas J.; Kovesdi, Imre; Brough, Douglas E.
U.S. Pat. No. 5,981,225A (Nov. 9, 1999). "Gene transfer vector, recombinant adenovirus particles containing the same, method for producing the same and method of use of the same". Kochanek, Stefan; Schiedner, Gudrun
U.S. Pat. No. 5,994,106A (Nov. 30, 1999). "Stocks of recombinant, replication-deficient adenovirus free of replication-competent adenovirus". Kovesdi, Imre; Brough, Douglas E.; McVey, Duncan L.; Bruder, Joseph T.; Lizonova, Alena
U.S. Pat. No. 5,994,128A (Nov. 30, 1999). "Packaging systems for human recombinant adenovirus to be used in gene therapy". Fallaux, Frits Jacobus; Hoeben, Robert Cornelis; Van der Eb, Alex Jan; Bout, Abraham; Valerio, Domenico
U.S. Pat. No. 6,020,191A (Feb. 1, 2000). "Adenoviral vectors capable of facilitating increased persistence of transgene expression". Scaria, Abraham; Gregory, Richard J.; Wadsworth, Samuel C.
U.S. Pat. No. 6,040,174A (Mar. 21, 2000). "Defective adenoviruses and corresponding complementation lines". Imler, Jean Luc; Mehtali, Majid; Pavirani, Andrea
U.S. Pat. No. 6,083,716A (Jul. 4, 2000). "Chimpanzee adenovirus vectors". Wilson, James M.; Farina, Steven F.; Fisher, Krishna J.
U.S. Pat. No. 6,113,913A (Sep. 5, 2000). "Recombinant adenovirus". Brough, Douglas E.; Kovesdi, Imre
U.S. Pat. No. 6,225,289B1 (May 1, 2001). "Methods and compositions for preserving adenoviral vectors". Kovesdi, Imre; Ransom, Stephen C.
U.S. Pat. No. 6,261,823B1 (Jul. 17, 2001). "Methods for purifying viruses". Tang, John Chu Tay; Vellekamp, Gary; Bondoc, Jr., Laureano L.
U.S. Pat. No. 6,485,958B2 (Nov. 26, 2002). "Method for producing recombinant adenovirus". Blanche, Francis; Guillaume, Jean Marc
U.S. Pat. No. 7,326,555B2 (Feb. 5, 2008). "Methods of adenovirus purification". Konz, Jr., John O.; Lee, Ann L.; To, Chi Shung Brian; Goerke, Aaron R
U.S. Pat. No. 8,932,607B2 (Jan. 13, 2015). "Batches of recombinant adenovirus with altered terminal ends". Custers, Jerome H. H. V.; Vellinga, Jort
European Patent Documents:
EP1230354B1 (Jan. 7, 2004). "PERMANENT AMNIOCYTE CELL LINE, THE PRODUCTION THEREOF AND ITS USE FOR PRODUCING GENE TRANSFER VECTORS". KOCHANEK, Stefan; SCHIEDNER, Gudrun
EP1601776B1 (Jul. 2, 2008). "EXPRESSION VECTORS COMPRISING THE MCMV IE2 PROMOTER". CHATELLARD, Philippe; IMHOF, Markus
EP853660B1 (Jan. 22, 2003). "METHOD FOR PRESERVING INFECTIOUS RECOMBINANT VIRUSES, AQUEOUS VIRAL SUSPENSION AND USE AS MEDICINE". SENE, Claude
International Patent Application Publications:
WO2003049763A1 (Jun. 19, 2003). "COMPOSITION FOR THE PRESERVATION OF VIRUSES". SETIAWAN, Kerrie; CAMERON, Fiona, Helen
WO2003061708A1 (Jul. 31, 2003). "STABILIZED FORMULATIONS OF ADENOVIRUS". PUNGOR, Erno
WO2003078592A2 (Sep. 25, 2003). "METHOD FOR THE PURIFICATION, PRODUCTION AND FORMULATION OF ONCOLYTIC ADENOVIRUSES".

MEMARZADEH, Bahram; PENNATHUR-DAS, Rukmini; WYPYCH, Joseph; YU, De Chao

WO2003104467A1 (Dec. 18, 2003). "MEANS AND METHODS FOR THE PRODUCTION OF ADENOVIRUS VECTORS". VOGELS, Ronald; BOUT, Abraham WO2004001032A2 (Dec. 31, 2003). "STABLE ADENOVIRAL VECTORS AND METHODS FOR PROPAGATION THEREOF". VOGELS, Ronald; HAVENGA, Menzo, Jans, Emco; ZUIJDGEEST, David, Adrianus, Theodorus WO2004004762A1 (Jan. 15, 2004). "ISCOM PREPARATION AND USE THEREOF". MOREIN, Bror; LÖVGREN BENGTSSON, Karin WO2004020971A2 (Mar. 11, 2004). "CHROMATOGRAPHIC METHODS FOR ADENOVIRUS PURIFICATION". SENESAC, Joseph WO2004037294A2 (May 6, 2004). "NEW SETTINGS FOR RECOMBINANT ADENOVIRAL-BASED VACCINES". HAVENGA, Menzo, Jans, Emco; HOLTERMAN, Lennart; KOSTENSE, Stefan; PAU, Maria, Grazia; SPRANGERS, Mieke, Caroline; VOGELS, Ronald WO2004055187A1 (Jul. 1, 2004). "RECOMBINANT VIRAL-BASED MALARIA VACCINES". PAU, Maria Grazia; HOLTERMAN, Lennart; KASPERS, Jorn; STEGMANN, Antonius, Johannes, Hendrikus WO2005002620A1 (Jan. 13, 2005). "QUIL A FRACTION WITH LOW TOXICITY AND USE THEREOF". MOREIN, Bror; LÖVGREN BENGTSSON, Karin; EKSTROM, Jill; RANLUND, Katarina WO2005071093A2 (Aug. 4, 2005). "CHIMPANZEE ADENOVIRUS VACCINE CARRIERS". CIRILLO, Agostino; COLLOCA, Stefano; ERCOLE, Bruno, Bruni; MEOLA, Annalisa; NICOSIA, Alfredo; SPORENO, Elisabetta WO2005080556A2 (Sep. 1, 2005). "VIRUS PURIFICATION METHODS". WEGGEMAN, Miranda; VAN CORVEN, Emile Joannes Josephus Maria WO2006053871A2 (May 26, 2006). "MULTIVALENT VACCINES COMPRISING RECOMBINANT VIRAL VECTORS". HAVENGA, Menzo, Jans, Emco; VOGELS, Ronald; SADOFF, Jerald; HONE, David; SKEIKY, Yasir Abdul Wahid; RADOSEVIC, Katarina WO2006108707A1 (Oct. 19, 2006). "VIRUS PURIFICATION USING ULTRAFILTRATION". WEGGEMAN, Miranda WO2006120034A1 (Nov. 16, 2006). "VACCINE COMPOSITION". ERTL, Peter, Franz; TITE, John, Philip; VAN WELY, Catherine Ann WO2007073513A2 (Jun. 28, 2007). "METHOD FOR PROPAGATING ADENOVIRAL VECTORS ENCODING INHIBITORY GENE PRODUCTS". GALL, Jason, G., D.; BROUGH, Douglas, E.; RICHTER, King, C.

WO2007100908A2 (Sep. 7, 2007). "CHIMERIC ADENOVIRAL VECTORS". TUCKER, Sean, N.

WO2007104792A2 (Sep. 20, 2007). "RECOMBINANT ADENOVIRUSES BASED ON SEROTYPE 26 AND 48, AND USE THEREOF". BAROUCH, Dan H.; HAVENGA, Menzo Jans Emko WO2007110409A1 (Oct. 4, 2007). "COMPOSITIONS COMPRISING A RECOMBINANT ADENOVIRUS AND AN ADJUVANT". HAVENGA, Menzo Jans Emko; RADOSEVIC, Katarina WO2009026183A1 (Feb. 26, 2009). "USE OF CHIMERIC HIV/SIV GAG PROTEINS TO OPTIMIZE VACCINE-INDUCED T CELL RESPONSES AGAINST HIV GAG". NABEL, Gary, J.; YANG, Zhi-Yong; SHI, Wei; BAROUCH, Dan, H.

WO2009117134A2 (Sep. 24, 2009). "AEROSOLIZED GENETIC VACCINES AND METHODS OF USE". ROEDERER, Mario; RAO, Srinivas; NABEL, Gary, J.; ANDREWS, Charla, Anne WO2010085984A1 (Aug. 5, 2010). "SIMIAN ADENOVIRUS NUCLEIC ACID- AND AMINO ACID-SEQUENCES, VECTORS CONTAINING SAME, AND USES THEREOF". COLLOCA, Stefano; NICOSIA, Alfredo; CORTESE, Riccardo; AMMENDOLA, Virginia; AMBROSIO, Maria WO2010086189A2 (Aug. 5, 2010). "SIMIAN ADENOVIRUS NUCLEIC ACID- AND AMINO ACID-SEQUENCES, VECTORS CONTAINING SAME, AND USES THEREOF". COLLOCA, Stefano; NICOSIA, Alfredo; CORTESE, Riccardo; AMMENDOLA, Virginia; AMBROSIO, Maria WO2010096561A1 (Aug. 26, 2010). "SYNTHETIC HIV/SIV GAG PROTEINS AND USES THEREOF". NABEL, Gary J.; YANG, Zhi-yong; SHI, Wei; BAROUCH, Dan H.

WO2011045378A1 (Apr. 21, 2011). "METHOD FOR THE PURIFICATION OF ADENOVIRUS PARTICLES". DE VOCHT, Marcel, Leo; VEENSTRA, Marloes WO2011045381A1 (Apr. 21, 2011). "PROCESS FOR ADENOVIRUS PURIFICATION FROM HIGH CELL DENSITY CULTURES". DE VOCHT, Marcel, Leo; VEENSTRA, Marloes WO2013139911A1 (Sep. 26, 2013). "VACCINE AGAINST RSV". RADOSEVIC, Katarina; CUSTERS, Jerôme H. H. V.; VELLINGA, Jort; WIDJOJOATMODJO, Myra N.

WO2013139916A1 (Sep. 26, 2013). "VACCINE AGAINST RSV". RADOSEVIC, Katarina; CUSTERS, Jerôme H. H. V.; VELLINGA, Jort; WIDJOJOATMODJO, Myra N.

OTHER REFERENCES

Books

Ausubel et al., Current Protocols in Molecular Biology, Wiley Interscience Publishers, NY (1995)

Ausubel F. M., et al. (editors). Current Protocols in Molecular Biology; the series Methods in Enzymology, Academic Press, Inc. (1987)

Freshney, R. I., Culture of animal cells: A manual of basic technique, fourth edition, Wiley-Liss Inc., ISBN 0-471-34889-9 (2000)

Frokjaer S. and Hovgaard L. (editors), Pharmaceutical Formulation Development of Peptides and Proteins, Taylor & Francis (2000)

Gennaro, A. R. (editor), Remington's Pharmaceutical Sciences, 18th edition, Mack Publishing Company (1990)

Horowitz, M. S., Adenoviruses, Chapter 68, in Virology, (B. N. Fields et al. (editors), 3rd Ed., Raven Press, Ltd., New York (1996)

Kibbe A. (editor), Handbook of Pharmaceutical Excipients, 3rd edition, Pharmaceutical Press (2000)

Kruse and Paterson (editors), Tissue Culture, Academic Press. (1973)

MacPherson M. J., Hams B. D., Taylor G. R. (editors), PCR2: A Practical Approach (1995)

Sambrook et al., Molecular Cloning, a Laboratory Manual, 2nd Ed., Cold Spring Harbor Press, Cold Spring Harbor, N.Y. (1989)

Sambrook, Fritsch and Maniatis, Molecular Cloning: A Laboratory Manual, 2nd Ed., (1989)

Shenk, Thomas, Adenoviridae and their Replication, Chapter 67, in Virology, B. N. Fields et al. (editors), 3rd Ed., Raven Press, Ltd., New York (1996)

Watson et al., Recombinant DNA, 2nd ed., Scientific American Books. (1992)

Journals

Abbink, P., Lemckert, A. A., Ewald, B. A., Lynch, D. M., Denholtz, M., Smits, S., . . . Barouch, D. H. (2007). Comparative seroprevalence and immunogenicity of six rare serotype recombinant adenovirus vaccine vectors from subgroups B and D. *J Virol*, 81(9), 4654-4663. doi: 10.1128/JVI.02696-06

Abbink, P., Maxfield, L. F., Ng'ang'a, D., Borducchi, E. N., Iampietro, M. J., Bricault, C. A., . . . Barouch, D. H. (2015). Construction and evaluation of novel rhesus monkey adenovirus vaccine vectors. *J Virol*, 89(3), 1512-1522. doi: 10.1128/JVI.02950-14

Abrahamsen, K., Kong, H. L., Mastrangeli, A., Brough, D., Lizonova, A., Crystal, R. G., & Falck-Pedersen, E. (1997). Construction of an adenovirus type 7a E1A-vector. *J Virol*, 71(11), 8946-8951.

Addison, C. L., Hitt, M., Kunsken, D., & Graham, F. L. (1997). Comparison of the human versus murine cytomegalovirus immediate early gene promoters for transgene expression by adenoviral vectors. *J Gen Virol*, 78 (Pt 7), 1653-1661. doi: 10.1099/0022-1317-78-7-1653

Amendola, M., Venneri, M. A., Biffi, A., Vigna, E., & Naldini, L. (2005). Coordinate dual-gene transgenesis by lentiviral vectors carrying synthetic bidirectional promoters. *Nat Biotechnol*, 23(1), 108-116.

Andrianaki, A., Siapati, E. K., Hirata, R. K., Russell, D. W., & Vassilopoulos, G. (2010). Dual transgene expression by foamy virus vectors carrying an endogenous bidirectional promoter. *Gene Ther*, 17(3), 380-388. doi: 10.1038/gt.2009.147

Bangari, D. S., & Mittal, S. K. (2006). Development of nonhuman adenoviruses as vaccine vectors. *Vaccine*, 24(7), 849-862. doi: 10.1016/j.vaccine.2005.08.101

Barry, P. A., Alcendor, D. J., Power, M. D., Kerr, H., & Luciw, P. A. (1996). Nucleotide sequence and molecular analysis of the rhesus cytomegalovirus immediate-early gene and the UL121-117 open reading frames. *Virology*, 215(1), 61-72. doi: 10.1006/viro.1996.0007

Barski, O. A., Siller-Lopez, F., Bohren, K. M., Gabbay, K. H., & Aguilar-Cordova, E. (2004). Human aldehyde reductase promoter allows simultaneous expression of two genes in opposite directions. *Biotechniques*, 36(3), 382-384, 386, 388.

Belousova, N., Harris, R., Zinn, K., Rhodes-Selser, M. A., Kotov, A., Kotova, O., . . . Alvarez, R. D. (2006). Circumventing recombination events encountered with production of a clinical-grade adenoviral vector with a double-expression cassette. *Mol Pharmacol*, 70(5), 1488-1493.

Boshart, M., Weber, F., Jahn, G., Dorsch-Hasler, K., Fleckenstein, B., & Schaffner, W. (1985). A very strong enhancer is located upstream of an immediate early gene of human cytomegalovirus. *Cell*, 41(2), 521-530.

Brough, D. E., Lizonova, A., Hsu, C., Kulesa, V. A., & Kovesdi, I. (1996). A gene transfer vector-cell line system for complete functional complementation of adenovirus early regions E1 and E4. *J Virol*, 70(9), 6497-6501.

Chan, Y. J., Chiou, C. J., Huang, Q., & Hayward, G. S. (1996). Synergistic interactions between overlapping binding sites for the serum response factor and ELK-1 proteins mediate both basal enhancement and phorbol ester responsiveness of primate cytomegalovirus major immediate-early promoters in monocyte and T-lymphocyte cell types. *J Virol*, 70(12), 8590-8605.

Chang, Y. N., Jeang, K. T., Chiou, C. J., Chan, Y. J., Pizzorno, M., & Hayward, G. S. (1993). Identification of a large bent DNA domain and binding sites for serum response factor adjacent to the NFI repeat cluster and enhancer region in the major IE94 promoter from simian cytomegalovirus. *J Virol*, 67(1), 516-529.

Chatellard, P., Pankiewicz, R., Meier, E., Durrer, L., Sauvage, C., & Imhof, M. O. (2007). The IE2 promoter/enhancer region from mouse CMV provides high levels of therapeutic protein expression in mammalian cells. *Biotechnol Bioeng*, 96(1), 106-117. doi: 10.1002/bit.21172

Cohen, C. J., Xiang, Z. Q., Gao, G. P., Ertl, H. C., Wilson, J. M., & Bergelson, J. M. (2002). Chimpanzee adenovirus CV-68 adapted as a gene delivery vector interacts with the coxsackievirus and adenovirus receptor. *J Gen Virol*, 83(Pt 1), 151-155.

Collins, P. J., Kobayashi, Y., Nguyen, L., Trinklein, N. D., & Myers, R. M. (2007). The ets-related transcription factor GABP directs bidirectional transcription. *PLoS Genet*, 3(11), e208. doi: 10.1371/journal.pgen.0030208

Fallaux, F. J., Bout, A., van der Velde, I., van den Wollenberg, D. J., Hehir, K. M., Keegan, J., . . . Hoeben, R. C. (1998). New helper cells and matched early region 1-deleted adenovirus vectors prevent generation of replication-competent adenoviruses. *Hum Gene Ther*, 9(13), 1909-1917.

Farina, S. F., Gao, G. P., Xiang, Z. Q., Rux, J. J., Burnett, R. M., Alvira, M. R., . . . Wilson, J. M. (2001). Replication-defective vector based on a chimpanzee adenovirus. *J Virol*, 75(23), 11603-11613. doi: 10.1128/JVI.75.23.11603-11613.2001

Gao, G. P., Engdahl, R. K., & Wilson, J. M. (2000). A cell line for high-yield production of E1-deleted adenovirus vectors without the emergence of replication-competent virus. *Hum Gene Ther*, 11(1), 213-219. doi: 10.1089/10430340050016283

Geisbert, T. W., Bailey, M., Hensley, L., Asiedu, C., Geisbert, J., Stanley, D., . . . Sullivan, N. J. (2011). Recombinant adenovirus serotype 26 (Ad26) and Ad35 vaccine vectors bypass immunity to Ad5 and protect nonhuman primates against ebolavirus challenge. *J Virol*, 85(9), 4222-4233. doi: 10.1128/JVI.02407-10

Goerke, A. R., To, B. C., Lee, A. L., Sagar, S. L., & Konz, J. O. (2005). Development of a novel adenovirus purification process utilizing selective precipitation of cellular DNA. *Biotechnol Bioeng*, 91(1), 12-21. doi: 10.1002/bit.20406

Hansen, S. G., Strelow, L. I., Franchi, D. C., Anders, D. G., & Wong, S. W. (2003). Complete sequence and genomic analysis of rhesus cytomegalovirus. *J Virol*, 77(12), 6620-6636.

Harro, C. D., Robertson, M. N., Lally, M. A., O'Neill, L. D., Edupuganti, S., Goepfert, P. A., . . . Mehrotra, D. V. (2009). Safety and immunogenicity of adenovirus-vectored near-consensus HIV type 1 clade B gag vaccines in healthy adults. *AIDS Res Hum Retroviruses*, 25(1), 103-114.

Harro, C., Sun, X., Stek, J. E., Leavitt, R. Y., Mehrotra, D. V., Wang, F., . . . Merck, V. Study Group. (2009). Safety and immunogenicity of the Merck adenovirus serotype 5 (MRKAd5) and MRKAd6 human immunodeficiency virus type 1 trigene vaccines alone and in combination in healthy adults. *Clin Vaccine Immunol*, 16(9), 1285-1292. doi: 10.1128/CVI.00144-09

Havenga, M., Vogels, R., Zuijdgeest, D., Radosevic, K., Mueller, S., Sieuwerts, M., . . . Goudsmit, J. (2006). Novel replication-incompetent adenoviral B-group vectors: high vector stability and yield in PER.C6 cells. *J Gen Virol*, 87(Pt 8), 2135-2143.

Heilbronn, R., & Weger, S. (2010). Viral vectors for gene transfer: current status of gene therapeutics. *Handb Exp Pharmacol*(197), 143-170. doi: 10.1007/978-3-642-00477-3_5

Hoganson, D. K., Ma, J. C., Asato, L., Ong, M., Printz, M. A., Huyghe, B. G., . . . D'Andrea, M. J. (2002). Development of a Stable Adenoviral Vector Formulation. *Bio-Processing J.*, 1(1), 43-48.

Holman, D. H., Wang, D., Raviprakash, K., Raja, N. U., Luo, M., Zhang, J., . . . Dong, J. Y. (2007). Two complex, adenovirus-based vaccines that together induce immune responses to all four dengue virus serotypes. *Clin Vaccine Immunol*, 14(2), 182-189.

Holterman, L., Vogels, R., van der Vlugt, R., Sieuwerts, M., Grimbergen, J., Kaspers, J., . . . Havenga, M. (2004). Novel replication-incompetent vector derived from adenovirus type 11 (Ad11) for vaccination and gene therapy: low seroprevalence and non-cross-reactivity with Ad5. *J Virol*, 78(23), 13207-13215. doi: 10.1128/JVI.78.23.13207-13215.2004

Hu, X., Meng, W., Dong, Z., Pan, W., Sun, C., & Chen, L. (2011). Comparative immunogenicity of recombinant adenovirus-vectored vaccines expressing different forms of hemagglutinin (HA) proteins from the H5 serotype of influenza A viruses in mice. *Virus Res*, 155(1), 156-162. doi: 10.1016/j.virusres.2010.09.014

Kim, D. W., Uetsuki, T., Kaziro, Y., Yamaguchi, N., & Sugano, S. (1990). Use of the human elongation factor 1 alpha promoter as a versatile and efficient expression system. *Gene*, 91(2), 217-223.

Kobinger, G. P., Feldmann, H., Zhi, Y., Schumer, G., Gao, G., Feldmann, F., . . . Wilson, J. M. (2006). Chimpanzee adenovirus vaccine protects against Zaire Ebola virus. *Virology*, 346(2), 394-401. doi: 10.1016/j.virol.2005.10.042

Lasaro, M. O., & Ertl, H. C. (2009). New insights on adenovirus as vaccine vectors. *Mol Ther*, 17(8), 1333-1339. doi: 10.1038/mt.2009.130

Lemckert, A. A., Grimbergen, J., Smits, S., Hartkoorn, E., Holterman, L., Berkhout, B., . . . Havenga, M. J. (2006). Generation of a novel replication-incompetent adenoviral vector derived from human adenovirus type 49: manufacture on PER.C6 cells, tropism and immunogenicity. *J Gen Virol*, 87(Pt 10), 2891-2899. doi: 10.1099/vir.0.82079-0

Mullick, A., Xu, Y., Warren, R., Koutroumanis, M., Guilbault, C., Broussau, S., . . . Massie, B. (2006). The cumate gene-switch: a system for regulated expression in mammalian cells. *BMC Biotechnol*, 6, 43. doi: 10.1186/1472-6750-6-43

Na, M., & Fan, X. (2010). Design of Ad5F35 vectors for coordinated dual gene expression in candidate human hematopoietic stem cells. *Exp Hematol*, 38(6), 446-452. doi: 10.1016/j.exphem.2010.03.007

Nan, X., Peng, B., Hahn, T. W., Richardson, E., Lizonova, A., Kovesdi, I., & Robert-Guroff, M. (2003). Development of an Ad7 cosmid system and generation of an Ad7deltaE1deltaE3HIV(MN) env/rev recombinant virus. *Gene Ther*, 10(4), 326-336. doi: 10.1038/sj.gt.3301903

Ogun, S. A., Dumon-Seignovert, L., Marchand, J. B., Holder, A. A., & Hill, F. (2008). The oligomerization domain of C4-binding protein (C4bp) acts as an adjuvant, and the fusion protein comprised of the 19-kilodalton merozoite surface protein 1 fused with the murine C4bp domain protects mice against malaria. *Infect Immun*, 76(8), 3817-3823. doi: 10.1128/IAI.01369-07

Ophorst, O. J., Radosevic, K., Havenga, M. J., Pau, M. G., Holterman, L., Berkhout, B., . . . Tsuji, M. (2006). Immunogenicity and protection of a recombinant human adenovirus serotype 35-based malaria vaccine against *Plasmodium yoelii* in mice. *Infect Immun*, 74(1), 313-320.

Pham, L., Nakamura, T., Gabriela Rosales, A., Carlson, S. K., Bailey, K. R., Peng, K. W., & Russell, S. J. (2009). Concordant activity of transgene expression cassettes inserted into E1, E3 and E4 cloning sites in the adenovirus genome. *J Gene Med*, 11(3), 197-206.

Post, D. E., & Van Meir, E. G. (2001). Generation of bidirectional hypoxia/HIF-responsive expression vectors to target gene expression to hypoxic cells. *Gene Ther*, 8(23), 1801-1807. doi: 10.1038/sj.gt.3301605

Quilici, L. S., Silva-Pereira, I., Andrade, A. C., Albuquerque, F. C., Brigido, M. M., & Maranhao, A. Q. (2013). A minimal cytomegalovirus intron A variant can improve transgene expression in different mammalian cell lines. *Biotechnol Lett*, 35(1), 21-27. doi: 10.1007/s10529-012-1043-z Richardson, J. S., Yao, M. K., Tran, K. N., Croyle, M. A., Strong, J. E., Feldmann, H., & Kobinger, G. P. (2009). Enhanced protection against Ebola virus mediated by an improved adenovirus-based vaccine. *PLoS One*, 4(4), e5308. doi: 10.1371/journal.pone.0005308

Robbins, P. D., & Ghivizzani, S. C. (1998). Viral vectors for gene therapy. *Pharmacol Ther*, 80(1), 35-47.

Sandford, G. R., & Burns, W. H. (1996). Rat cytomegalovirus has a unique immediate early gene enhancer. *Virology*, 222(2), 310-317. doi: 10.1006/viro.1996.0428

Schepp-Berglind, J., Luo, M., Wang, D., Wicker, J. A., Raja, N. U., Hoel, B. D., . . . Dong, J. Y. (2007). Complex adenovirus-mediated expression of West Nile virus C, PreM, E, and NS1 proteins induces both humoral and cellular immune responses. *Clin Vaccine Immunol*, 14(9), 1117-1126.

Sullivan, N. J., Geisbert, T. W., Geisbert, J. B., Shedlock, D. J., Xu, L., Lamoreaux, L., . . . Nabel, G. J. (2006). Immune protection of nonhuman primates against Ebola virus with single low-dose adenovirus vectors encoding modified GPs. *PLoS Med*, 3(6), e177. doi: 10.1371/journal.pmed.0030177

Sullivan, N. J., Geisbert, T. W., Geisbert, J. B., Xu, L., Yang, Z. Y., Roederer, M., . . . Nabel, G. J. (2003). Accelerated vaccination for Ebola virus haemorrhagic fever in non-human primates. *Nature*, 424(6949), 681-684. doi: 10.1038/nature01876

Tatsis, N., Blejer, A., Lasaro, M. O., Hensley, S. E., Cun, A., Tesema, L., . . . Ertl, H. C. (2007). A CD46-binding chimpanzee adenovirus vector as a vaccine carrier. *Mol Ther*, 15(3), 608-617. doi: 10.1038/sj.mt.6300078

Vemula, S. V., & Mittal, S. K. (2010). Production of adenovirus vectors and their use as a delivery system for influenza vaccines. *Expert Opin Biol Ther*, 10(10), 1469-1487. doi: 10.1517/14712598.2010.519332

Vogels, R., Zuijdgeest, D., van Meerendonk, M., Companjen, A., Gillissen, G., Sijtsma, J., . . . Havenga, M. J. (2007). High-level expression from two independent expression cassettes in replication-incompetent adenovirus type 35 vector. *J Gen Virol*, 88(Pt 11), 2915-2924.

Vogels, R., Zuijdgeest, D., van Rijnsoever, R., Hartkoom, E., Damen, I., de Bethune, M. P., . . . Havenga, M. (2003). Replication-deficient human adenovirus type 35 vectors for gene transfer and vaccination: efficient human cell infection and bypass of preexisting adenovirus immunity. *J Virol,* 77(15), 8263-8271.

Voigt, S., Sandford, G. R., Hayward, G. S., & Burns, W. H. (2005). The English strain of rat cytomegalovirus (CMV) contains a novel captured CD200 (vOX2) gene and a spliced CC chemokine upstream from the major immediate-early region: further evidence for a separate evolutionary lineage from that of rat CMV Maastricht. *J Gen Virol,* 86(Pt 2), 263-274. doi: 10.1099/vir.0.80539-0

Walther, W., & Stein, U. (2000). Viral vectors for gene transfer: a review of their use in the treatment of human diseases. *Drugs,* 60(2), 249-271.

Zhou, D., Cun, A., Li, Y., Xiang, Z., & Ertl, H. C. (2006). A chimpanzee-origin adenovirus vector expressing the rabies virus glycoprotein as an oral vaccine against inhalation infection with rabies virus. *Mol Ther,* 14(5), 662-672. doi: 10.1016/j.ymthe.2006.03.027

Zhou, D., Wu, T. L., Lasaro, M. O., Latimer, B. P., Parzych, E. M., Bian, A., . . . Ertl, H. C. (2010). A universal influenza A vaccine based on adenovirus expressing matrix-2 ectodomain and nucleoprotein protects mice from lethal challenge. *Mol Ther,* 18(12), 2182-2189. doi: 10.1038/mt.2010.202

The invention claimed is:

1. A recombinant nucleic acid molecule comprising a bidirectional promoter operably linked to a first transgene in one direction and to a second transgene in the opposite direction, wherein the bidirectional promoter comprises:
   a cytomegalovirus major immediate early enhancer as an enhancer building block, flanked by
   a human cytomegalovirus major immediate early promoter (hCMV promoter) as a first promoter building block, and
   a chicken beta actin promoter as a second promoter building block, with
   a hybrid chicken beta actin/rabbit beta globin intron as a first intron building block adjacent to and downstream of the chicken beta actin promoter, and
   a human apolipoprotein A-1 intron as a second intron building block directly contiguous with and downstream of the hCMV promoter building block,
   wherein the bidirectional promoter comprises a sequence that is at least 90% identical to the sequence of SEQ ID NO: 4.

2. The recombinant nucleic acid molecule of claim 1, wherein the bidirectional promoter comprises the sequence of SEQ ID NO: 4.

3. The recombinant nucleic acid molecule of claim 1, wherein the first and the second transgenes are different and at least one of them encodes an antigen.

4. A recombinant vector or a recombinant virus, comprising the recombinant nucleic acid molecule according to claim 3.

5. A recombinant vector or a recombinant virus, comprising the recombinant nucleic acid molecule according to claim 1.

6. A recombinant vector according to claim 5, wherein the vector is a plasmid vector.

7. A pharmaceutical composition comprising a recombinant vector according to claim 6 and a pharmaceutically acceptable carrier or excipient.

8. A recombinant virus according to claim 5, wherein the virus is an adenovirus.

9. The recombinant adenovirus according to claim 8, wherein the adenovirus has a deletion in the E1 region.

10. The recombinant adenovirus of claim 8, wherein the adenovirus is selected from the group consisting of a human adenovirus serotype 35, and a human adenovirus serotype 26, a human adenovirus serotype 35 with a deletion in the E1 region, and a human adenovirus serotype 26 with a deletion in the E1 region.

11. A pharmaceutical composition comprising a recombinant adenovirus according to claim 10 and a pharmaceutically acceptable carrier or excipient.

12. A recombinant DNA molecule comprising the genome of a recombinant adenovirus according to claim 8.

13. A pharmaceutical composition comprising a recombinant virus according to claim 8 and a pharmaceutically acceptable carrier or excipient.

14. A pharmaceutical composition comprising a recombinant vector or a recombinant virus according to claim 5 and a pharmaceutically acceptable carrier or excipient.

15. A recombinant nucleic acid molecule comprising a bidirectional promoter operably linked to a first transgene in one direction and to a second transgene in the opposite direction, wherein the bidirectional promoter comprises:
- a cytomegalovirus major immediate early enhancer as an enhancer building block, flanked by
- a human cytomegalovirus major immediate early promoter (hCMV promoter) operably linked to the first transgene as a first promoter building block,
- a chicken beta actin promoter operably linked to the second transgene as a second promoter building block, with
- a hybrid chicken beta actin/rabbit beta globin intron as a first intron building block adjacent to and downstream of the chicken beta actin promoter, and
- a human apolipoprotein A-1 intron as a second intron building block adjacent to and downstream of the hCMV promoter building block,
- wherein the bidirectional promoter comprises a sequence that is at least 90% identical to the sequence of SEQ ID NO: 4, and
- wherein the second intron building block is not downstream of the first transgene.

\* \* \* \* \*